US009649372B2

(12) United States Patent
Harper et al.

(10) Patent No.: US 9,649,372 B2
(45) Date of Patent: May 16, 2017

(54) IMMUNOGENIC COMPOSITIONS AND RELATED METHODS

(75) Inventors: Kevin Harper, Cheltenham (CA); Belma Ljutic, Thornhill (CA); Scott Gallichan, Burlington (CA); Martina Ochs-Onolemhemhen, Lyons (FR); Garry Morefield, Nazareth, PA (US); Fernando Ausar, Markham (CA); Marie-Danielle Salha, Toronto (CA)

(73) Assignee: SANOFI PASTEUR LIMITED, Toronto, Ontario (CA)

( * ) Notice: Subject to any disclaimer, the term of this patent is extended or adjusted under 35 U.S.C. 154(b) by 0 days.

(21) Appl. No.: 13/516,140

(22) PCT Filed: Dec. 20, 2010

(86) PCT No.: PCT/CA2010/001975
§ 371 (c)(1),
(2), (4) Date: Oct. 22, 2012

(87) PCT Pub. No.: WO2011/075822
PCT Pub. Date: Jun. 30, 2011

(65) Prior Publication Data
US 2013/0034579 A1 Feb. 7, 2013

Related U.S. Application Data

(60) Provisional application No. 61/289,077, filed on Dec. 22, 2009, provisional application No. 61/289,236, filed on Dec. 22, 2009, provisional application No. 61/325,615, filed on Apr. 19, 2010.

(51) Int. Cl.
| A61K 39/02 | (2006.01) |
| A61K 49/00 | (2006.01) |
| A61K 45/00 | (2006.01) |
| A61K 39/39 | (2006.01) |
| A61K 9/00 | (2006.01) |
| A61K 39/09 | (2006.01) |
| A61K 47/26 | (2006.01) |
| A61K 39/00 | (2006.01) |

(52) U.S. Cl.
CPC ............ *A61K 39/39* (2013.01); *A61K 9/0019* (2013.01); *A61K 39/092* (2013.01); *A61K 47/26* (2013.01); *A61K 2039/55505* (2013.01)

(58) Field of Classification Search
USPC ...... 424/9.1, 9.2, 184.1, 234.1, 237.1, 278.1
See application file for complete search history.

(56) References Cited

U.S. PATENT DOCUMENTS

| 6,716,432 B1 | 4/2004 | Paton et al. |
| 2004/0081662 A1 | 4/2004 | Hermand et al. |
| 2006/0051361 A1 | 3/2006 | Laferriere et al. |
| 2007/0065458 A1 | 3/2007 | Johnson et al. |
| 2007/0082875 A1 | 4/2007 | Fang et al. |
| 2007/0231340 A1 | 10/2007 | Hausdorff et al. |
| 2008/0112964 A1 | 5/2008 | Kirkham et al. |
| 2008/0124794 A1 | 5/2008 | Doucette-Stamm et al. |
| 2009/0110699 A1 | 4/2009 | Cigarini et al. |
| 2010/0143399 A1 | 6/2010 | Biemans et al. |
| 2010/0227341 A1 | 9/2010 | Briles et al. |
| 2010/0297133 A1 | 11/2010 | Ochs et al. |
| 2011/0002962 A1 | 1/2011 | Briles et al. |
| 2011/0130300 A1 | 6/2011 | Ochs-Onolemhemhen et al. |
| 2011/0243976 A1 | 10/2011 | Donati et al. |
| 2011/0287046 A1 | 11/2011 | Oloo et al. |
| 2013/0183350 A1 | 7/2013 | Gallichan et al. |

FOREIGN PATENT DOCUMENTS

| WO | 9006951 A1 | 6/1990 |
| WO | WO 2011075822 | 6/2011 |

OTHER PUBLICATIONS

Glover, D.T., et al. Infection and Immunity, vol. 76, No. 6, pp. 2767-2776, Jun. 2008.*
Hem, S.L., et al. Expert Reviews of Vaccines, vol. 6, No. 5, pp. 685-698, 2007.*
Adamou, et al. Identification and characterization of a novel family of pneumococcal proteins that are protective against sepsis. Inf. Imm. 69(2): 949-958 (2001).
Alving, et al. Ann. NY Acad. Sci. 690:265-275 (1993).
Bogaert, et al. Streptococcus pneumoniae colonisation: the key to pneumococcal disease. Lancet Infect. Dis. 4:144-154 (2004).
Chang, et al. Degree of antigen adsorption in the vaccine or interstitial fluid and its effect on the antibody response in rabbits. Vaccine, 19:2884-9 (2001).
Di Fabio, et al. Evolution of Streptococcus pneumoniae serotypes and penicillin susceptibility in Latin America, Sireva-Vigia Group, 1993 to 1999. Pediatr. Infect. Dis. J. 20:959-967 (2001).
Diminsky, et al. Physical, chemical and immunological stability of CHO-derived hepatitis B surface antigen (HBsAg) particles. Vaccine 18:3-17 (1999).
Edwards, et al. Combination vaccines consisting of acellular pertussis vaccines. Pediatr. Infect. Dis. J. 16(4 Suppl.):S97-S102 (1997).
Eskola, et al. Efficacy of a Pneumococcal Conjugate Vaccine against Acute Otitis Media. N. Engl. J. Med. 344-403-409 (2001).
Fedson, et al. The burden of pneumococcal disease among adults in developed and developing countries: what is known and what is not known, Vaccine 17, S11-S18 (1999).
Fedson, et al. "Pneumococcal Polysaccharide Vaccine", pp. 529-588; In Vaccines. S.A. Plotikin and W.A. Orenstein (eds.), W.B. Saunders and Co., Philadelphia, PA (2004).
Garland, et al. Noninferiority of Antibody Response to Human Papillomavirus Type 16 in Subjects Vaccinated with Monovalent and Quadrivalent L1 Virus-Like Particle Vaccines. Clinical and Vaccine Immunology, 14: 792-795 (2007).
Genbank Accession No. ABO21381 (Jan. 11, 2010).
Genbank Accession No. CAB04758 (Nov. 14, 2006).

(Continued)

Primary Examiner — Rodney P Swartz
(74) Attorney, Agent, or Firm — Patrick J. Halloran

(57) ABSTRACT

This disclosure relates to adjuvants for use in immunogenic compositions comprising at least one antigen and an aluminum compound comprising hydroxyl groups that has been treated with phosphate, carboxylate, carbonate, sulfate diphosphonate or a mixture of two or more of these compounds and methods of using these compositions for preventing and treating diseases are also provided.

53 Claims, 20 Drawing Sheets

(56) References Cited

OTHER PUBLICATIONS

Genbank Accession No. P0C2J0 (Mar. 6, 2007).
Genbank Accession No. Q04IN8 (Mar. 6, 2007).
Genbank Accession No. Q7ZAK5 (Mar. 6, 2007).
Genbank Accession No. YP816370 (Jul. 17, 2006).
Glover, et al. Streptococcus pneumonia Surface Protein A Elicits Protection against Lung Infection and Fatal Sepsis. Inf. Immun. 76(6): 2767-2776 (2008).
Gupta, R. Aluminum compound as vaccine adjuvants. Adv Drug Deliv Rev. Jul. 6, 1998: 32(3):155-172.
Hansen, et al. Relationship between the strength of antigen adsorption to an aluminum-containing adjuvant and the immune response. Vaccine, 25:6618-6624 (2007).
Hansen, et al. Effect of the strength of adsorption of hepatitis B surface antigen to aluminum hydroxide adjuvant on the immune response. Vaccine, 27(6): 888-892 (2007).
Hem, et al. Relationship between physical and chemical properties of aluminum-containing adjuvants and immunopotentiation. Exp. Rev. Vacc. 6(5): 685-698 (2007).
Hem, et al. Imject® Alum in not aluminum hydroxide adjuvant or aluminum phosphate adjuvant. Vaccine 25:4985-4986 (2007).
Henrichsen, et al. Six newly recognized types of Streptococcus pneumoniae, J. Clin. Microbiol. 33(10): 2759-2762 (1995).
Hirst, et al. The role of pneumolysin in pneumococcal pneumonia and meningitis. Clin. Exp. Immunol. 138: 195-201 (2004).
Iyer, et al. Effect of the degree of phosphate substitution in aluminum hydroxide adjuvant on the adsorption of phosphorylated proteins. Pharm. Dev. Technol. 8(1): 81-86 (2003).
Iyer, et al. Mechanism of adsorption of hepatitis B surface antigen by aluminum hydroxide adjuvant. Vaccine, 29:1475-9 (2004).
Jendreck, et al. Evaluation of the compatibility of a second generation recombinant anthrax vaccine with aluminum-containing adjuvants. Vaccine, 21: 3011-8 (2003).
Jezek, et al. A heat-stable Hepatitis B vaccine formulation. Human Vaccines, 5(8): 529-35 (2009).
Jones, et al. Effects of adsorption to aluminum salt adjuvants on the structure and stability of model protein antigens. J. Biol. Chem. 280(14): 13406-13414 (2005).
Klein, D.L. Pneumococcal disease and the role of conjugate vaccines. Microb. Drug Resis. 5, 14-157 (1999).
Little, et al. Effect of aluminum hydroxide adjuvant and formaldehyde in the formulation of rPA anthrax vaccine. Vaccine, 25:2771-2777 (2007).
Maa, et al. Stabilization of alum-adjuvanted vaccine dry powder formulations: Mechanism and application. J. Pharm. Sci. 92:319-332 (2003).
Mbelle, et al. Immonugenicity and Impact on Nasopharyngeal Carriage of Nonavalent Pneumococcal Conjugate Vaccine, J. Infect. Dis. 180 :1171-1176 (1999).
Mendez, et al. Potentiation of the immune response to non-adsorbed antigens by aluminum-containing adjuvants. Vaccine, 25(5):825-33 (2007).
Morefield, et al. Role of aluminum-containing adjuvants in antigen internalization by dendritic cells in vitro. Vaccine, 23(13):1588-95 (2005).
Muholland, et al. The Gambian pneumococcal vaccine trial—implications for control of childhood pneumonia. Trop. Med. Int. Health 10:497-500 (2005).
Park, et al. Discovery of a new capsular serotype (6C) within serogroup 6 of Streptococcus pneumoniae. J. Clin. Microbiol. 45, 1225-1233 (2007).
Prevnar® (package insert). Wyeth Pharmaceuticals Inc. Philadelphia, PA, 2006.
Quagliarello, et al. Mechanisms of Disease: Bacterial Meningitis: Pathogenesis, Pathophysiology, and Progress. N. Engl. J. Med. 327:864-872 (1992).
Rahav, et al. Invasive pneumococcal infection: A comparison between adults and children. Medicine 76, 295:303 (1997).
Rinella, et al. Treatment of aluminum hydroxide adjuvant to optimize the adsorption of basic proteins. Vaccine, 14(4):298-300 (1996).
Rudan, et al., Global estimate of the incidence of clinical pneumonia among children under five years of age. Bulletin of World Health Organization, 82(12):895-903 (2004).
Seeber, et al. Predicting the adsorption of proteins by aluminum-containing adjuvants. Vaccine, 9:201-3 (1991).
Shapiro, et al. The Protective Efficacy of Polyvalent Pneumococcal Polysaccharide Vaccine, N. Engl. J. Med. 325:1453-1460 (1991).
Shirodkar, et al. Compounds Used as Adjuvants in Vaccines. Pharm. Res. 7(12): 1282-1288 (1990).
Siber, et al. Pneumococcal Vaccines: The Impact of Conjugate Vaccine. Washington DC: ASM Press; 2008.
Tai, et al. Streptococcus pneumoniae protein vaccine candidates: properties, activities and animal studies. Crit. Rev. Microbiol. 32(3): 139-53 (2006).
Warren, et al. Current Status of Immunological Adjuvants. Ann Rev Immunol. 4:369-388 (1986).
Wittayanukulluk, et al. Effect of microenvironment pH of aluminum hydroxide adjuvant on the chemical stability of adsorbed antigen. Vaccine, 22(9-10): 1172-76 (2004).
World Health Organization, Guidelines on nonclinical evaluations vaccines. Technical report series No. 927 (2005).
World Health Organization, Pneumococcal conjugate vaccine for childhood immunization—WHO position paper. Wkly Epidemiol. Rec. 82, 93-104 (2007).
Zhang, et al. Recombinant PhpA Protein, a Unique Histidine Motif-Containing Protein from Streptococcus pneumoniae, Protects Mice against Intranasal Pneumococcal Challenge, Infect. Immun. 69:3827-3836 (2001).
Zheng, et al. The structural stability of protein antigens adsorbed by aluminum hydroxide in comparision to the antigens in solutions. Spectroscopy, 21(5-6):257-268 (2007).
Ogunniyi, et al. Development of a Vaccine Against Invasive Pneumococcal Disease Based on Combinations of Virulence Proteins of Streptococcus Pneumoniae. Inf. Imm. 75(1):350-7 (2007).

\* cited by examiner

Figures 1A and B: Stability of PcpA formulated with AlO(OH) or 2 mM PTH
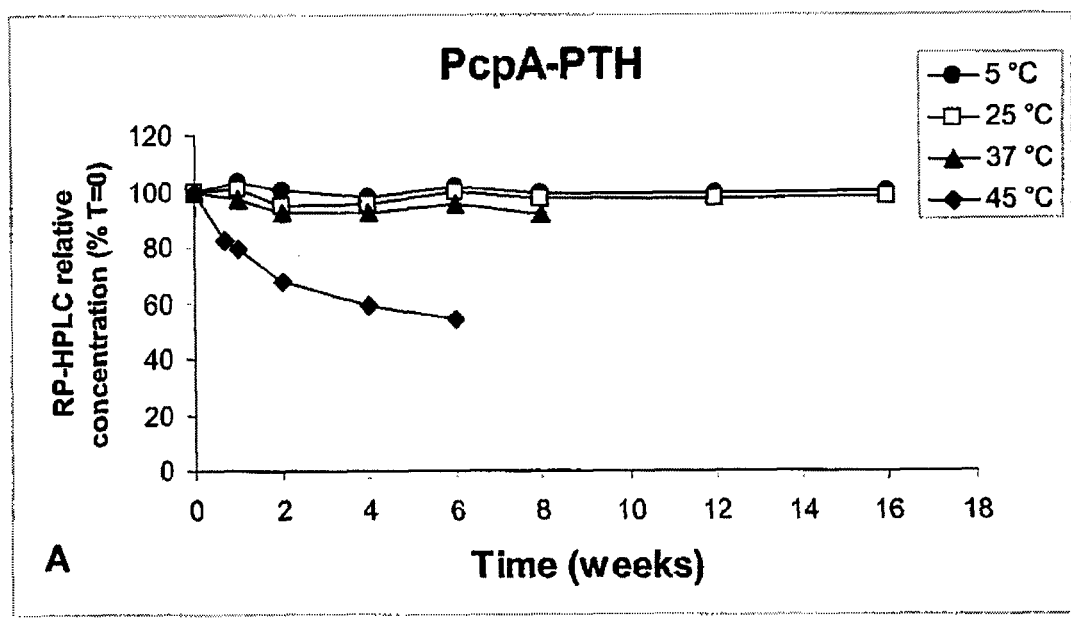
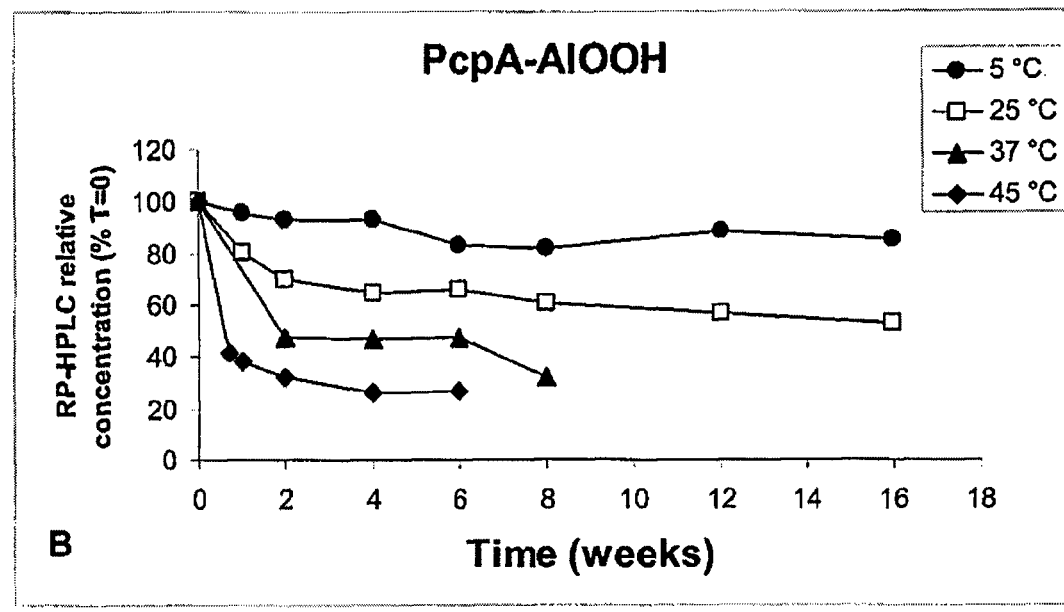

Figures 1C and D: Stability of PhtD formulated with AlO(OH) or 2 mM PTH
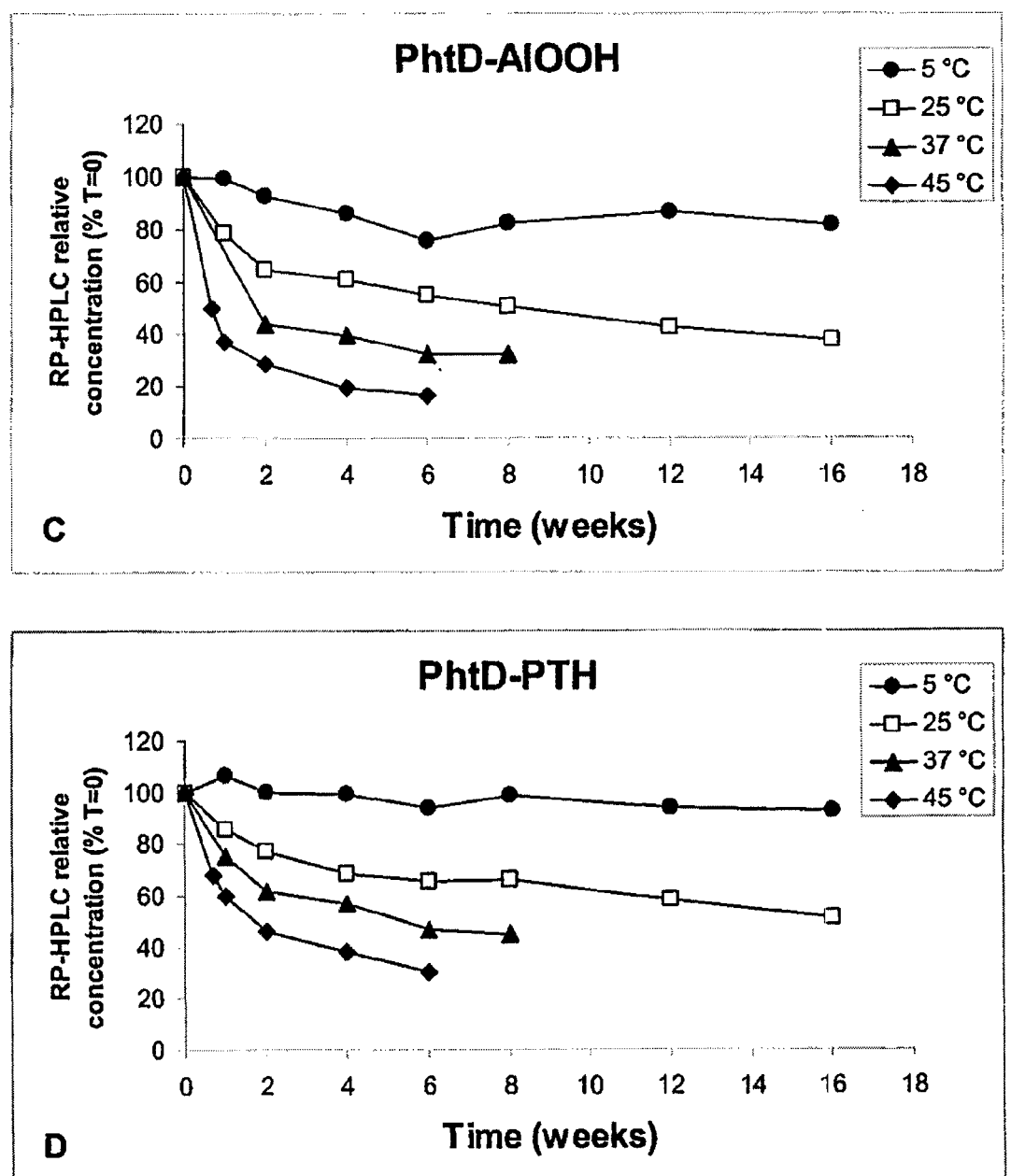

Figure 1e and f: Stability of PcpA formulated with AlO(OH) or 2mM PTH
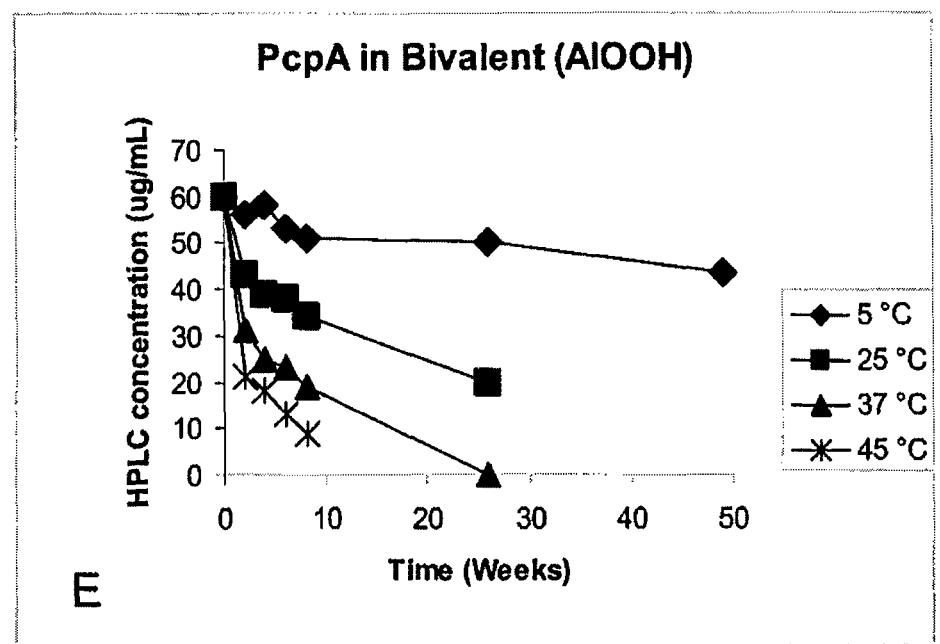
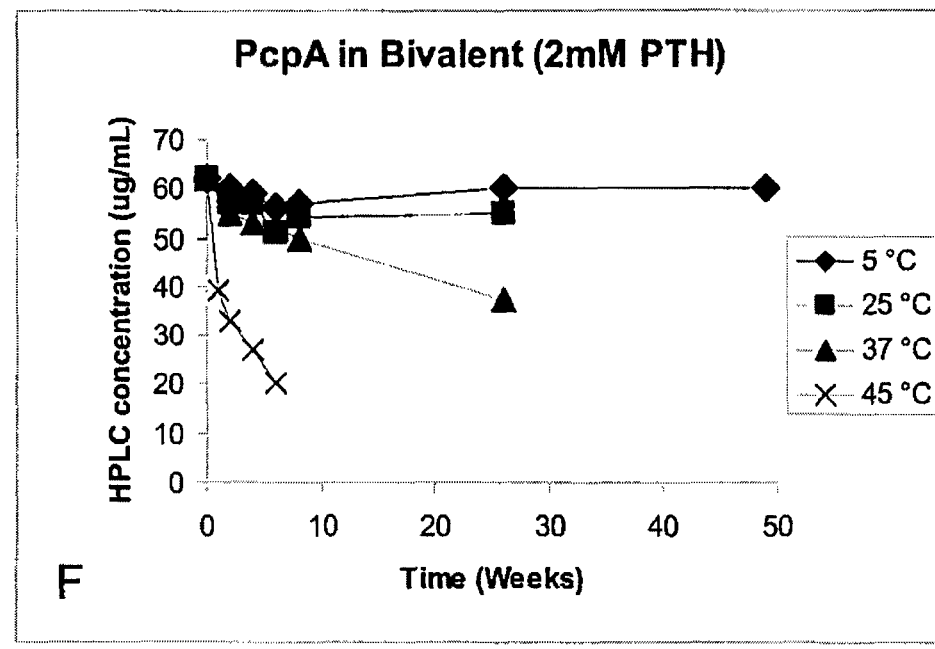

Figure 2: Stability of PhtD and PcpA under stress conditions as evaluated by ELISA.
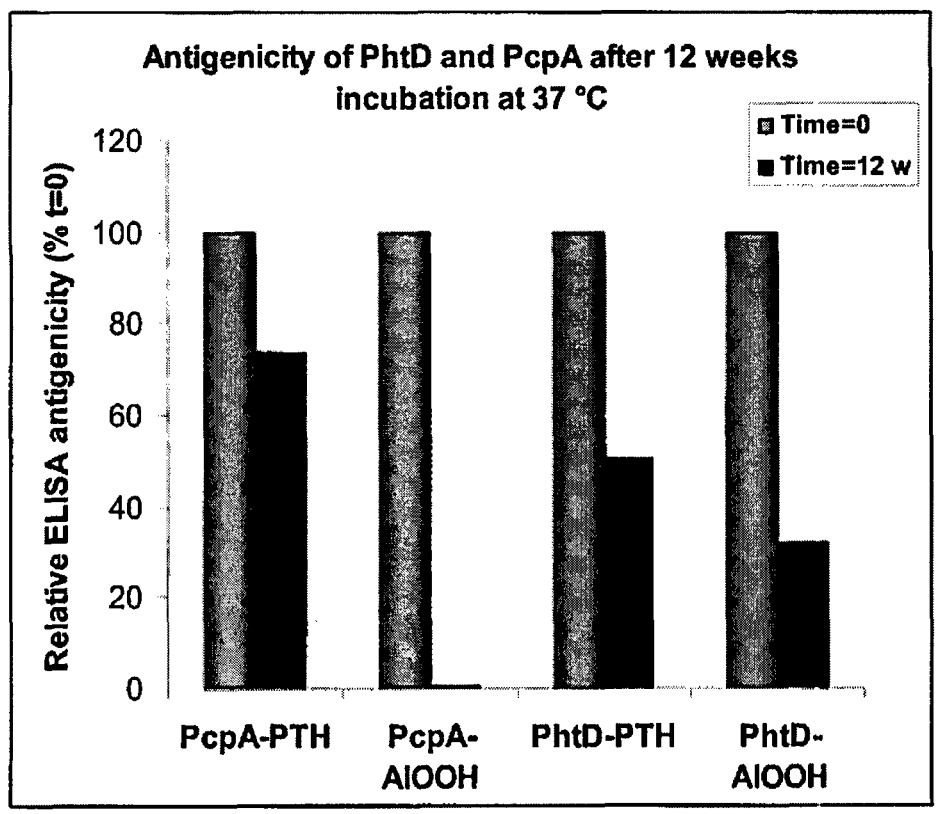
Bivalent formulations at 100 ug/mL were incubated at 37°C for 12 weeks and the antigenicity was evaluated by ELISA.

Figure 3: Formulation Process Overview
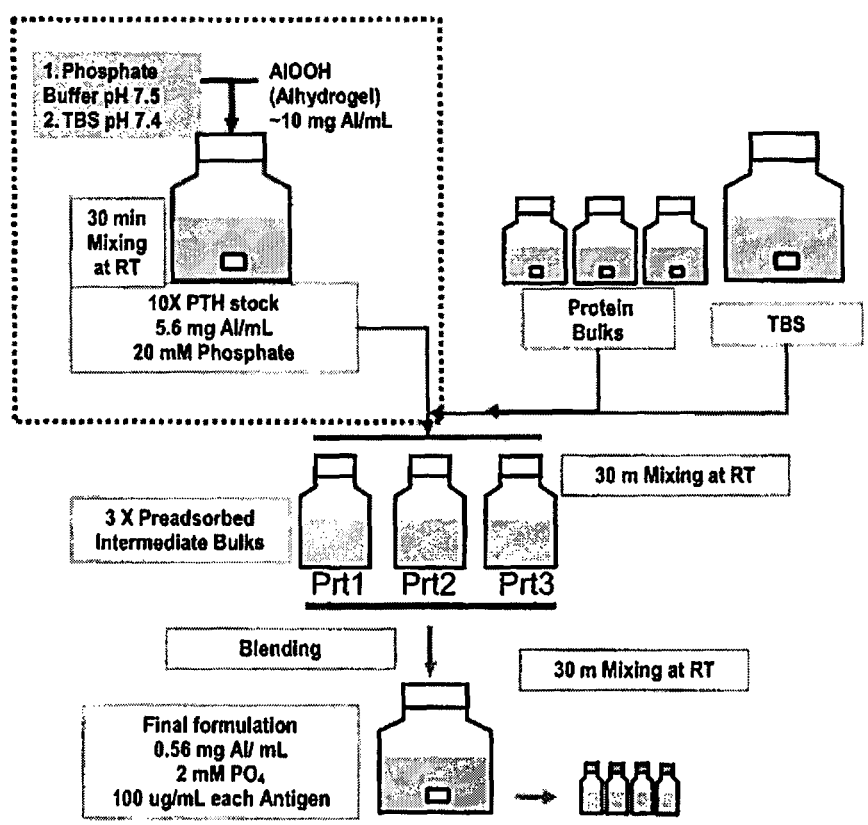

Depicts the survival percentage for each group of mice immunized (Example 6). In this study, a bivalent formulation of recombinant PhtD and PcpA was evaluated using an intranasal challenge model. Immunized animals were challenged with a lethal dose of an *S. pneumoniae* strain (MD, 14453 or 941192).

Figure 7: Bleed 3 anti-PcpA and anti-PhtD antibody titres
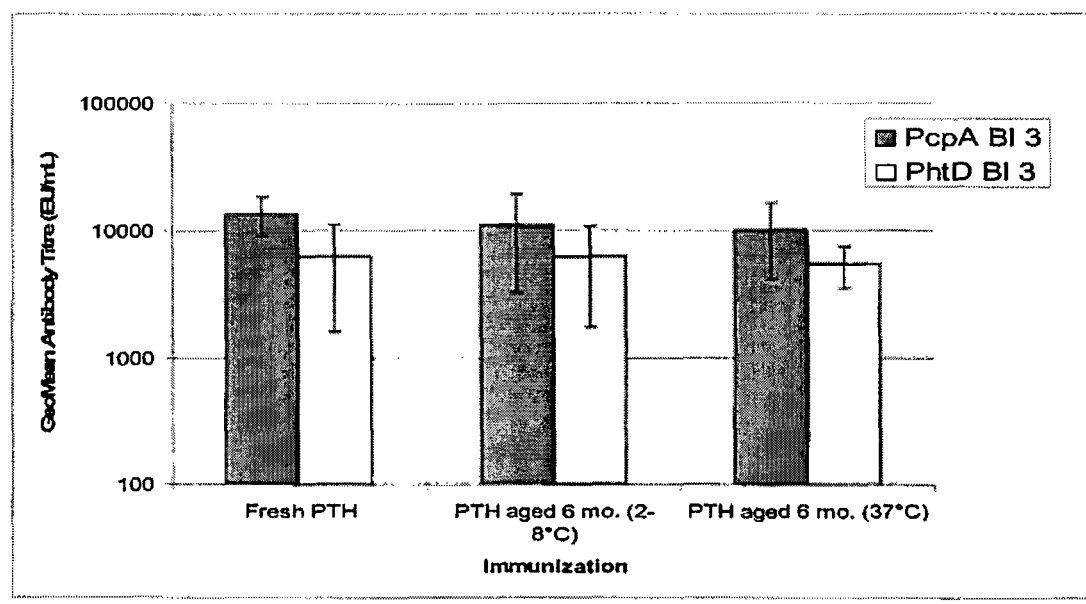

Figure 8 Immunogenicity study
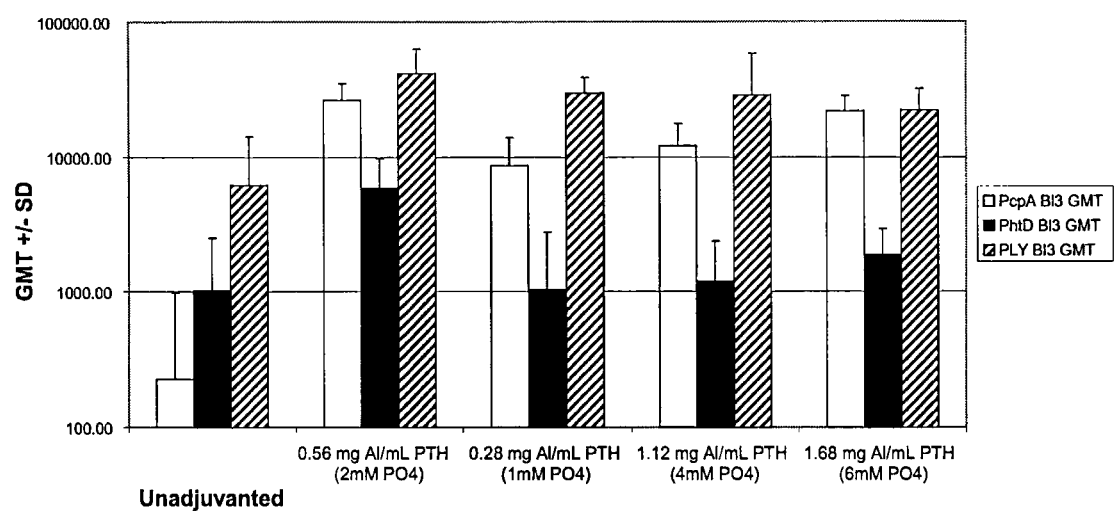

X-ray diffraction patterns of different lots of AlOOH

[08-127905-23800_11.raw]Aluminum Hydroxyde Gel Study # CA-08-028batch#85335.SCAN:50700002/1.2(sec).Cu. 1(max)=770.04.09.08 08:21a

*X-ray diffraction patterns of different lots of PTH*

[09-12-13312-38089_11.raw] 10xPTH(washed). lotCA-09-136C-PTH.
SCAN50/70.02/1.2(sec),Cu, I(max)=974.0.10/10/09 4:33p

*X-ray diffraction patterns of different lots of AlPO₄*

TEM analysis of AlOOH (Alhydrogel)

*TEM analysis of AlPO$_4$ (Adjuphos)*

*TEM analysis of PTH*

*TEM analysis of PTH*

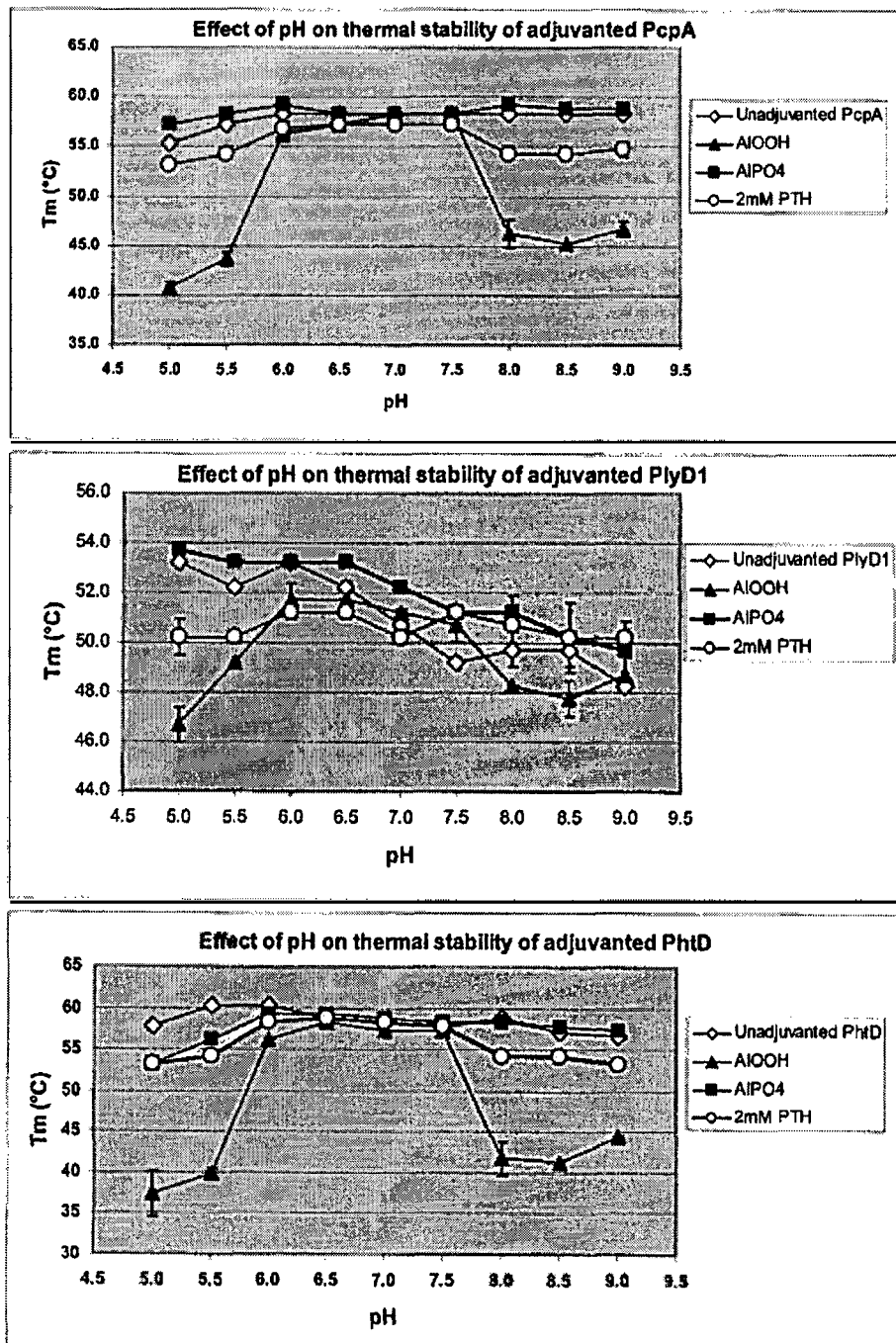
Figure 11. Effect of pH on the thermostability of PcpA, PlyD1 and PhtD Figure 12. Effect of selected GRAS excipients and pH on chemical stability and antigenicity of PcpA

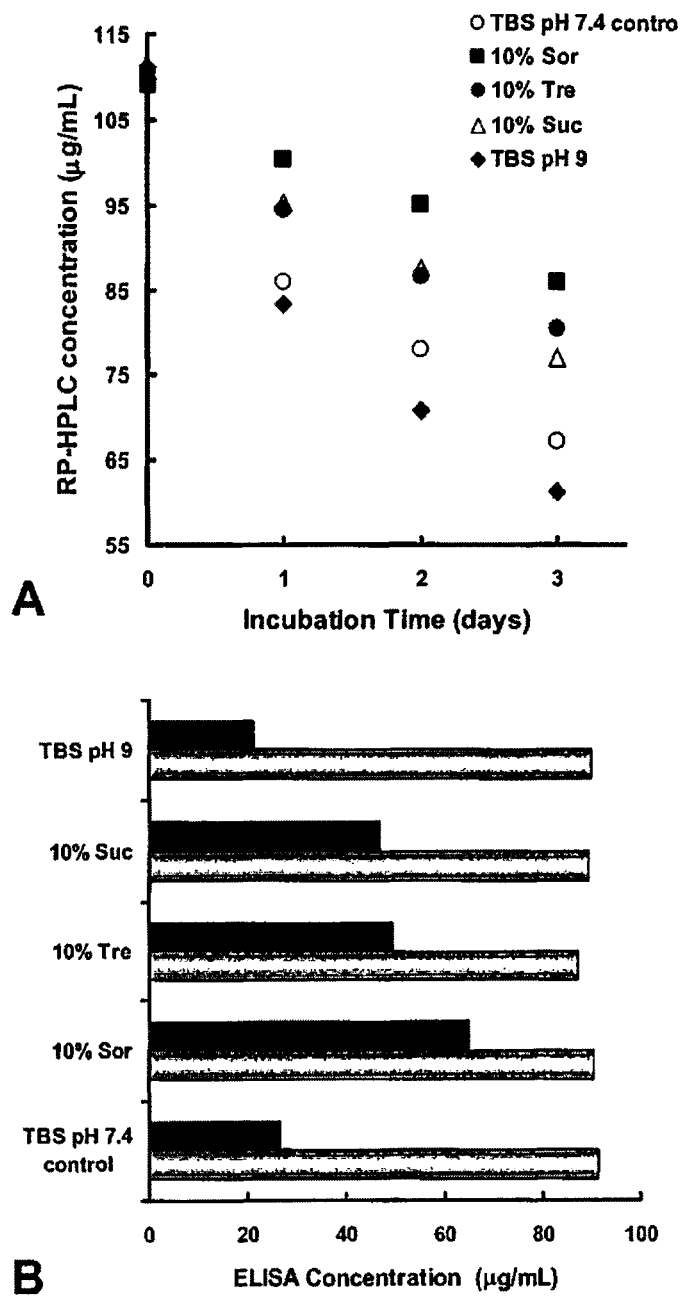

Adjuvanted formulations of PcpA at 100 μg/mL were incubated 3days at 50 °C in the presence of selected excipients and chemical integrity was determined by RP-HPLC (A). Antigenicity was evaluated for each formulation by a quantitative ELISA sandwich at time zero (white bars) and three days of incubations (black bars) at 50 °C (B).

IMMUNOGENIC COMPOSITIONS AND RELATED METHODS

CROSS-REFERENCE TO RELATED APPLICATIONS

The present applications is a 35 U.S.C. §371 national stage application of International Application No. PCT/CA10/01975, filed Dec. 20, 2010, and claims priority to U.S. provisional application No. 61/289,077 filed Dec. 22, 2009; 61/289,236 filed Dec. 22, 2009; and 61/325,615 filed Apr. 19, 2010, which are incorporated by reference herein in their entireties.

FIELD OF INVENTION

The present invention relates to the field of immunology and, in particular, to adjuvants and their use in immunization.

BACKGROUND

Adjuvants are agents incorporated into vaccine formulations to enhance the immunogenicity of vaccine antigens. Aluminum salts (such as aluminum phosphate and aluminum hydroxide) are the most commonly used adjuvants used in human and veterinary vaccines today. While a number of aluminum containing adjuvants are available, for any one specific vaccine formulation, adjuvant/antigen effects provided by one may not be optimal.

Two methods have commonly been used to prepare vaccines and toxoids with aluminum compounds—in situ precipitation of aluminum compounds in the presence of antigen and adsorption of antigen onto preformed aluminum gel. Adsorption of antigens on aluminum, adjuvants, either during in situ precipitation of aluminum adjuvants or onto preformed aluminum gels, is dependant on the physical and chemical characteristics of the antigen, the type of aluminum adjuvant used and the conditions of adsorption. Factors which may affect an antigen's adsorption onto an aluminum adjuvant include electrostatic forces, hydrophobic interactions, Van der Waals forces, hydrogen binding, pH, temperature, size of gel particles, and the ionic strength of reaction mixture. In general, antigens are adsorbed to aluminum adjuvants through electrostatic attraction (i.e., adjuvant and antigen have opposite charges) and/or ligand exchange (e.g., phosphate group on antigen displaces a hydroxyl group on the adjuvant surface) (Seeber S J, et al Vaccine 1991; 9:201-3; Iyer S. et al, Vaccine 2004; 29:1475-9).

Aluminum hydroxide in its dehydrogenated, crystalline form is chemically aluminum oxyhydroxide [AlO(OH)] and in its aqueous phase, it becomes aluminum trihydroxide [Al(OH)$_3$] by acquiring an additional water molecule (Hem S. L. et al 2007 Vaccine 25:4985-4986). Aluminum oxyhydroxide has a point of zero charge (PZC) of 11 and as such, is positively charged at pH 7.4. This positive charge makes aluminum oxyhydroxide a good adsorbent for negatively charged antigens (e.g. acidic proteins).

In one study, pretreatment of aluminum hydroxide adjuvant with phosphate anion was found to alter the surface charge characteristics of the adjuvant so that a basic protein (lysozyme, i.e. p.+11.1) could be adsorbed. The phosphate anion was found to reduce the adjuvant's positive zeta ($\zeta$) potential (mV) and this alteration of the surface charge of the adjuvant changed the electrostatic forces between the adjuvant and lysozyme from repulsive to attractive such that the protein was adsorbed by the adjuvant (Rinella Jr. J. V., et al., Vaccine 1996; 14(no.4):298-300).

The maximum amount of antigen that can be adsorbed as a monolayer to the adjuvant is referred to as the "adsorptive capacity" and the strength of the adsorption force is called the "adsorptive coefficient" (Jendrick et al, Vaccine 2003; 21:3011-8). Studies of the effect of adsorptive capacity on vaccine immunogenicity suggest that the percentage of the antigen dose adsorbed is unrelated to a formulation's immunogenicity (Chang M-F. et al., Vaccine 2001;19:2884-9; Romero Mendez I Z et al Vaccine 2007; 25(5):825-33). In contrast, one study has shown a correlation between the adsorptive coefficient of an antigen to an aluminum containing adjuvant and the immune response elicited by the formulation (Hansen et al., Vaccine 2007; 25:6618-6624).

Adsorption may affect a protein's structure and stability. Results from studies on the effect of adsorption to aluminum containing adjuvants are not entirely consistent: in one, three proteins (bovine serum albumin (BSA), lysozyme and ovalbumin) were destabilized following adsorption onto Alhydrogel® or Adju-Phos®; in another study, the structure of BSA and Î²-lactoglobuline (BLG) was stabilized by adsorption onto aluminum hydroxide (Jones L. S. et al., J. Biol Chem 2005; 280(14):13406-13414; Zheng Y. et al., Spectroscopy 2007;21(5-6):257-268). Methods for stabilizing for storage liquid formulations of vaccine compositions with aluminum salt adjuvants include lypohilization, freezing and freeze-drying, but often result in adjuvant agglomeration, decreased immunogen concentration and loss of immunogenicity (e.g., Maa et al, (2003) J. Pharm. Sci. 92:319-332; Diminsky et al. (1999) Vaccine 18:3-17; Alving et al (1993) Ann. NY Acad. Sci. 690:265-275; and Warren et al (1986) Ann Rev Immunol. 4:369-388, all of which are incorporated by reference). Even for those formulations maintained under refrigerated conditions (e.g. 2° C. to 8° C.) adsorbed antigens may be chemically unstable and as such, over time may under go hydrolysis and fragmentation. Therefore, a process for the production of a vaccine composition comprising an aluminum salt adjuvant that addresses these issues (e.g., chemical instability, decrease in antigen concentration) is needed.

SUMMARY OF INVENTION

The present invention is directed to methods of preparing immunogenic compositions comprising at least one antigen and an aluminum compound comprising hydroxyl groups with increased antigen stability. The methods comprise: (a) treating the aluminum compound comprising hydroxyl groups with a compound selected from the group comprising: (i) phosphate, (ii) carboxylate, (iii) carbonate, (iv) sulfate, (v) diphosphonate and (vi) a mixture of two or more of (i) to (v); and (b) mixing the preparation in step (a) with at least one antigen. The aluminum compound may alternatively be treated with fluoride. The mixing of the antigen with the treated aluminum compound comprising hydroxyl groups increases the stability of the antigen relative to a composition where the antigen is mixed with an untreated aluminum compound comprising hydroxyl groups.

Immunogenic compositions comprising at least one antigen and an aluminum compound comprising hydroxyl groups that has been treated with phosphate, carboxylate, carbonate, sulfate diphosphonate, fluoride or a mixture of two or more of these compounds and methods of using these compositions for preventing and treating diseases are also provided.

In one example, a composition comprising the *S. pneumonaie* protein PcpA and an aluminum compound comprising hydroxyl groups that has been treated with one of the selected compounds (e.g., phosphate) is prepared in accordance to the disclosed methods. The composition may also include a *S. pneumoniae* protein from the polyhistidine triad family (PhtX:PhtA, PhtB, PhtD, PhtE) and/or detoxified pneumolysin.

The invention provides several advantages. For example, the compositions of the invention are immunogenic and have improved stability. Other features and advantages of the invention will be apparent from the following Detailed Description, the Drawings, and the Claims.

BRIEF DESCRIPTION OF FIGURES

The present invention will be further understood from the following description with reference to the drawings.

FIGS. 1a to f. The stability of PcpA and PhtD in multivalent formulations (formulated with AlO(OH) or phosphate treated AlO(OH) (PTH), formulations were prepared using AlO(OH) or PTH with a final concentration of 2mM phosphate and then incubated for 30 weeks at various temperatures (i.e., 5° C., 25° C., 37° C. or 45° C.). Intact antigen concentration was then assessed by RP-HPLC.

FIG. 2. Stability of PhtD and PcpA under stress conditions as evaluated by ELISA. Bivalent formulations at 100 µg/mL were incubated at 37° C. for 12 weeks and the antigenicity was evaluated by ELISA.

FIG. 3. Is a diagrammatic representation of a formulation process overview for antigens (Prt1, Prt2 and Prt3) and an aluminum compound of the present invention.

FIG. 7. Depicts the total antigen-specific IgG titres measured by quantitative ELISA and geometric mean titres (+/−SD) for each group. In this study (Example 6), Balb/c mice were used to assess the immune response elicited by freshly prepared and aged adjuvanted bivalent formulations.

To prepare the bivalent formulations, recombinant PhtD and PcpA were formulated with AlOOH treated with $PO_4$ (2 mM). Aged formulations had been stored at 2 to 8° C. or 37° C. for approximately 6 to 7 months prior to the start of the study. The freshly prepared formulations used in the study were prepared within one week of the first immunization. Groups of mice were immunized intramuscularly (IM) three times at 3 week intervals with the applicable formulation.

FIG. 8. Depicts the total antigen-specific IgG titres measured by quantitative ELISA and geometric mean titres (+/−SD) for each group. In this study (Example 8), Balb/c mice were used to assess the immune response elicited by multivalent formulations with phosphate pretreated AlO(OH) and varying concentrations of elemental aluminum.

Figure 9A:
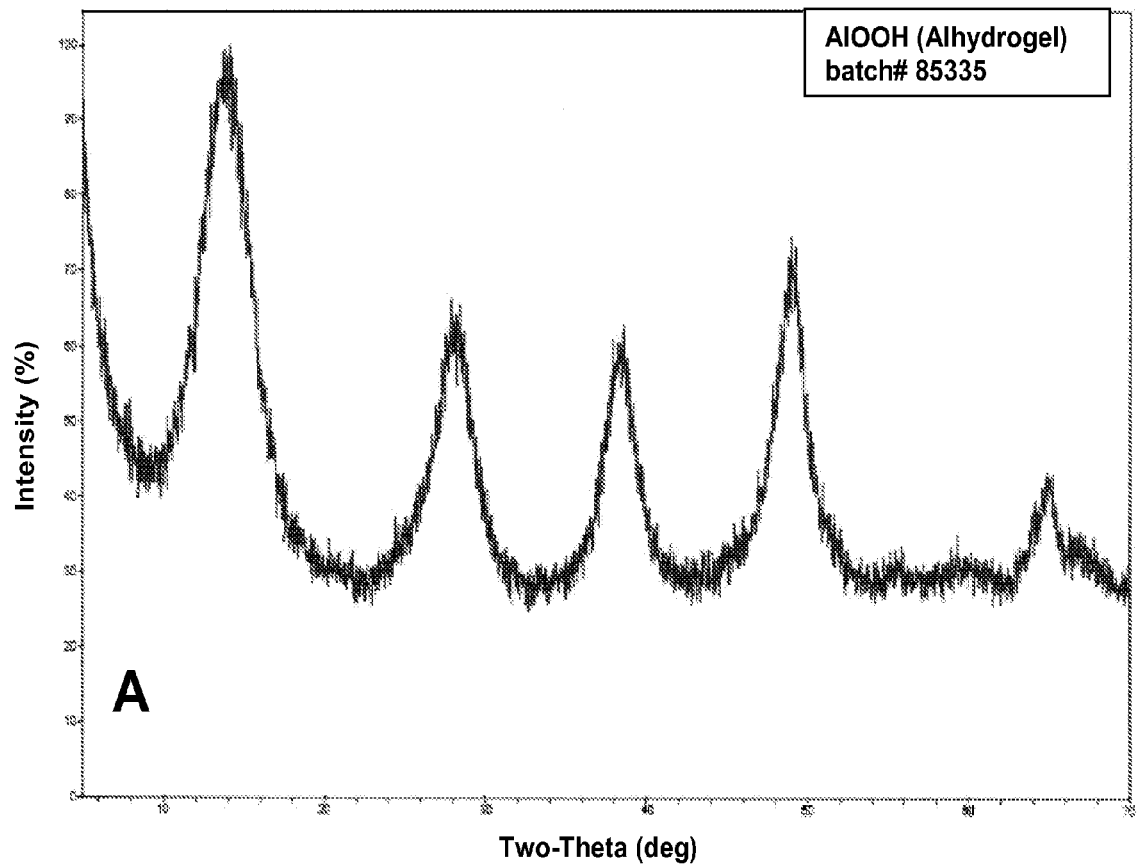
Figure 9B:
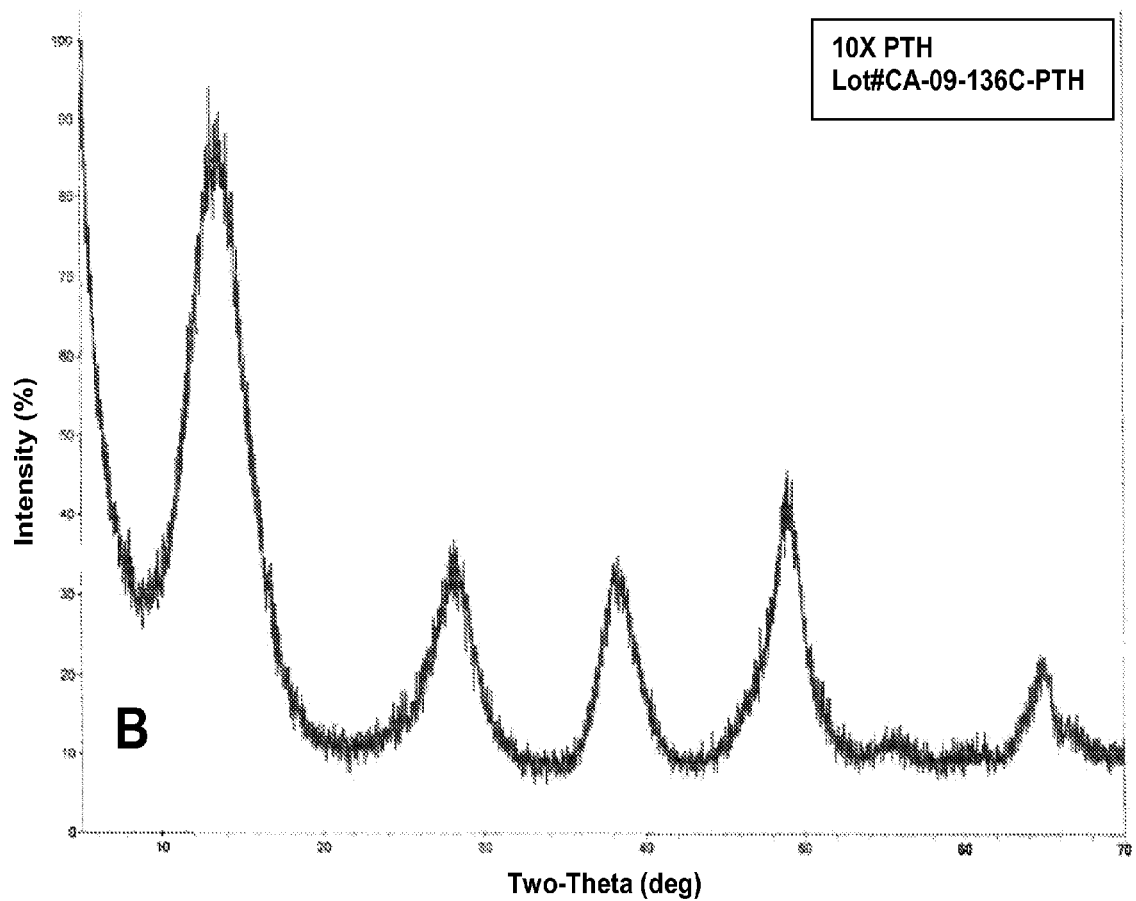
Figure 9C:
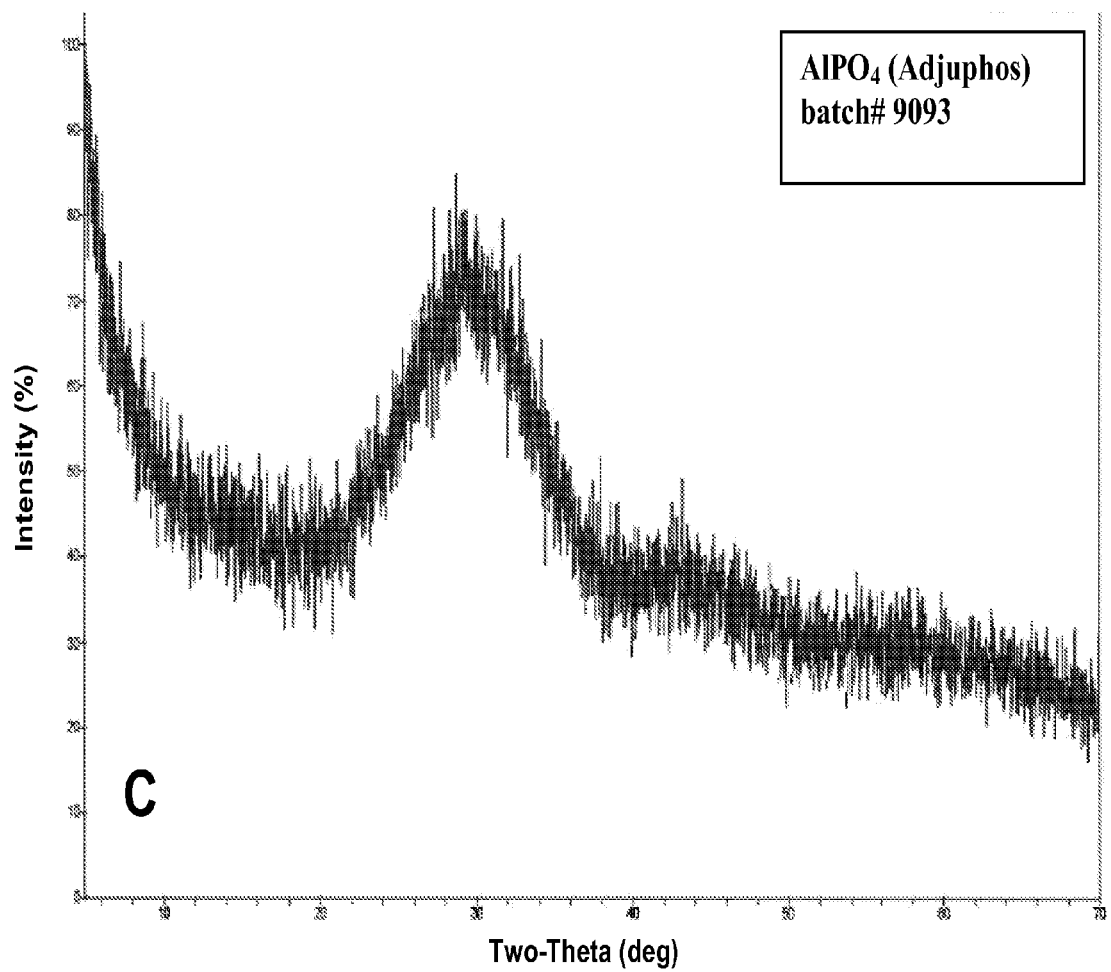
Figure 10A:
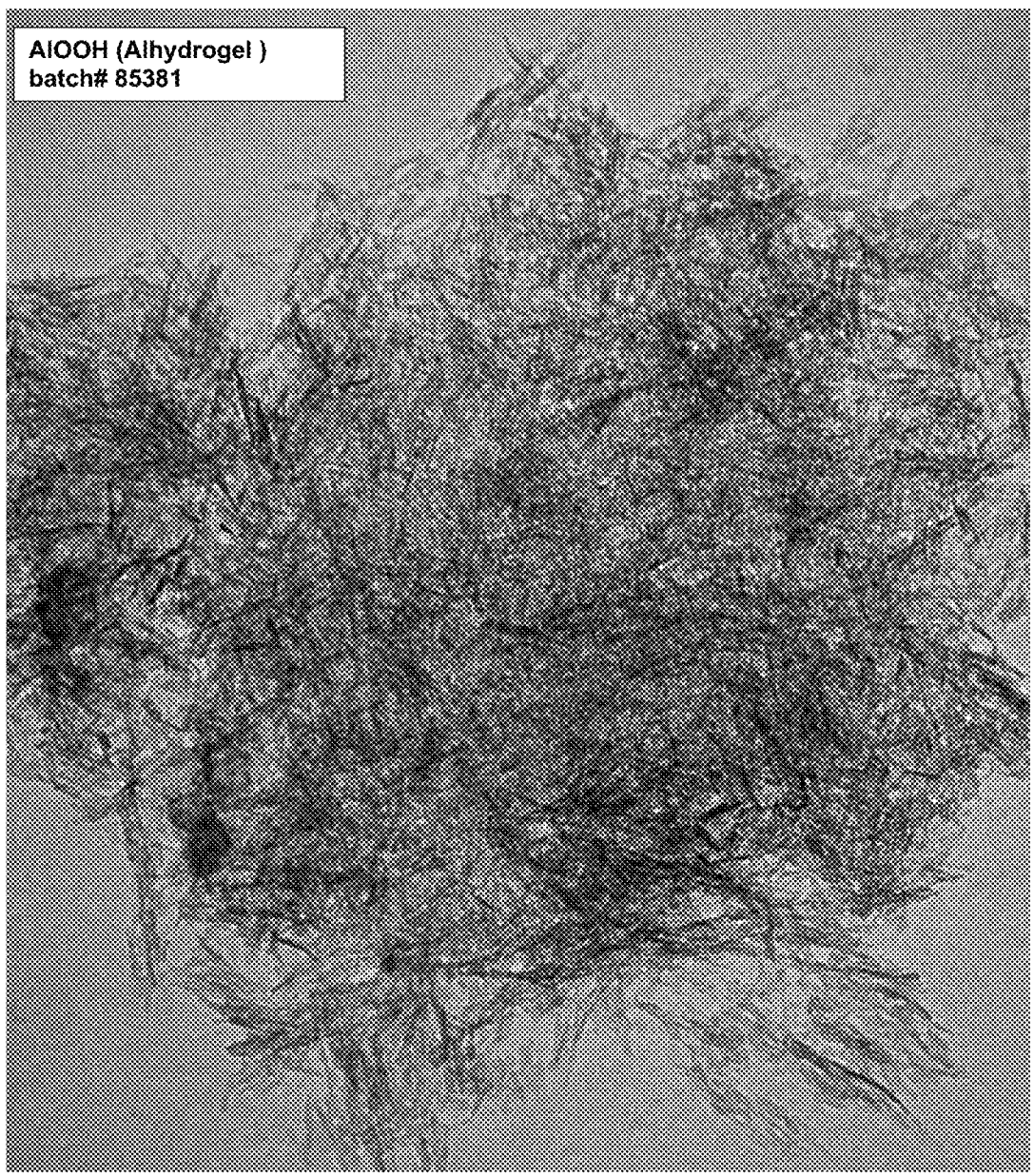
Figure 10B:
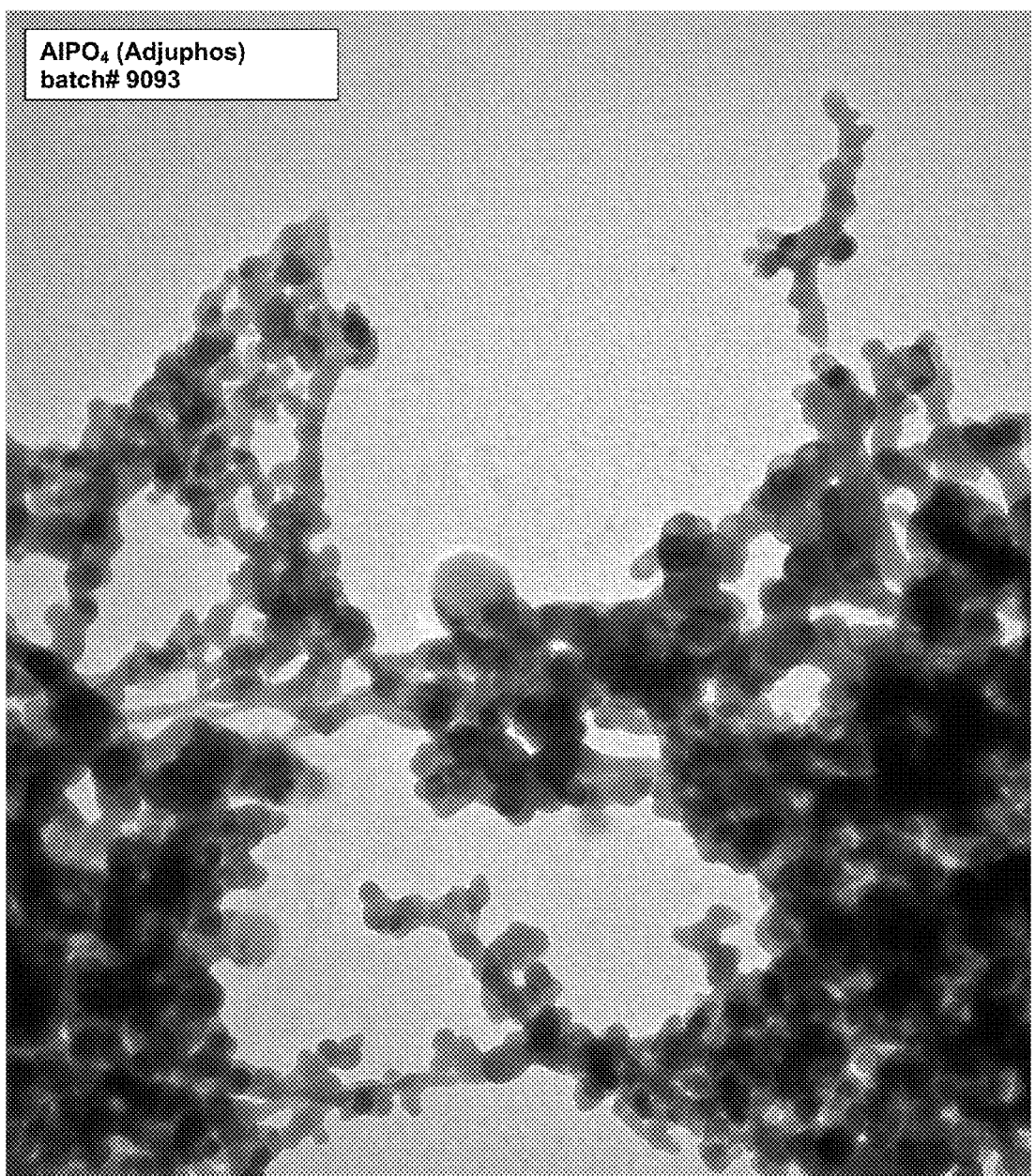
Figure 10C:
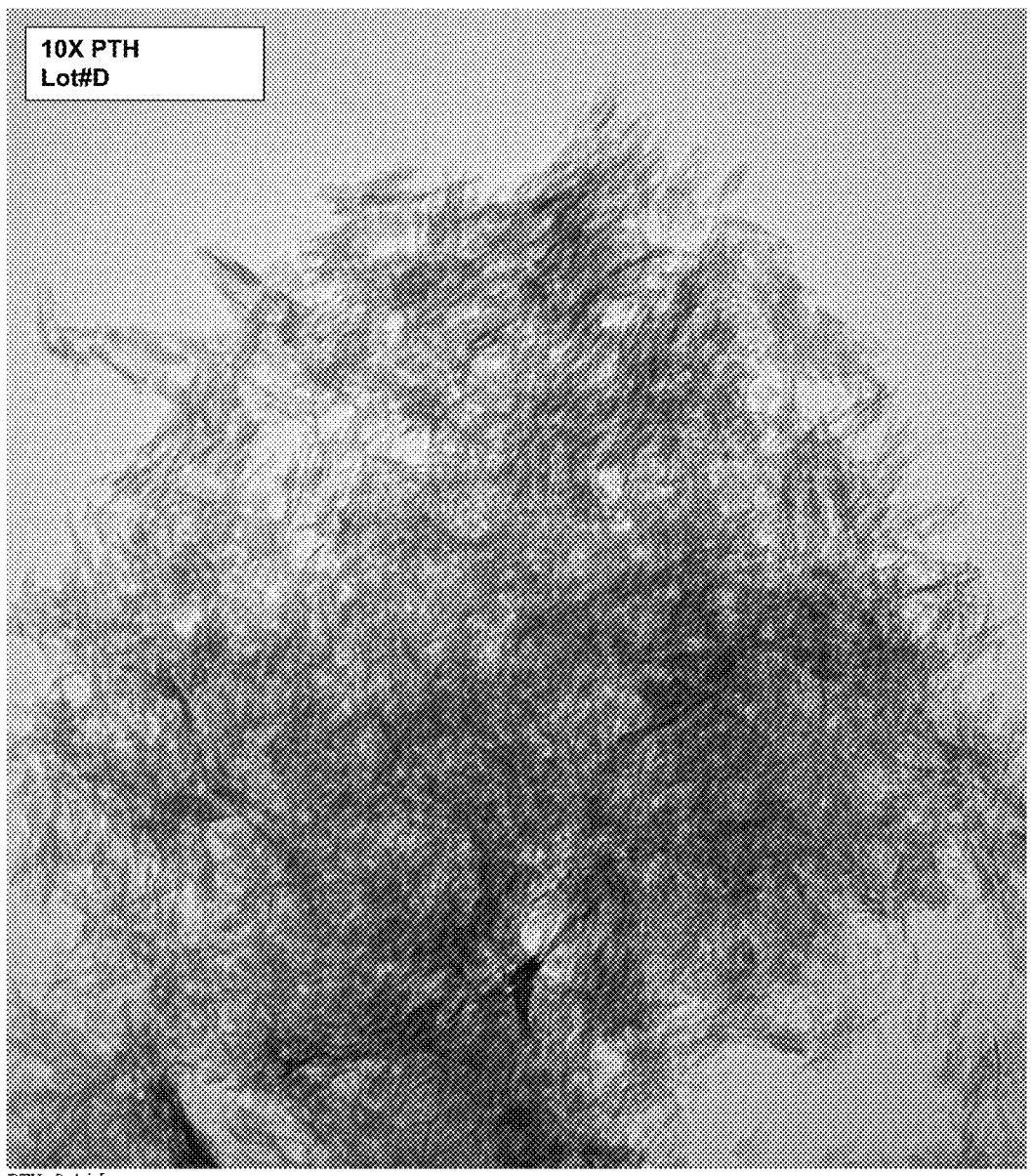
Figure 10D:
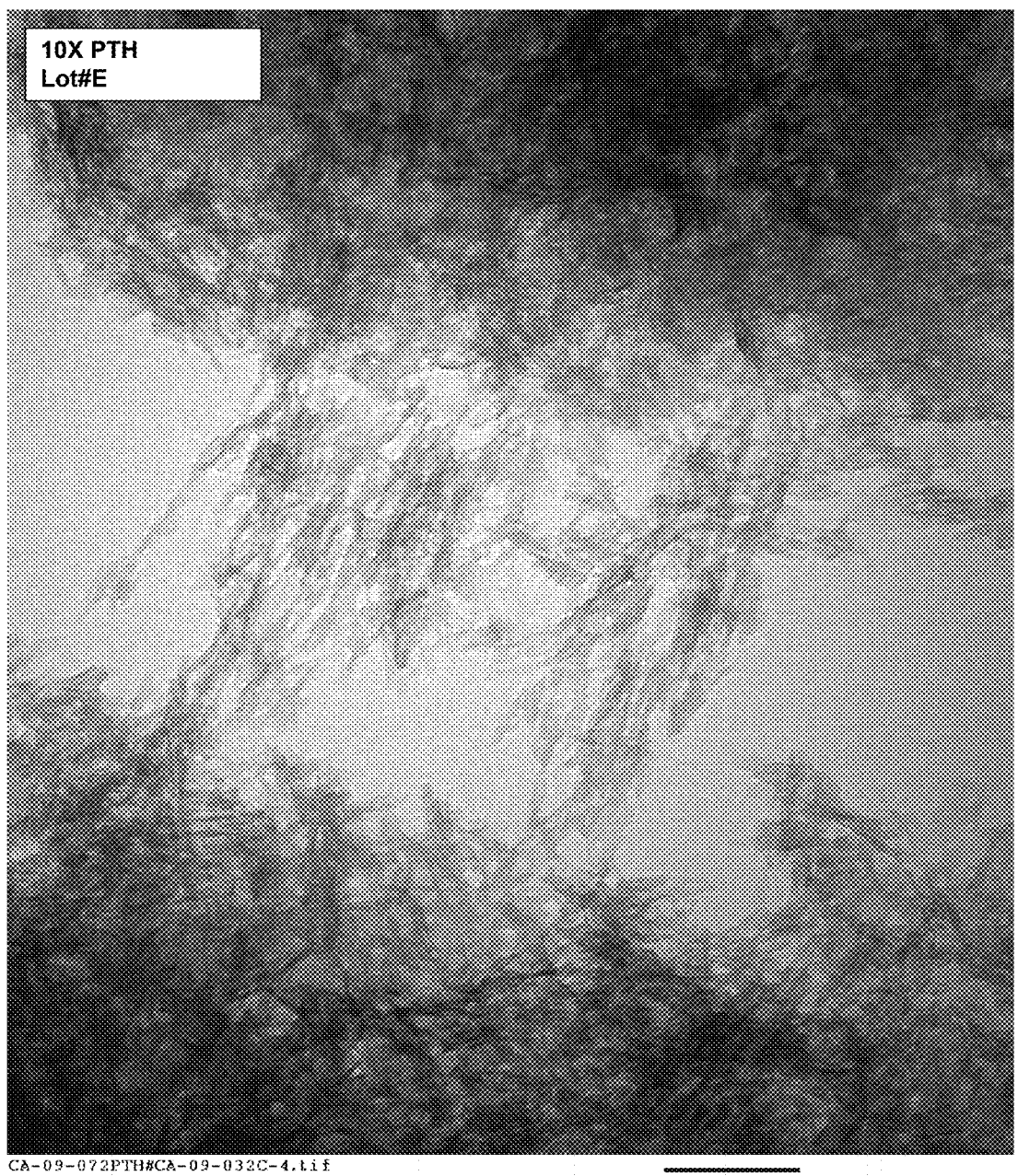

FIG. 9. X-ray diffraction patterns of different lots of AlOOH (A), PTH (B) and $AlPO_4$ (C).

FIG. 10. TEM analysis of AlOOH (Alhydrogel® (A)), $AlPO_4$ (Adjuphos® (B)), and PTH (C and D).

FIG. 11. Effect of pH on the physical stability of adjuvanted proteins. PcpA (A), PhtD (B) and PlyD1 (C) were adjuvanted with aluminum hydroxide or aluminum phosphate at different pH values and the Tm values were obtained by derivative analysis of the fluorescence traces.

FIG. 12A Studies of excipient effects on the stability of PcpA (stored at 50° C. for three days) in the presence of 10% sorbitol (■), 10% trehalose (●), 10% sucrose (Δ), TBS pH 9.0 (♦), and TBS pH 7.4 (○) by RP-HPLC.

FIG. 12B Studies of excipient effects on the antigenicity of PcpA (stored at 50° C. for three days) in the presence of 10% sorbitol, 10% trehalose, 10% sucrose, TBS pH 9.0, and TBS pH 7.4 by quantitative ELISA sandwich. Formulations were stored at 50° C. for three days. Antigenicity was evaluated for each formulation at time zero (white bars) and following three day storage (black bars).

DETAILED DESCRIPTION OF INVENTION

The present invention is directed to methods of preparing a stable formulation of an immunogenic composition comprising an antigen and an aluminum compound comprising hydroxide groups. The methods comprise adding to the aluminum compound ions, such as for example, those of phosphate, carbonate, carboxylate, sulfate, diphosphonate, or fluoride, or a mixture of these ions in amounts sufficient to stabilize the antigen. Immunogenic compositions comprising an antigen and an aluminum compound comprising hydroxide groups and methods of using these compositions for preventing and treating particular diseases are also provided.

The term "antigen" as used herein refers to a substance that is capable of initiating and mediating the formation of a corresponding immune body (antibody) when introduced into a mammal. An antigen may possess multiple antigenic determinants such that the exposure of the mammal to an antigen may produce a plurality of corresponding antibodies with differing specificities.

Antigens may include, but are not limited to proteins, peptides, polypeptides, nucleic acids, and fragments, variants and combinations thereof. Antigens may also include larger components, such as all or parts of cells, bacteria, viruses and other microorganisms and part or combinations of these. Bacteria and viruses, particularly those responsible for diseases in mammals are sources of antigens useful in the present invention. Bacterial antigens include proteins or polysaccharides derived from the outer surfaces of the cell, from the cell interior, or from the flagella. Other antigens may be those secreted by an infected cell or released upon cell death or disruption. Examples of such antigens include diphtheria, tetanus, and botulism toxins. Particular examples of antigens which may be incorporated into the practice of the present invention include but are not limited to diphtheria antigens, tetanus antigens, human papilloma virus antigens, anthrax antigens, E. coli antigens, rabies antigens and influenza antigens, Streptococcus pneumoniae antigens, type C meningococcal antigens, type A meningococcal antigens, HIV antigens, malaria antigens, herpes simplex virus antigens, measles antigens, measles-mumps-rubella antigens, yellow fever antigens, vericella antigens, Japanese Encephalitis virus antigens, Dengue antigens, rotavirus antigens, C. difficile antigens, P. gingivalis antigens, and Chlamydial antigens (e.g., C. trachomatis, C. pneumoniae).

The antigens employed in the present invention may be the naturally occurring form of the antigen as derived from its natural source. Due to toxicity, the antigen may be converted to a less toxic form or fragment which retains the ability to elicit an immune response against the native antigen. Diptheria toxoid and tetanus toxoid are examples of detoxified forms of the native antigen generally produced by chemical treatment (e.g., formaldehyde). Other means for eliminiating toxicity of antigens are well known in the art and include for example, enzymatic digestion/fragmentation of protein antigens, denaturation (commonly through heat or chemical treatment), conjugation, chemical modification and genetic detoxification. Detoxified pneumolysin proteins of S. pneumoniae suitable for use in the present invention include those described in WO2010/071986. A preferred detoxified pneumolysin protein for use in the present invention is PlyD1 (SEQ ID NO:9).

Antigens employed in the present invention may also be in the form of a fusion protein. As used herein, a fusion polypeptide is one that contains a polypeptide or a polypeptide derivative of the invention fused at the N- or C-terminal end to any other polypeptide (hereinafter referred to as a peptide tail). A simple way to obtain such a fusion polypeptide is by translation of an in-frame fusion of the polynucleotide sequences, i.e., a hybrid gene. The hybrid gene encoding the fusion polypeptide is inserted into an expression vector which is used to transform or transfect a host cell. Alternatively, the polynucleotide sequence encoding the polypeptide or polypeptide derivative is inserted into an expression vector in which the polynucleotide encoding the peptide tail is already present. Such vectors and instructions for their use are commercially available, e.g. the pMal-c2 or pMal-p2 system from New England Biolabs, in which the peptide tail is a maltose binding protein, the glutathione-S-transferase system of Pharmacia, or the His-Tag system available from Novagen. These and other expression systems provide convenient means for further purification of polypeptides and derivatives of the invention.

An advantageous example of a fusion polypeptide is one where the polypeptide or homolog or fragment of the invention is fused to a polypeptide having adjuvant activity, such as subunit B of either cholera toxin or E. coli heat-labile toxin. Another advantageous fusion is one where the polypeptide, homolog or fragment is fused to a strong T-cell epitope or B-cell epitope. Such an epitope may be one known in the art, or one which has been identified in another polypeptide of the invention based on computer-assisted analysis of probable T- or B-cell epitopes. Consistent with this aspect of the invention is a fusion polypeptide comprising T- or B-cell epitopes from SEQ ID Nos: 1,2,5,7,9, or 10 or its homolog or fragment, wherein the epitopes are derived from multiple variants of said polypeptide or homolog or fragment, each variant differing from another in the location and sequence of its epitope within the polypeptide. To effect fusion, the polypeptide of the invention is fused to the N-, or preferably, to the C-terminal end of the polypeptide having at least one T- or B-cell epitope. The T- or B-cell epitope may also be inserted internally within the amino acid sequence of the polypeptide of the invention.

Antigens of the present invention can be carrier proteins conjugated to an antigen such as bacterial polysaccharides. The conjugation of these polysaccharides can be performed by any of the known methods that exist in the art, for example WO2008/143709.

As mentioned above, the term "antigen" may include, but is not limited to proteins, peptides, polypeptides, nucleic acids and fragments, variants and combinations thereof. The terms "polypeptides", "peptide" and "protein" are used interchangeably herein to refer to a polymer of amino acid residues.

Antigens for use in the present invention can be produced using a variety of methods known to those of skill in the art. For example, antigens can be isolated directly for native sources, using standard purification techniques. Alternatively, antigens can be produced recombinantly using known techniques. Recombinantly produced antigens and variants or fragments of an antigen of interest, may be used in the present invention.

Antigens for use herein may also be synthesized via chemical polymer synthesis such as solid phase peptide synthesis. Such methods are known to those of skill in the art.

Variants and fragments of antigens comprising polypeptides are also encompassed by the present invention. "Variants" refer to substantially similar sequences. A variant of an amino acid or nucleotide sequence of the invention will typically have at least about 65%, 70%, 75%, 80%, 85%, 90%, 91%, 92%, 93%, 94%, 95%, 96%, 97%, 98%, 99% or more sequence identity with the reference sequence. In particular embodiments, a variant of an antigenic polypeptide of the invention will retain the biologically activity of the full-length polypeptide and hence be immunogenic. Methods for generating variant sequences are well known in the art are as methods for determining percent identity of polypeptide or polynucleotide sequences.

The term "fragment" refers to a portion of a polypeptide or polynucleotide comprising a specified number of contiguous amino acid or nucleotide residues. In particular embodiments a fragment of an immunogenic polypeptide of the invention may retain the biological activity of the full length polypeptide and hence be immunogenic. Fragments of a polynucleotide may encode protein fragments that retain the biological activity of the protein and hence be immunogenic. Fragments of the polypeptides and polynucleotides of the invention can be of any length provided they have the desired attributes (e.g. immunogenicity). Methods for generating fragments of a polypeptide or a polynucleotide are known in the art.

Antigens of the present invention from Streptococcus pneumoniae can be selected from the group consisting of (but not limited to) the Polyhistidine Triad family (PhtX: PhtA,B,D,E), Choline Binding Protein family (CbpX), LytX family, pneumolysin (Ply), PspA, PsaA, and PcpA.

PcpA polypeptides comprise the full-length PcpA amino acid sequence (in the presence or absence of the signal sequence), fragments thereof, and variants thereof. PcpA polypeptides suitable for use in the compositions described herein include, for example, those of GenBank Accession No. CAB04758 from S. pneumoniae strain B6, GenBank Accession No. NP_from S. pneumoniae strain TIGR4 and GenBank Accession No. NP_359536 from *S. pneumoniae* strain R6, and those from *S. pneumoniae* strain 14453. The amino acid sequence of full length PcpA in the *S. pneumoniae* 14453 genome is SEQ ID NO. 2. A preferred PcpA polypeptide is SEQ ID NO:7.

PhtX polypeptides suitable for the compositions of the invention comprise the full-length PhtA, PhtB, PhtD or PhtE amino acid sequence (in the presence or absence of the signal sequence), immunogenic fragments thereof, variants thereof and fusion proteins thereof. PhtD polypeptides suitable for use in the compositions described herein include, for example, those of GenBank Accession Nos. AAK06760, YP816370 and NP35851, among others. The amino acid sequence of full length PhtD in the *S. pneumoniae* 14453 genome is SEQ ID NO:1. A preferred polypeptide of PhtD (derived from the *S. pneumonaie* 14453 genome) is SEQ ID NO:5.

Pneumolysin (Ply) is a cytolytic-activating toxin implicated in multiple steps of pneumococcal pathogenesis, including the inhibition of ciliary beating and the disruption of tight junctions between epithelial cells (Hirst et al. Clinical and Experimental Immunology (2004)). Several pneumolysins are known and (following detoxification) would be suitable for use in the compositions described herein including, for example GenBank Accession Nos. Q04IN8, P0C2J9, Q7ZAK5, and ABO21381, among others. In one embodiment, Ply has the amino acid sequence shown in SEQ ID NO.10.

The pneumolysin polypeptides of the present invention are preferably detoxified; that is, they lack or have reduced toxicity as compared to the mature wild-type pneumolysin protein produced and released by *S. pneumoniae*. The pneumolysin polypeptides of the present invention may be detoxified for example, chemically (e.g., using formaldehyde treatment) or genetically (e.g., recombinantly produced in a mutated form). Preferred examples of the detoxified pneumolysin for use in the present invention are disclosed in PCT Publication No. WO 2010/071986. As disclosed in that application, the detoxified pneumolysin may be a mutant pneumolysin protein comprising amino acid substitutions at positions 65, 293 and 428 of the wild type sequence. In a preferred detoxified pneumolysin protein, the three amino acid substitutions comprise T65→C, G293→C, and C428→A. A preferred immunogenic and detoxified pneumolysin polypeptide is SEQ ID NO:9.

As used herein, "immunogenicity" refers to the ability of a substance to induce an immune response when administered to a subject (e.g., a cellular immunogen-specific immune response and/or a humoral antibody response). As used herein and defined in the art, "antigenicity" is the ability of an antibody to recognize and bind to a protein (e.g., an antigen).

The term "adjuvant" as used herein refers to agents which are administered to a subject in conjunction with an antigen to enhance the immunogenicity of the antigen.

Aluminum salt adjuvants (or compounds) are among the adjuvants of use in the practice of the invention. In particular, aluminum hydroxide (e.g., crystalline aluminum oxyhydroxide AlO(OH), and aluminum hydroxide Al(OH)$_3$) is of use. Aluminum hydroxide is an aluminum compound comprising Al$^{3+}$ ions and hydroxyl groups (—OH). Mixtures of aluminum hydroxide with other aluminum compounds (e.g., hydroxyphosphate or hydroxysulfate) may also be of use where the resulting mixture is an aluminum compound comprising hydroxyl groups. It is well known in the art that compositions with aluminum salt adjuvants should not be exposed to extreme temperatures, i.e. below freezing (0° C.) or extreme heat (e.g., ≥70 ° C.) as such exposure may adversely affect the stability and the immunogenicity of both the adsorbed antigen and adjuvant.

In particular embodiments, the aluminum adjuvant is aluminum oxyhydroxide (e.g., Alhydrogel®).

In a particular embodiment of the invention, the aluminum compound comprising hydroxyl groups (e.g., aluminum hydroxide adjuvant) is treated with phosphate, carbonate, sulfate, carboxylate, diphosphonate, or fluoride or a mixture of two or more of these compounds. By treating the aluminum compound in this way a number of the hydroxyl groups (—OH) in the aluminum compound are replaced with the corresponding ion with which it is being treated (e.g., phosphate (PO$_4$)). This replacement lowers the PZC of the aluminum compound and the pH of the compound's microenvironment. The phosphate, carbonate, sulfate, carboxylate, diphosphonate or fluoride ions are added in an amount sufficient to lower the pH of the microenvironment to a level at which the antigen is stabilized (i.e., the rate of antigen hydrolysis is decreased). The amount necessary will depend on a number of factors such as, for example, the antigen involved, the antigen's isoelectric point, the antigen's concentration, the interaction forces between antigen and adjuvant, the adjuvanting method utilized, and the amount and nature of any additional antigens present in the formulation. Those skilled in the art in the field of vaccines are capable of assessing the relevant factors and determining the concentration of phosphate, carbonate, sulfate, carboxylate, diphosphonate, fluoride to add to the aluminum compound to increase the stability of the antigen (and therefore, can prepare the corresponding formulation and composition). For example, titration studies (i.e., adding increasing concentrations of phosphate, etc., to aluminum compound) may be performed.

Phosphate compounds suitable for use include any of the chemical compounds related to phosphoric acid (such as for example, inorganic salts and organic esters of phosphoric acid). Phosphate salts are inorganic compounds containing the phosphate ion (PO$_4^{3-}$), the hydrogen phosphate ion (HPO$_4^{2-}$) or the dihydrogen phosphate ion (H$_2$PO$^{4-}$) along with any cation. Phosphate esters are organic compounds in which the hydrogens of phosphoric acid are replaced by organic groups. Examples of compounds that may be used in place of phosphate salts include anionic amino acids (e.g., glutamate, aspartate) and phospholipids.

Carboxylate compounds suitable for use include any of the organic esters, salts and anions of carboxylic acids (e.g., malic acid, lactic acid, fumaric acid, glutaric acid, EDTA, and EGTA). Sulfur anions suitable for use include any compound containing the sulfate (SO$_4$ radical) such as salts or esters of sulfuric acid (e.g., sodium sulfate, ammonium sulfate, sulfite, metabisulfite, thiosulfate). Examples of disphosphonate compounds suitable for use include clodronate, pamidronate, tiludronate, and alendronate.

In a preferred embodiment of the invention, phosphate is added to aluminum hydroxide adjuvant in the form of a salt. Preferably, the phosphate ions are provided by a buffer solution comprising disodium monosodium phosphate.

In the preferred practice of the present invention, as exemplified herein, the aluminum compound (e.g., aluminum oxyhydroxide) is treated with phosphate (for example, by a process as described in the examples). In this process, an aqueous suspension of aluminum oxyhydroxide (approximately 20 mg/mL) is mixed with a phosphate buffer solution (e.g., approximately 400 mmol/L). The preferable final phosphate concentration is from about 2 mM to 20 mM. The mixture is then diluted with a buffer (e.g., Tris-HCl, Tris- HCl with saline, HEPES) to prepare a suspension of aluminum oxyhydroxide and phosphate ($PO_4$). Preferably the buffer is 10 mM Tris-HCl and 150 mM NaCl at a pH of about 7.4. The suspension is then mixed for approximately 24 hr at room temperature. Preferably the concentration of elemental aluminum in the final suspension is within a range from about 0.28 mg/mL to 1.68 mg/mL. More preferably, the concentration of elemental aluminum is about 0.56 mg/mL.

Antigens (individually or in combination) may then be adsorbed to the treated aluminum hydroxide. Preferably, approximately 0.2-0.4 mg/mL of antigen is mixed with the suspension of treated aluminum oxyhydroxide (e.g., at room temperature or at 2-8° C., in an orbital mixer, for approximately 30 min, or approximately 12-15 hours, or approximately 24 hours).

In one example, immunogenic polypeptides of PcpA, PhtX (e.g., PhtD) and a detoxified mutant of Pneumolysin (individually or in combination) may then be adsorbed to the treated aluminum hydroxide. Preferably, approximately 0.2-0.4 mg/mL of each antigen is mixed with the suspension of treated aluminum hydroxide adjuvant (e.g., at room temperature or at 2-8° C., in an orbital mixer, for approximately 30 min or approximately 12-15 hours, or approximately 24 hours).

The percentage of antigen adsorption may be assessed using standard methods known in the art. For example, an aliquot of the antigen/adjuvant preparation may be removed and centrifuged (e.g., at 10,000 rpm) to separate the unadsorbed protein (pellet) from the adjuvant suspension (supernatant). The concentration of protein in the supernatant may be determined using the bicinchoninic acid protein assay (BCA) or reverse phase- high performance liquid chromatography (RP-HPLC). The percentage of adsorption is calculated as follows: %A=100−([PrSN]×100/[PrCtr]) where, [PrSN] is the concentration of protein in supernatant and [PfCtr] is the concentration in the corresponding unadjuvanted control. In preferred embodiments, the % adsorption ranges from about 70% to about 100%. In more preferred embodiments the % adsorption is at least about 70%.

The disclosed formulations are stable when stored for prolonged time periods at conventional refrigeration temperatures, e.g., about 2 ° C. to about 8° C. The formulations exhibit little or no particle agglomeration, no significant decrease in antigen concentration or a reduced rate of antigen degradation and retain a significant level of immunogenicity and/or antigenicity for at least 6 months or 12 months and preferably for 18 months. The phrase "no significant decrease in antigen concentration" is intended to mean that the composition retains at least 50%, 60%, or 70% of the original antigen concentration, more preferably at least about 80%, 85%, or 90% of the original antigen concentration, more preferably at least about 91%, 92%, 93%, 94%, 95%, 96%, 97%, 98%, 99% or more of the antigen concentration present when first formulated. Antigen concentration may be measured, for example, by an RP-HPLC, SDS-PAGE or ELISA-based method.

A stable formulation or an immunogenic composition comprising a stable formulation maintains a substantial degree of structural integrity (e.g., maintains a substantial amount of the original antigen concentration, etc.).

Stability may be assessed by measuring for example, the concentration of antigen present (e.g, by RP-HPLC) or by assessing antigen degradation for example by SDS-PAGE analysis. The antigen concentration in the formulation may be compared with that of the formulation as prepared with the same aluminum compound albeit untreated (e.g., not treated with phosphate or carbonate ions). Stability prediction and/or comparison tools include for example, Stability System™ (by ScienTek Software, Inc.), which use Arrhenius Treatment to predict rate constant at storage temperature (2° C.-8° C.). Standard assays for measuring the antigen concentration, and immunogenicity are known in the art and are described in the Examples. Protective efficacy may be assessed by for example evaluating the survival rates of immunized and non-immunized subjects following challenge with a disease causing pathogen or toxin corresponding to the particular antigen present in the formulation.

The stability of, for example, S. pneumoniae proteins such as PcpA, PhtX (e.g., PhtD) and pneumolysin (e.g., detoxified pneumolysin, PlyD1) may be improved by adjuvanting these polypeptides (individually or in combination) with a treated aluminum compound comprising hydroxyl groups as opposed to adjuvanting with a corresponding untreated aluminum compound comprising hydroxyl groups. The degradation rate of these polypeptides when adjuvanted with aluminum hydroxide adjuvant (AlO(OH)) is high (as discussed in the Examples below). The inventors have found that adjuvanting these polypeptides (e.g., PcpA, PhtD) with an aluminum compound comprising hydroxyl groups (e.g., aluminum hydroxide) that has been pretreated with phosphate (or e.g., carbonate, sulfate, carboxylate, diphosphonate or a mixture of two or more of these compounds) increases the stability of these polypeptides (e.g., by decreasing antigen degradation) relative to adjuvanting them with a corresponding untreated aluminum compound. Thus, provided herein are formulations of compositions comprising an immunogenic PcpA polypeptide and/or an immunogenic PhtX polypeptide (e.g., PhtD) and/or pneumolysin (e.g., detoxified pneumolysin; PlyD1 (SEQ ID NO:9)) and an aluminum compound comprising hydroxyl groups that has been treated with phosphate, carbonate, sulfate, carboxylate, diphosphonate or a mixture of two or more of these compounds, where the treatment increases the stability of the immunogenic polypeptide relative to a composition where the polypeptide is adsorbed to an untreated aluminum compound comprising hydroxyl groups. In preferred embodiments the aluminum compound is treated with phosphate. Multivalent compositions adjuvanted with such a treated aluminum compound and comprising the immunogenic polypeptides of PcpA and PhtX (e.g., PhtD) or comprising pneumolysin (e.g., detoxified pneumolysin; PlyD1) and PcpA and PhtX (e.g., PhtD) polypeptides are also provided.

The immunogenic composition is preferably in liquid form, but it may be lyophilized (as per standard methods) or foam dried (as described in WO2009012601, Antigen-Adjuvant Compositions and Methods). A composition according to one embodiment of the invention is in a liquid form. An immunization dose may be formulated in a volume of between 0.5 and 1.0 ml. Liquid formulations may be in any form suitable for administration including for example, a solution, or suspension. Thus, the composition can include a liquid medium (e.g., saline or water) which may be buffered.

The pH of the formulation (and composition) is preferably between about 6.4 and about 8.4. More preferably, the pH is about 7.4. An exemplary pH range of the formulation is 5-10, (e.g., 5-9, 5-8, 5.5-9, 6-7.5, or 6.5-7). The pH may be maintained by the use of a buffer.

The pharmaceutical formulations of the immunogenic compositions of the present invention may also optionally include one or more excipients (e.g., diluents, thickeners, buffers, preservatives, surface active agents, adjuvants, detergents and/or immunostimulants) which are well known in the art. Suitable excipients will be compatible with the antigen and with the aluminum adjuvant as is known in the art. Examples of diluents include binder, disintegrants, or dispersants such as starch, cellulose derivatives, phenol, polyethylene glycol, propylene glycol or glycerin. Pharmaceutical formulations may also include one or more active ingredients such as antimicrobial agents, antiinflammatory agents and anesthetics. Examples of detergents include a Tween (polysorbate) such as Tween 80. Preferably, the antigen(s) adsorbed to the treated aluminum compound are purified before being combined with one or more pharmaceutically acceptable excipients.

A composition according to one embodiment of the invention may be prepared by (i) treating an aluminum compound comprising hydroxyl groups with phosphate, carbonate, sulfate, carboxylate, diphosphonate, or a mixture of two or more of these compounds, and (ii) mixing the treated aluminum compound with at least one antigen. In preferred embodiments (as described in the Examples), the antigens include (but are not limited to), PcpA, PhtX (e.g., PhtD) and detoxified pneumolysin (such as e.g., PlyD1, SEQ ID NO:9), individually or in combination.

Also provided are formulations including PcpA, PhtX (e.g., PhtD) and/or detoxified pneumolysin (individually or in combination) adjuvanted with an aluminum compound comprising hydroxyl groups (e.g. aluminum hydroxide) that has been treated in accordance to the present invention (e.g., with phosphate) and including one or more pharmaceutically acceptable excipients that provide beneficial properties to the compositions (e.g., increase the stability of one or more of the proteins of the compositions). In one example, the formulations include a phosphate treated aluminum hydroxide (PTH). The compounds or excipients that can be included in the compositions of the invention include for example, buffers (e.g., glycine, histidine); tonicity agents (e.g, mannitol); carbohydrates, such as sugars or sugar alcohols (e.g., sorbitol, trehalose, or sucrose; 1-30%) or carbohydrate polymers (e.g., dextran); amino acids, oligopeptides or polyamino acids (up to 100 mM); polyhydric alcohols (e.g., glycerol, and concentrations of up to 20%); detergents, lipids, or surfactants (e.g., Tween 20, Tween 80, or pluronics, with concentrations of up to 0.5%); antioxidants; salts (e.g., sodium chloride, potassium chloride, magnesium chloride, or magnesium acetate, up to 150 mM); or combinations thereof.

Examples of excipients that can be used include those that are listed in Table 13, and the examples below. In various examples, the excipients may be those that result in increased thermal stability (e.g., of at least 0.5, e.g., 0.5-5, 1-4, or 2-3) as measured by, e.g., the assays described below (e.g., extrinsic fluorescence of SYPRO Orange).

Exemplary excipients and buffers include sorbitol (e.g., 4-20%, 5-10%), (see Table 13). These excipients can be used in the concentrations listed in Table 13. Alternatively, the amounts can be varied by, e.g., 0.1-10 fold, as is understood in the art. Other carbohydrates, sugar alcohols, surfactants and amino acids that are known in the art can also be included.

The excipients and buffers can be used individually or in combination. The pH of such a composition can be, e.g., 5.5-8.0 or 6.5-7.5, and the composition can be stored at, e.g., 2-8° C., in liquid or lyophilized form. In variations of the composition, the sorbitol can be replaced with sucrose (e.g., 4-20%, or 5-10%), or trehalose (e.g., 4-20%, or 5-10%). Other variations of the compositions are also possible and involve use of other components listed herein. Based on the above, an exemplary formulation of PcpA, PhtD and detoxified pneumolysin (individually or in combination) includes 10% sorbitol, pH 7.4.

In one embodiment, a monovalent PlyD1 (SEQ ID NO:9) composition may include per dose, in the range of 5 to 50 µg of antigen, PTH adjuvant (with about 0.56 mg/mL elemental Aluminum containing 2 mM sodium phosphate buffer at about pH 7.5), in about: 10 mM Tris HCl, and about 150 mM NaCl, at about pH 7.4. In preferred examples, PlyD1 is in the range of 25 to 50 µg/dose.

In another embodiment, a monovalent PhtD composition may include per dose, in the range of 5 to 50 µg of antigen, PTH adjuvant (with about 0.56 mg/mL elemental Aluminum containing 2 mM sodium phosphate buffer at about pH 7.5), in about: 10 mM Tris HCl, and about 150 mM NaCl, at about pH 7.4. In preferred examples, PhtD is in the range of 25 to 50 µg/dose.

In a further embodiment, a monovalent PcpA composition may include per dose, in the range of 5 to 50 µg of antigen, PTH adjuvant (with about 0.56 mg/mL elemental Aluminum containing 2 mM sodium phosphate buffer at about pH 7.5), in about: 10 mM Tris HCl, and about 150 mM NaCl, at about pH 7.4. In preferred examples, PcpA is in the range of 25 to 50 µg/dose.

In another embodiment, a bivalent formulation composition may include per dose, two proteins (selected from the following: PhtD, PlyD1 or PcpA), each in the range of 5 to 50 µg/dose, PTH adjuvant (with about 0.56 mg/mL elemental Aluminum containing 2 mM sodium phosphate buffer at about pH 7.5), in about: 10 mM Tris HCl, and about 150 mM NaCl, at about pH 7.4. In certain examples, the two antigens are present in a 1:1 antigen/dose ratio. In yet a further embodiment, a trivalent formulation composition can include per dose, three proteins (PhtD, PlyD1, PcpA), each in the range of 5 to 50 µg/dose, PTH adjuvant (with about 0.56 mg/mL elemental Aluminum containing 2 mM sodium phosphate buffer at about pH 7.5), in about: 10 mM Tris HCl, and about 150 mM NaCl, at about pH 7.4. In certain examples, the amount (antigen/dose) of each of the three antigens is in a ratio of about 1:1:1.

In another example, the compositions include sorbitol, or sucrose, which have been shown to provide benefits with respect to stability (see below). The amounts of these components can be, for example, 5-15%, 8-12% or 10% sorbitol or sucrose. A specific example in which these components are present at 10% is described below. In a preferred embodiment, the compositions include 10% sorbitol or 10% sucrose.

The immunogenic compositions of the invention find use in methods of preventing or treating a disease, disorder condition or symptoms associated with a particular antigen. The terms disease disorder and condition will be used interchangeably herein. Specifically the prophylactic and therapeutic methods comprise administration of a therapeutically effective amount of a pharmaceutical composition to a subject. In particular embodiments, methods for preventing or treating *S. pneumoniae* are provided.

As used herein, preventing a disease or disorder is intended to mean administration of a therapeutically effective amount of a pharmaceutical composition of the invention to a subject in order to protect the subject from the development of the particular disease or disorder associated with the antigen.

By treating a disease or disorder is intended administration of a therapeutically effective amount of a pharmaceutical composition of the invention to a subject that is afflicted with the disease or that has been exposed to a pathogen that causes the disease where the purpose is to cure, heal, alleviate, relieve, alter, remedy, ameliorate, improve, or affect the condition or the symptoms of the disease.

A therapeutically effective amount refers to an amount that provides a therapeutic effect for a given condition and administration regimen. A therapeutically effective amount can be determined by the ordinary skilled medical worker based on patient characteristics (age, weight, gender, condition, complications, other diseases, etc.). The therapeutically effective amount will be further influenced by the route of administration of the composition.

The compositions of the invention can be administered to a subject by a variety of methods known in the art. Any method for administering a composition to a subject may be used in the practice of the invention.

Definitions

The term "comprising" encompasses "including" as well as "consisting" (e.g., a composition "comprising" X may consist exclusively of X or may include something additional, e.g., X+Y).

The term "substantially" does not exclude "completely" (e.g., a composition which is "substantially free" from Y may be completely free from Y.

The term "about" in relation to a numerical value x means, for example x±10%.

The term "immunogen" is a substance that is able to induce an adaptive immune response.

The term "subject" encompasses species such as for example, mammals (e.g., a human or an animal (e.g., mouse, dog, cat, horse, sheep, pig, etc.); birds.

Unless specifically stated, a process comprising a step of mixing two or more components does not require any specific order of mixing. Thus components can be mixed in any order. Where there are three components then two components can be combined with each other, and then the combination may be combined with the third component, etc.

It will be appreciated that ionisable groups may exist in the neutral form as shown herein, or may exist in charged form e.g. depending on pH.

All references cited within this disclosure are hereby incorporated by reference in their entirety.

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Methods of molecular genetics, protein biochemistry, immunology and fermentation technology used, but not explicitly described in this disclosure and these Examples, are amply reported in the scientific literatures and are well within the ability of those skilled in the art.

Example 1

This Example describes the preparation of a surface modified adjuvant and formulations with this adjvuant. A surface modified adjuvant was prepared by treating aluminum hydroxide adjuvant (Alhydrogel™, Brenntag) with phosphate. The aluminum hydroxide adjuvant used was a wet gel suspension which according to the manufacturer tolerates re-autoclavation but is destroyed if frozen. According to the manufacturer, when the pH is maintained at 5-7, the adjuvant has a positive charge and can adsorb negatively charged antigens (e.g., proteins with acidic isoelectric points when kept at neutral pH).

a) Phosphate treatment of AlO(OH)—An aqueous suspension of AlO(OH) (approximately 20 mg/mL) was mixed with a stock solution of phosphate buffer (approximately 400 mmol/L) and diluted with 10 mM Tris-HCL buffer (Sigma Aldrich) at about pH 7.4 to prepare a phosphate-treated AlO(OH) suspension (herein referred to as "PTH") having approximately 13 mg/mL AlOOH/200 mM $PO_4$. This suspension was then mixed for approximately 30 minutes to 24 hr at room temperature.

b) Preparation of the PcpA protein and PhtD protein recombinantly—In brief, two recombinantly-derived protein antigens from *Streptococcus pneumoniae* (serotype 6 strain 14453, deposited on Jun. 27, 1997 as ATCC 55987), PhtD (WO2009/012588) and PcpA (WO 2008/022302) were recombinantly expressed in *E. coli*, isolated and purified by serial column chromatography following conventional purification protocols.

More specifically, the phtD gene (but excluding its native signal peptide) was PCR amplified from the *S. pneumoniae* 14453 genome (serotype 6 strain, deposited on Jun. 27, 1997 as ATCC 55987), a mouse-virulent capsule serotype 6B strain, using the AccuPrime High Fidelity polymerase (Invitrogen) and primers Spn0211 and Spn0213. Spn0211 and Spn0213 introduced NcoI and XhoI restriction sites into the 5' and 3' ends, respectively (see Table 1). The PCR product was purified using a QIAquick PCR purification kit (Qiagen) and run on an agarose gene to confirm the size. The PCT product and the pET28a(+) vector (Novagen) were both digested with NcoI and XhoI and subsequently purified from an agarose gel using the QIAEX gel extraction kit (Qiagen). The digested vector and gene were ligated together using T4 DNA ligase (Invitrogen). The ligation mixture was transformed into chemically competent *E. coli* DH5α and positive clones were selected by plating on Luria agar containing 50 μg/ml kanamycin. DNA from plasmid clone pBAC27 was isolated and was confirmed by sequencing to be correct.

The plasmid (pBAC27) was then introduced *E. coli* BL21 (DE3) cells by electroporation. Transformed strains were grown at approximately 37° C. and protein expression was induced by the addition of 1 mM IPTG. Expression of gene product was verified by the presence of an induced protein band of the correct size (i.e, approximately 91.9 kDa) by SDS-PAGE analysis.

TABLE 1

| Primer Name/ Number | Sequence 5' 3' |
|---|---|
| Spn0211 | CTAGCCATGGGATCCTATGAACTTGGTCGTCACCAAG (SEQ ID NO.: 11) |
| Spn0213 | AGTCCTCGAGCTACTGTATAGGAGCCGGTTG (SEQ ID NO.: 12) |

The predicted amino acid sequence of the polypeptide of pBAC27 is as follows:

(SEQ ID NO.: 5)
MGSYELGRHQAGQVKKESNRVSYIDGDQAGQKAENLTPDEVSKREGINA

EQIVIKITDQGYVTSHGDHYHYYNGKVPYDAIISEELLMKDPNYQLKDS

DIVNEIKGGYVIKVDGKYYVYLKDAAHADNIRTKEEIKRQKQEHSHNHN

SRADNAVAAARAQGRYTTDDGYIFNASDIIEDTGDAYIVPHGDHYHYIP

KNELSASELAAAEAYWNGKQGSRPSSSSSYNANPVQPRLSENHNLTVTP

TYHQNQGENISSLLRELYAKPLSERHVESDGLIFDPAQITSRTARGVAV

PHGNHYHFIPYEQMSELEKRIARIIPLRYRSNHWVPDSRPEQPSPQSTP

EPSPSLQPAPNPQPAPSNPIDEKLVKEAVRKVGDGYVFEENGVSRYIPA

KDLSAETAAGIDSKLAKQESLSHKLGAKKTDLPSSDREFYNKAYDLLAR

IHQDLLDNKGRQVDFEVLDNLLERLKDVSSDKVKLVDDILAFLAPIRHP

ERLGKPNAQITYTDDEIQVAKLAGKYTTEDGYIFDPRDITSDEGDAYVT

PHMTHSHWIKKDSLSEAERAAAQAYAKEKGLTPPSTDHQDSGNTEAKGA

EAIYNRVKAAKKVPLDRMPYNLQYTVEVKNGSLIIPHYDHYHNIKFEWF

DEGLYEAPKGYSLEDLLATVKYYVEHPNERPHSDNGFGNASDHVRKNKA

DQDSKPDEDKEHDEVSEPTHPESDEKENHAGLNPSADNLYKPSTDTEET

EEEAEDTTDEAEIPQVENSVINAKIADAEALLEKVTDPSIRQNAMETLT

GLKSSLLLGTKDNNTISAEVDSLLALLKESQPAPIQ

The pcpA gene (but excluding the signal sequence and the choline-binding domains) was PCR amplified from the *S. pneumoniae* 14453 genome using Accuprime Taq DNA polymerase (Invitrogen) and PCR primers (see Table 2) that incorporated restriction endonuclease sites designed for simplified cloning. Plasmid DNA of pET-30a(+) (Novagen) was purified as a low-copy plasmid and prepared for use as the cloning vector by digesting with NdeI and XhoI, followed by gel purification. The resulting 1335 base pair fragment was pcpA (without signal sequence and choline-binding domains) flanked by XhoI (3'-end) and NdeI (5'end) restriction sites. The amplified fragment was cleaned, digested with NdeI and XhoI and then gel purified and ligated into the pET-30a(+) vector. The insert was verified by sequencing and the new plasmid was designated pJMS87.

TABLE 2

| (Primers) | |
|---|---|
| Primer Name | Sequence 5' 3' |
| UAB 3 | TAGCCTCGAGTTAACCTTTGTCTTTAACCCAA CCAACTACTCCCTGATTAG (SEQ ID NO.: 11) |
| UAB-tagless 5 | CTAATGAACCACATATGGCAGATACTCCTAGT TCGGAAGTAATC (SEQ ID NO.: 12) |

The predicted amino acid sequence of the polypeptide of pJMS87 is as follows:

(SEQ ID NO.: 7)
MADTPSSEVIKETKVGSIIQQNNIKYKVLTVEGNIGTVQVGNGVTPVEF

EAGQDGKPFTIPTKITVGDKVFTVTEVASQAFSYYPDETGRIVYYPSSI

TIPSSIKKIQKKGFHGSKAKTIIFDKGSQLEKIEDRAFDFSELEEIELP

ASLEYIGTSAFSFSQKLKKLTFSSSSKLELISHEAFANLSNLEKLTLPK

SVKTLGSNLFRLTTSLKHVDVEEGNESFASVDGVLFSKDKTQLIYYPSQ

KNDESYKTPKETKELASYSFNKNSYLKKLELNEGLEKIGTFAFADAIKL

EEISLPNSLETIERLAFYGNLELKELILPDNVKNFGKHVMNGLPKLKSL

TIGNNINSLPSFFLSGVLDSLKEIHIKNKSTEFSVKKDTFAIPETVKFY

VTSEHIKDVLKSNLSTSNDIIVEKVDNIKQETDVAKPKKNSNQGVVGWV

KDKG

Chemically competent *E. coli* BL21 (DE3) cells were transformed with plasmid pJMS87 DNA. Expression of gene product was verified by the presence of an induced protein band of the correct size (i.e, approximately 49.4 kDa) by SDS-PAGE analysis.

As the cloned PcpA polypeptide lacks the signal sequence and choline-binding domains, its amino acid sequence correlates with amino acids 27 to 470 of the full length PcpA protein. This region is extremely conserved among all surveyed strains with only 8 variable positions. The most diverged pair of sequences shares 98.7% identity.

The predicted isoelectric points by Vector NTi for the recombinant PcpA protein and the recombinant PhtD protein were 7.19 and 5.16, respectively.

c) Antigen adsorption—The two recombinantly-derived protein antigens from *Streptococcus pneumoniae* (serotype 6 strain 14453, deposited on Jun. 27, 1997 as ATCC 55987), PhtD (WO2009/012588) and PcpA (WO2008/022302) were individually adsorbed to the phosphate-treated AlO (OH).

A mixture was prepared containing about 0.2 -0.4 mg/mL of purified antigen (i.e., rPcpA or rPhtD) and 0.56 mg elemental aluminum/ml/$PO_4$ mM of the PTH suspension. Alternatively, mixtures were prepared containing purified antigen with aluminum hydroxide adjuvant (as Alhydrogel® 85 2%) or $AlPO_4$ in Tris buffered saline (pH 7.4) using standard methods. The mixtures were mixed in an orbital mixer for about 30 minutes to 24 hours at room temperature to facilitate the association of antigen and adjuvant. Similar adsorptions were prepared a number of times and the typical pre-adsorbed composition was: protein (PhtD or PcpA): 0.2-0.4 mg/ml, phosphate: 2 to 80 mM (preferably, 2 to 20 mM) and AlO(OH): 1.25 mg/ml (0.56 mg of elemental Al/mi). Prepared antigen adsorbed samples were stored at about 2° C.-8° C. until used. Alternatively, antigens were adjuvanted together (to prepare bivalent formulations) by using a stock solution of phosphate treated aluminum hydroxide adjuvant.

d) Preparation of a bivalent formulation—The intermediate bulk lots (monovalent formulations) of PhtD adsorbed to PTH and PcpA adsorbed to PTH were blended and mixed together for about 30 minutes at room temperature in an orbital mixer to prepare a bivalent formulation. The typical pre-adsorbed formulation composition was: 0.05 mg/ml of each protein (rPhtD, rPcpA); phosphate: 2 to 80 mM (preferably 2 to 20 mM, more preferably 2 mM) and 1.25 mg/mL AlO(OH) (0.56 mg of elemental Al/ml).

Example 2

This example describes the evaluation of the stability of an adjuvanted vaccine formulation under various conditions. A number of PTH adsorbed vaccine formulations were incubated for 5 days at 5° C., 25° C., 37° C. (i.e., under thermal accelerated conditions).

To evaluate the stability of 4 different vaccine formulations of PcpA (formulated in AlO(OH) or PTH), the formulations were each incubated for 6 weeks at 37° C. and then assessed by RP-HPLC. The stability results obtained are summarized in Table 3. The recovery from untreated AlO (OH) decreased by almost 50% following the incubation period (at 37° C.) whereas little to no degradation was observed in the PTH containing formulations.

TABLE 3

% Recovery (RP-HPLC) of PcpA after 6 weeks incubation at 37° C.

| Formulation | % Recovery | | % Adsorption | |
|---|---|---|---|---|
| | T = 0 | T = 42 days | T = 0 | T = 42 days |
| 1) 50 μg/mL PcpA in 10 mM Tris-HCL, pH 7.4/150 mM NaCl/1.3 mg/mL AlO(OH) | 98 | 53 | 100 | 100 |
| 2) 50 μg/mL PcpA in 10 mM Tris-HCl, pH 7.4/150 mM NaCl/1.3 mg/mL AlO(OH)/2 mM Phosphate buffer pH 7.4 | 103 | 95 | 100 | 100 |
| 3) 50 μg/mL PcpA in 10 mM Tris-HCl, pH 7.4/150 mM NaCl/1.3 mg/mL AlO(OH)/20 mM Phosphate buffer pH 7.4 | 103 | 98 | 100 | 100 |
| 4) 50 μg/mL PcpA in 10 mM Tris-HCl, pH 7.4/150 mM NaCl/1.3 mg/mL AlO(OH)/80 mM Phosphate buffer pH 7.4 | 100 | 100 | 96 | 73 |

To evaluate the stability of PcpA and PhtD in monovalent and bivalent formulations (formulated with AlO(OH) or PTH), formulations were prepared as described in Example 1 using AlO(OH) or phosphate-treated AlO(OH) with 2 mM phosphate and samples were then incubated for about 16 weeks at various temperatures (i.e., 5° C., 25° C., 37° C. or 45° C.). Antigen concentration was then assessed by RP-HPLC. The stability results obtained are set out in FIGS. 1a to f. As shown the figures, in comparison to the formulations adjuvanted with untreated AlO(OH), the degradation rate of PcpA and PhtD, particularly under accelerated (stress) conditions (e.g., 25, 37, 45° C.) was significantly decreased in formulations adjuvanted with phosphate treated AlO(OH).

To evaluate the stability of the antigenicity of PcpA and PhtD in multi-valent formulations (formulated with AlO (OH) or PTH), bivalent formulations (at 100 μg/mL) were prepared as described in Example 1 and samples incubated at about 37° C. for approximately 12 weeks. Antigenicity of each formulation was evaluated by a quantitative ELISA sandwich assay at time zero and following the 12 week incubation period. Results are set out in FIG. 2. The antigenicity of both PcpA and PhtD following the 12 week incubation period at 37° C. was significantly higher when formulated with PTH in comparison to formulations with AlO(OH).

Example 3

This Example describes the analysis of the stability of multivalent formulations prepared with a pretreated aluminum adjuvant.

To prepare 10× Phosphate treated Aluminum hydroxide (PTH) (with a ratio of phosphate (P): Aluminum (Al)=0.1), a stock suspension of AlO(OH) adjuvant (Al=10.9 mg/ml, Alhydrogel "85" 2%, Brenntag) was blended with a stock solution of 500 mM phosphate buffer pH 7.4 (anhydrous Na$_2$HPO$_4$, JT Baker and NaH$_2$PO$_4$, EM science) and diluted to a final concentration of 5.6 mg Al/ml with TBS buffer (10 mM Tris-HCl(Trisma base, JT Baker) pH 7.4/150 mM NaCl (EMD Chemicals)). This preparation was mixed in an orbital mixer for approximately 17 hours at room temperature. The phosphorous:aluminum molar ratio was 0.1. PTH stock solutions with P:Al molar ratios of 0.5 and 1.0 were similarly prepared.

Three recombinantly-derived protein antigens from *S. pneumoniae* (serotype 6 strain 14453, deposited on Jun. 27, 1997 as ATCC 55987), PhtD (WO2009/012588). PcpA (WO 2008/022302) and a genetically modified, enzymatically inactive, pneumolysin mutant (PCT/CA2009/001843) were recombinantly expressed in *E. coli* and purified by serial column chromatography following conventional purification protocols. The three protein antigens were individually adsorbed at about 300 μg/mL (3× intermediate bulk) by mixing protein stock solutions with the PTH suspension (or, for the control formulations, untreated AlO(OH) (Alhydrogel "85" 2%, Brenntag) and the appropriate amount of TBS buffer for about 30 min at room temperature in an orbital mixer. Final trivalent formulations were prepared by blending equal volumes of 3× intermediate bulks (see FIG. 3 which provides a simplified depiction of the manufacturing process for lab scale lots).

Stability

Stability was evaluated under normal and stress conditions. Formulations were incubated at 5, 25, 37 and 45° C. and chemical integrity was evaluated by RP-HPLC and SDS-PAGE. A summary of the stability data obtained for the trivalent formulations in AlO(OH) or PTH (P:Al=0.1) as evaluated by concentration of intact protein by RP-HPLC (in % of T=0) after 8-week incubation at 5° C. and 25° C. is set out in Table 4. The three proteins were each unstable when adjuvanted with untreated AlO(OH) as shown by the significant decrease in protein concentration following incubation at both 5° C. and 25° C. In contrast, proteins adjuvanted with PTH (P:Al=0.1) experienced minimal degradation during the incubation period (when stored at 5° C.) and significantly less degradation when stored at 25° C. in comparison to the formulations adjuvanted with untreated AlO (OH).

TABLE 4

Stability summary of trivalent formulation as evaluated by RP_HPLC after 8 weeks incubation at 5° C. and 25° C.

| Formulation | Relative conc. of Ply mutant % T = 0 | | Relative PcpA concentration % T = 0 | | Relative PhtD concentration % T = 0 | |
|---|---|---|---|---|---|---|
| | 5° C. | 25° C. | 5° C. | 25° C. | 5° C. | 25° C. |
| Formulation in AlO(OH) | 75.4 | 18.8 | 81.8 | 60.9 | 82.3 | 50.5 |
| PTH formulation (P:Al = 0.1) | 99.1 | 87.6 | 99.3 | 97.3 | 98.8 | 65.8 |

Adsorption

To assess the percentage of each antigen adsorbed to the adjuvant, formulation samples (with each protein at 100 µg/ml and adjuvated with PTH with varying P:Al molar ratios) were centrifuged for about 5 minutes at 4.000×g and each protein's concentration in the supernatant was determined. Isoelectric points for each antigen were predicted by Vector NTi (as described in Example 1). Table 5 sets out a summary of the % adsorption of each antigen in various formulations tested. The results indicate that adsorption of acidic antigens (isoelectric point <7.0) is decreased as the P:Al is increased. In regards to PcpA (a neutral antigen), there was no change in % adsorption at P:Al of 0.5 and decreased by only 1% at a P:Al of 1.0. At the concentration of Al used in this example (0.56 mg/mL) optimal adsorption for all three antigens (>90%) was obtained when the P:Al molar ratio was 0.1. The adsorption of acidic antigens to PTH at higher P:Al ratios may be improved by increasing the concentration of adjuvant in the formulation (e.g., up to the maximum concentration of Al permitted by regulatory bodies (e.g., 0.85 mg aluminum/vaccine dose (FDA)).

TABLE 5

Percentage of adsorption (% A) of protein antigens to PTH prepared at different P:Al ratios. PTH concentration was 0.56 mg Al/ml; concentration of each antigen was 100 µg/ml.

| | Isoelectric point | P:Al 0.1 | P:Al 0.5 | P:Al 1.0 |
|---|---|---|---|---|
| Ply mutant | 5.13 | 98% | 42% | 24% |
| PhtD | 5.16 | 100% | 91% | 82% |
| PcpA | 7.19 | 97% | 97% | 96% |

Example 4

Effects of Phosphate Treatment on Immunogenicity of Vaccine Formulation

This Example describes the analysis of the immunogenicity of a multi-component vaccine in an animal model. Balb/c female mice were immunized to assess the immune response elicited by a bivalent vaccine composition formulated with one of several different adjuvants. Formulations were prepared (as described in Example 1) using purified recombinant PhtD and PcpA proteins. The formulations were mixed on a Nutator for approximately 30 minutes and dispensed into glass vials. Groups of mice were immunized intramuscularly (IM) three times at 3 week intervals with the applicable formulation. Specific formulations used were as follows:

A. 100µg/mL of each of PhtD and PcpA in TBS pH=7.4, unadjuvanted

B. 100µg/mL of each of PhtD and PcpA+1.3 mg/mL AlOOH (Alhydrogel "85" 2%, 25.08 mg/ml) in Tris Saline pH=7.4

C. 100 µg/mL of each 2 proteins in TBS pH 7.4+1.3 mg/mL AlOOH pretreated with 2 mM Phosphate, pH 7.4.

Sera were collected prior to each immunization and three weeks following the final immunization. Total antigen-specific IgG titres were measured by endpoint dilution ELISA and geometric mean titres (+/−SD) for each group were calculated. A summary of the total IgG titers obtained are set out in the Table 6 below.

TABLE 6

Combined anti-PcpA and anti-PhtD Total IgG Titers Geomean

| Immunizing agent | Anti-PcpA IgG | Bleed III SD | Anti-PhtD IgG | Bleed III SD |
|---|---|---|---|---|
| 2-valent in TBS | 19986.15506 | 27007.46336 | 46680.19141 | 48923.68401 |
| 2-valent in AlO(OH) | 178288.7554 | 116860.8322 | 224629.7558 | 72062.11078 |
| 2-valent in PTH | 186720.7657 | 73604.63754 | 162549.8677 | 54046.58308 |

Figure 4A:
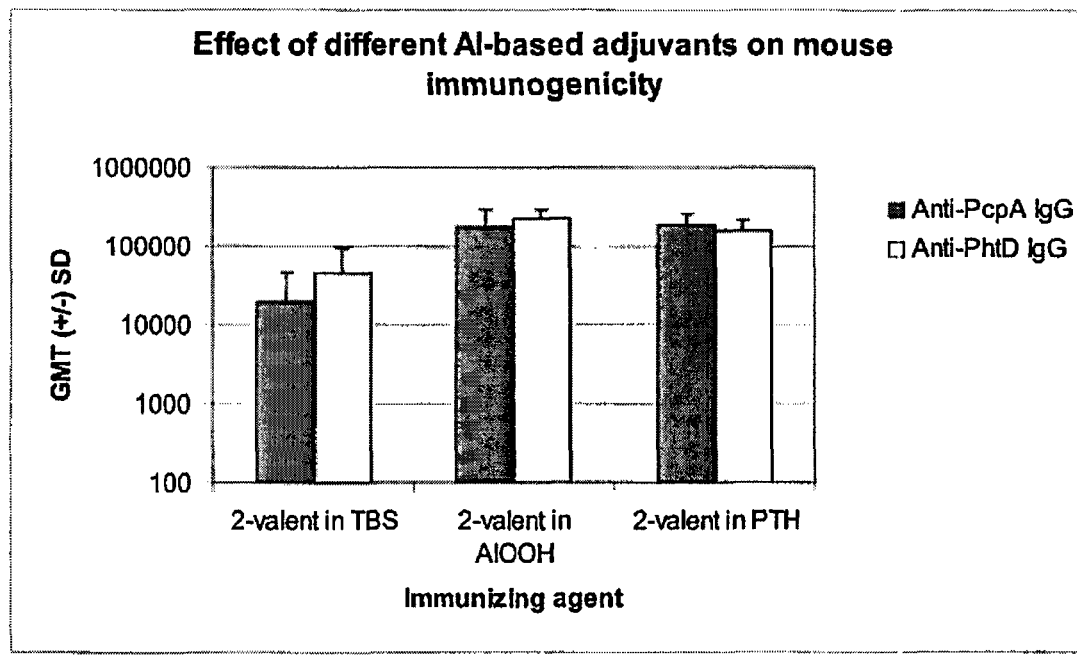
FIGS. 4a, 4b, 4c. Balb/c mice were used to assess the immune response elicited by a bivalent vaccine composition formulated with one of several different adjuvants (Example 4). Formulations were prepared (as described in Example 1) using purified recombinant PhtD and PcpA proteins. Total antigen-specific IgG titres were measured by endpoint dilution ELISA (FIG. 4a) and geometric mean titres (+/−SD) for each group were calculated. Antigen-specific IgG1 (FIG. 4b) and IgG2 titers (FIG. 4c) were calculated to assess IgG1/2a sub-classing. A summary of the results are depicted in this Figure.
Figure 4B:
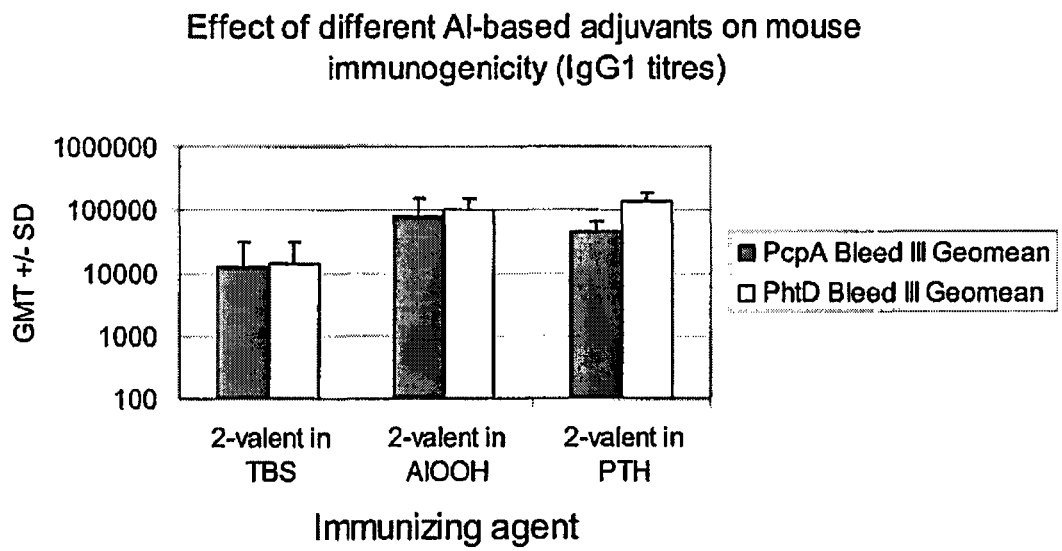
Figure 4C:
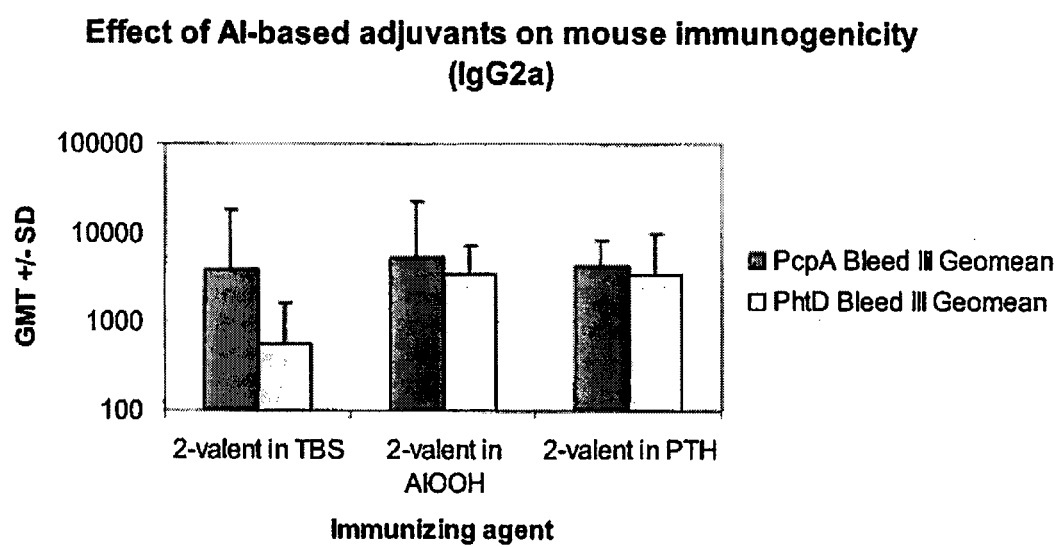

Antigen-specific IgG1 and IgG2a titers were also calculated to assess IgG1/2a sub-classing. A summary of the results are depicted in FIGS. 4a, 4b, and 4c.

The adjuvanted bivalent compositions formulated with either AlO(OH) or phosphate treated AlO(OH) elicited IgG antibody titers (IgG1, IgG2a and total IgG) that were comparable (i.e., not significantly different) and significantly higher than the unadjuvanted formulation. Based on IgG 1/2a sub-classing, the composition formulated with AlO (OH) and the composition formulated with phosphate treated AlO(OH) each elicited a Th2 type of immune response (i.e., IgG1 was the predominant IgG subtype in mice sera).

Example 5

Effects of Phosphate Treatment on Immunogenicity of Vaccine Formulation

This Example describes the analysis of the immunogenicity of a multi-component composition formulated with different aluminum-based adjuvants.

Balb/c female mice were used to assess the immune response elicited by a bivalent vaccine composition formulated with one of several different adjuvants. In this study, recombinant PhtD and PcpA (prepared and purified as described in Example 1) were formulated with AlO(OH), or AlO(OH)-treated with $PO_4$ at different phosphate molarities (2 mM, 10 mM and 20 mM) or AlPO4 (Adjuphos™ purchased from Brenntag). Formulations were prepared as described in Example 1. Two batches of each AlO(OH) formulation were used in this study: one batch was prepared and then aged (i.e., incubated at about 2-8° C. for approximately 6 months) and a second batch was prepared within one week of the first immunization (i.e., freshly prepared formulation).

Groups of 5 (or 4) female Balb/c mice (Charles River), 6-8 weeks of age upon arrival, were immunized intramuscularly (IM) three times at 3 week intervals with the applicable formulation. The specific formulations administered to each group is set out in Table 7.

The PhtD and PcpA-specific antibody ELISA titers following the final bleed are summarized in Table 7. Mice immunized with PcpA and/or PhtD proteins generated antigen-specific antibody responses after immunization. No significant differences in anti-PhtD and anti-PcpA titres were seen in animals immunized with either fresh or aged AlO (OH)-containing bivalent formulations or formulations containing AlO(OH) pre-treated with phosphate (at any of the three concentrations used). Immunization with the bivalent composition formulated with $AlPO_4$ (which is less immunogenic than AlO(OH)) gave rise to significantly lower anti-PhtD IgG titres when compared to formulations containing AlO(OH) or $PO_4$-containing AlO(OH) adjuvants.

TABLE 7

PcpA and PhtD-specific ELISA Titers for Groups of Mice Immunized with Placebo or Bivalent Vaccine Formulation

| Group | Bleed* | ELISA Titers PcpA | PhtD |
|---|---|---|---|
| 5 μg PcpA + PhtD + AlOOH | Pre-immunization | <100 | <100 |
|  | Final bleed | 152166 | 88266 |
| 5 μg PcpA + PhtD + AlOOH with 2 mM $PO_4$ | Pre-immunization | <100 | <100 |
|  | Final bleed | 204800 | 88266 |
| 5 μg PcpA + PhtD + AlOOH with 10 mM $PO_4$ | Pre-immunization | <100 | <100 |
|  | Final bleed | 204800 | 64508 |
| 5 μg PcpA + PhtD + AlOOH with 20 mM $PO_4$ | Pre-immunization | <100 | <100 |
|  | Final bleed | 176532 | 68910 |
| 10 μg PcpA + PhtD + fresh AlOOH | Pre-immunization | <100 | <100 |
|  | Final bleed | 176532 | 97454 |
| 10 μg PcpA + PhtD + aged AlOOH | Pre-immunization | <100 | <100 |
|  | Final bleed | 168005 | 88266 |
| 5 μg PcpA + PhtD + AlPO4 | Pre-immunization | <100 | <100 |
|  | Final bleed | 124827 | 36204 |

*Final bleed anti-PcpA and anti-PhtD titers were determined from individual mice and are represented as the geometrical mean.

Example 6

Effects of Phosphate Treatment on Immunogenicity and Stability of Vaccine Formulation This Example describes the analysis of the immunogenicity of a multi-component composition formulated with different aluminum-based adjuvants.

Balb/c female mice were used to assess the immune response elicited by fresh and aged adjuvanted bivalent formulations. To prepare the bivalent formulations, recombinant PhtD and PcpA were formulated with AlO(OH), or AlO(OH)-containing $PO_4$ (2 mM) as described in Example 1. The aged formulations used in the study had been stored for approximately 6 months at about 2° C.-8° C. prior to the first immunization. The freshly prepared formulations used in the study were prepared within one week of the first immunization. Groups of mice were immunized intramuscularly (IM) three times at 3 week intervals with the applicable formulation.

Sera were collected prior to each immunization and three weeks following the final immunization. Total antigen-specific IgG titres were measured by endpoint dilution ELISA and geometric mean titres (+/−SD) for each group were calculated. A summary of the total IgG titers obtained are set out in FIG. 5.

There was no statistical difference in the α-PhtD and α-PcpA titers elicited by the both the AlO(OH) and phosphate treated AlO(OH) formulations (which is akin to the results obtained in the study set out in Example 5). However, the aged formulations adjuvanted with either AlO(OH) or PTH elicited higher antigen specific IgG titers than their freshly prepared counterparts, which is in contrast to the Example 5 study where no statistical difference in anti-PhtD and anti-PcpA titers elicited with either fresh or aged bivalent formulations with AlO(OH). In this study, the difference noted between aged and freshly prepared formulations in elicited titres was mostly likely due to the fact that the aged and the freshly prepared formulations were prepared with different lots of AlO(OH) (Alhydrogel™).

A subsequent study was performed using freshly prepared and aged bivalent formulations adjuvanted with AlO(OH) (Alhydrogel, Brenntag) treated with 2 mM of phosphate. The freshly prepared and aged formulations were each prepared using the same lot of Alhydrogel. Samples of prepared formulations were stored at 2 to 8° C. or 37° C. for approximately 6 to 7 months prior to the start of the study. Total antigen-specific IgG titers were measured by quantitative ELISA and a summary of the total IgG titers obtained are set out in FIG. 8. There were no statistical differences in the α-PcpA and α-PhtD ELISA titres between the freshly prepared bivalent adjuvanted formulations and the bivalent adjuvanted formulations that had been aged 6 months at 2-8° C. The storage conditions under which the phosphate pretreated AlO(OH) formulations were subjected did not adversely affect immunogenicity and therefore, the formulations adjuvanted with phosphate pretreated AlO(OH) were stable under the conditions tested.

Example 7

Effects of Phosphate Treatment on Immunogenicity and Protection of Vaccine Formulation This Example describes the protective ability of a multi-component vaccine against fatal pneumococcal challenge in the mouse intranasal challenge model (which is an active immunization model based on one described earlier, Zhang, Y. A, et. al. *Infect. Immun.* 69:3827-3836 (2001).

Bivalent compositions of rPhtD and rPcpA were prepared containing a 5 μg/dose of each of purified recombinant PhtD and PcpA proteins, formulated in TBS with adjuvant (AlOOH treated with 2 mM PO4 (65 μg/dose)) as described in Examples 1A and 1B. In this study, groups of female CBA/j mice (N=15 per group) were immunized intramuscularly (IM) three times at 3 week intervals with the applicable formulation. The injection volume was 50 μL per dose. As a negative control, a PBS placebo-containing aluminum adjuvant was injected.

At about 9 weeks, animals were administered a lethal dose (approximately 106 CFU) intranasally of a *S. pneumoniae* strain MD, strain 14453 or 941192 in PBS suspension (40 μL challenge volume per mouse). Sample bleeds were taken from all animals 4 days prior to the first injection (pre-immunization at 0 weeks) and 4 days prior to the challenge. Sera were analyzed for total PhtD and PcpA-specific IgG response by means of an antibody ELISA assay.

Following the challenge, mice were monitored daily for mortality. All surviving mice were euthanized 11 days post-challenge. Protection was determined using Fisher's one-sided Exact test by comparing survival in the immunized group(s) to the placebo control (p values <0.05 were considered significant). The results of the study (noted in % survival) are set out in FIG. 7 and Table 8 below.

TABLE 8

Survival Results of Mice Immunized with Bivalent Vaccine or Placebo

| | Bivalent Survival in % | | Placebo Survival in % | |
| --- | --- | --- | --- | --- |
| Day | Strain 14453 | Strain MD | Strain 14453 | Strain MD |
| 0 | 100 | 100 | 100 | 100 |
| 1 | 100 | 100 | 100 | 100 |
| 2 | 100 | 93.3 | 73.3 | 20 |
| 3 | 100 | 93.3 | 40 | 6.7 |
| 4 | 86.7 | 93.3 | 40 | 6.7 |
| 5 | 86.7 | 93.3 | 40 | 6.7 |
| 6 | 86.7 | 93.3 | 40 | 6.7 |
| 7 | 86.7 | 93.3 | 40 | 6.7 |
| 8 | 86.7 | 93.3 | 40 | 6.7 |
| 9 | 86.7 | 93.3 | 40 | 6.7 |
| 10 | 86.7 | 93.3 | 40 | 6.7 |
| 11 | 86.7 | 93.3 | 40 | 6.7 |
| p-value* | 0.01 | 0.000 | | |

*p-value calculated using the Fisher exact test versus placebo group; difference from placebo group 11 days post-challenge Immunization with combined recombinant PhtD and PcpA proteins generated protection against fatal IN challenge with three different strains of *S. pneumoniae* in the IN challenge model. The protection noted in groups that had been challenged with either the 14453 strain or the MD strain was statistically significant. The group challenged with the 941192 strain also had a high % survival, but the protection was not considered statistically significant in light of the percentage of survival noted in the negative control group (immunized with adjuvant alone).

Example 8

Effects of Aluminum Concentration on Immunogenicity of Vaccine Formulation

This Example describes the analysis of the immunogenicity of a multi-component composition formulated with phosphate pretreated AlO(OH) and varying concentrations of elemental aluminum.

Female Balb/c mice were used to assess the immune response elicited by adjuvanted trivalent formulations. To prepare the trivalent formulations, recombinant PhtD, PcpA and an enzymatically inactive pneumolysin mutant (each derived from *S. pneumoniae*) were formulated with AlO(OH)-containing $PO_4$ (2 mM) as described in Example 1. Samples of prepared formulations were stored at 2 to 8° C. prior to the start of the study. Groups of Balb/c mice were immunized intramuscularly (IM) three times at 3 week intervals with the applicable formulation:

A. Unadjuvanted (Trivalent 50 μg/mL of PcpA and PhtD and 100 μg/mL of Ply mutant in TBS pH=7.4)

B. Trivalent 50 μg/mL of PcpA and PhtD and 100 μg/mL of Ply mutant +0.56 mg Al/mL PTH, P:Al molar ratio=0.1 (0.56 mg Al/mL AlO(OH) treated with 2 mM PO4) in Tris Saline pH=7.4.

C. Trivalent 50 μg/mL of PcpA and PhtD and 100 μg/mL of Ply mutant+0.28 mg Al/mL PTH, P:Al molar ratio=0.1 (0.28 mg Al/mL AlO (OH) treated with 1 mM PO4) in Tris Saline pH=7.4.

D. Trivalent 50 μg/mL of PcpA and PhtD and 100 μg/mL of Ply mutant+1.12 mg Al/mL PTH, P:Al molar ratio=0.1 (1.12 mg Al/mL AlO(OH) treated with 4 mM PO4) in Tris Saline pH=7.4.

E. Trivalent 50 μg/mL of PcpA and PhtD and 100 μg/mL of Ply mutant+1.68 mg Al/mL PTH, P:Al molar ratio=0.1 (1.68 mg Al/mL AlO (OH) treated with 6 mM PO4) in Tris Saline pH=7.4.

Sera were collected following the $1^{st}$, second and third immunization. Total antigen-specific IgG titres were measured by quantitative ELISA and geometric mean titres (+/−SD) for each group were calculated. A summary of the total IgG titers obtained are set out in FIG. 8.

All adjuvanted groups (B, C, D and E) produced significantly higher titres against all three antigens than the unadjuvanted group (A) ($p<0.001$). With respect to each antigen, titre levels peaked when adjuvanted with PTH with 0.56 mg elemental aluminum/nth (and, in the case of PhtD, the difference between titres elicited with aluminum 0.56 mg /mL and the two higher concentrations was statistically significant). Similarly, with respect to each antigen, titre levels were lower when adjuvanted with PTH with 0.28 mg elemental aluminum/mL (and, in the case of PcpA, the difference was statistically significant). These findings were surprising. Antibody (IgG) titers were expected to increase proportional to the concentration of aluminum (as reported in Little S. F. et. al., Vaccine, 25:2771-2777 (2007)). Surprisingly, even though the concentration of each of the antigens was kept constant, the titres decreased, rather than plateau, with increasing aluminum concentration (and with PhtD this was statistically significant).

Example 9

Adjuvant Physiochemical Characterization

This Example describes the physiochemical characterization of a number of different adjuvant samples. Characterization tests were performed using samples from a number of different 10× PTH stock solutions (each of which had been prepared as described in Examples 1 and 3). A number of bulk samples of aluminum hydroxide adjuvant (Alhydrogel, Brenntag) and one bulk sample of AlPO4 (Adjuphos, Brenntag) were also used in the characterization tests.

The different PTH stock solutions (batches) were manufactured on different days by different operators. The content of Al and P in each batch was measured to evaluate consistency. The measured Al:P molar ratios are set out in Table 9.

TABLE 9

Al:P molar ratios in different lots of PTH

| PTH Lot # | Lot Type | P (mmol/L) | Al (mg/mL) | P:Al molar ratio |
|---|---|---|---|---|
| A | Lab Scale | 20.1 | 5.1 | 0.11 |
| B | Scale up Demo | 22.3 | 5.3 | 0.11 |
| C | Consistency | 19.6 | 4.9 | 0.11 |
| D | Consistency | 20.1 | 5.6 | 0.10 |
| E | GMP demo lot | 20.1 | 5.6 | 0.10 |

TABLE 9-continued

Al:P molar ratios in different lots of PTH

| PTH Lot # | Lot Type | P (mmol/L) | Al (mg/mL) | P:Al molar ratio |
|---|---|---|---|---|
| | | Average: 20.4 | Average: 5.3 | Average: 0.11 |
| | | RSD: 5.2% | RSD: 5.7% | RSD: 7.6% |

Point of Zero Charge (PZC)

The PZC of five different samples of 10× PTH, two bulk samples of aluminum hydroxide adjuvant (Alhydrogel, Brenntag) and one bulk sample of AlPO4 (Adjuphos, Brenntag) was measured using the Zetasizer Nano-ZS, Nano series (Malvern Instruments). Samples were prepared by hand or by an automatic titrator (Multi Purpose Titrator, Malvern Instruments) linked to the Zetasizer. In the range of the PZC (+/−2 units of pH), the relation between Zeta potential and pH is linear and as such, the PZC may be determined by reading the pH for which the linear regression intercepts the x-axis. A summary of the results obtained are set out in Table 6.

PZC can be defined as the pH value at which the net surface charge of the aluminum adjuvant is zero. The surfaces of aluminum hydroxide adjuvant are charged by either amphoteric dissociation of surface hydroxyl groups or by the adsorption of H+ or HO− from the aqueous environment and the presence of ions such as phosphate, sulfate and carbonate may influence PZC. As set out in Table 6, the PZC of AlOOH was significantly reduced as a result of the pretreatment with phosphate. Little variability on PZC was observed for all six lots of PTH under analysis (RSD 2.9%) suggesting consistency and comparability among the PTH batches analyzed in this study.

Two different AlOOH lots were tested and the PZC of both were about 1.3 units lower than the value reported in the literature for commercial AlOOH (~11). The point of zero charge of Adjuphos was within the accepted values for Aluminum Phosphate adjuvant reported in the literature (Gupta R. Aluminum compound as vaccine adjuvants. Adv Drug Deliv Rev. 1998 Jul 6;32(3):155-172.)

Particle Size

Particle size was measured by laser diffraction granulometry using a Mastersizer 2000 linked to a Hydro 2000S sample dispersion unit (Malvern Instruments). The results were processed by volume and that data typically utilized for characterization was d(0.5)(i.e., the diameter below which 50% of the particles are distributed by volume (d(0.1) and d(0.9) are the same respectfully for 10% and 90%). A summary of the results obtained are set out in Table 10.

TABLE 10

PZC and particle size results obtained for PTH, AlOOH and AlPO4 batches

| Lot | Lot Type | PZC | Particle Size D0.5 (μm) |
|---|---|---|---|
| A | Lab Scale | 6.4 | 4.4 |
| B | Scale-up Demo | 6.1 | 3.7 |
| C | Consistency | 6.5 | 5.0 |
| D | Consistency | 6.5 | 5.4 |
| E | GMP demo lot | 6.2 | 4.9 |
| | | Average: 6.3 | Average: 4.7 |
| | | RSD: 2.9% | RSD: 14% |
| 85381 | AlOOH (Alhydrogel, Brenntag) | 9.7 | 5.4 |
| 85350 | AlOOH (Alhydrogel, Brenntag) | * | 8.7 |

TABLE 10-continued

PZC and particle size results obtained for PTH, AlOOH and AlPO4 batches

| Lot | Lot Type | PZC | Particle Size D0.5 (μm) |
|---|---|---|---|
| 85335 | AlOOH (Alhydrogel, Brenntag) | * | 7.0 |
| 85378 | AlOOH (Alhydrogel, Brenntag) | 9.7 | 6.8 |
| | | Average: 9.7 RSD: 0% | Average: 7.0 RSD: 19.4% |
| 9093 | AlPO$_4$ (Adjuphos, Brenntag) | 5.1 | 2.7 |

*Testing not performed

Particle size is an important parameter for the mechanism of action of aluminum adjuvants as aluminum adjuvants are capable of converting soluble protein antigens into particulates that are more readily phagocytized by dendritic cells. For optimal adjuvanticity, it is generally recommended that the particle size of an aluminum adjuvant is less than 10 μm (Vaccine, 2005 Feb 18;23(13):1588-95). Particle size measurements may also be used to monitor consistency in lot manufacturing.

The particle sizes obtained for all six lots of PTH were smaller than the upper limit value of 10 μm. On average the particle size of PTH was 4.4 μm with an RSD of 14%. The particle sizes of the Alhydrogel batches tested and the tested Adjuphos batch were also below 10 μm. The Alhydrogel batches however showed larger particle sizes and greater variability than the PTH batches tested (Table 7).

Protein Adsorption Capacity (rHSA)

Adsorption isotherms were conducted by titration of the adjuvant sample with increasing concentrations of a model protein, rHSA (Recombumin®, Novozymes) at concentrations ranging from 0 to 2500 μg/ml. The isoelectric point of rHSA is approximately 5 and it binds to aluminum hydroxide adjuvant primarily by electrostatic interactions. The tubes were mixed in a Nutator mixer for 2 h at room temperature and then incubated at 2-8 degrees overnight. The samples were then centrifuged 5 min at 4000×g. the supernatants were collected and protein was quantitated by Micro BCA assay kit. Adsorptive capacity was calculated using the linearized Langmuir equation: CE/MA=(CE/Ac)+(1/CE K), where: CE: Conc. in equilibrium (supernatant concentration); MA: Mass of protein Adsorbed per mass of adsorbent; K: adsorptive coefficient; Ac: Adsorptive capacity. A summary of the calculated adsorption isotherms obtained for AlOOH, PTH and AlPO$_4$ is set out in Table 11.

TABLE 11

Adsorptive Capacity obtained for different lots of 10X PTH and AlOOH

| Lot # | Lot Type | Adsorptive Capacity (mg HSA/mg Al) |
|---|---|---|
| A | Lab Scale | 1.85 |
| B | Scale up Demo | 2.08 |
| C | Consistency | 2.00 |
| D | Consistency | 1.47 |
| E | GMP demo lot | 1.43 |
| | | Average = 1.77 (RSD = 15.2%) |
| 85381 | AlOOH (Alhydrogel, Brenntag) | 2.50 |
| 85350 | AlOOH (Alhydrogel, Brenntag) | 2.63 |
| 85335 | AlOOH (Alhydrogel, Brenntag) | 2.70 |
| 85378 | AlOOH (Alhydrogel, Brenntag) | 2.44 |
| | | Average = 2.57 (RSD = 4.0%) |
| 9093 | AlPO$_4$ (Adjuphos, Brenntag) | (not calculable) |

As expected, the PTH lots had reduced adsorption isotherms in comparison to the AlOOH lots. With respect to the AlPO$_4$ lot tested, very little adsorption of rHSA was observed and as a result, adsorption capacity could not be calculated.

Crystallinity

The crystallinity of the different adjuvant samples was evaluated by X-ray diffraction. An X-ray diffractogram of each adjuvant was performed in a Thermo ARL X'TRA X-ray diffractometer. As the presence of salt from TBS interferes with the diffractogram of Aluminum adjuvants, samples were washed five times by centrifugation and resuspension in MilliQ water. Samples were air dried at room temperature and examined from 5 to 70° at a scan rate of 1 °/min (Siemens, Madison, Wis.) as previously reported (Gupta R. Aluminum compound as vaccine adjuvants. Adv Drug Deliv Rev. 1998 Jul 6;32(3):155-172.).

Figure 5:
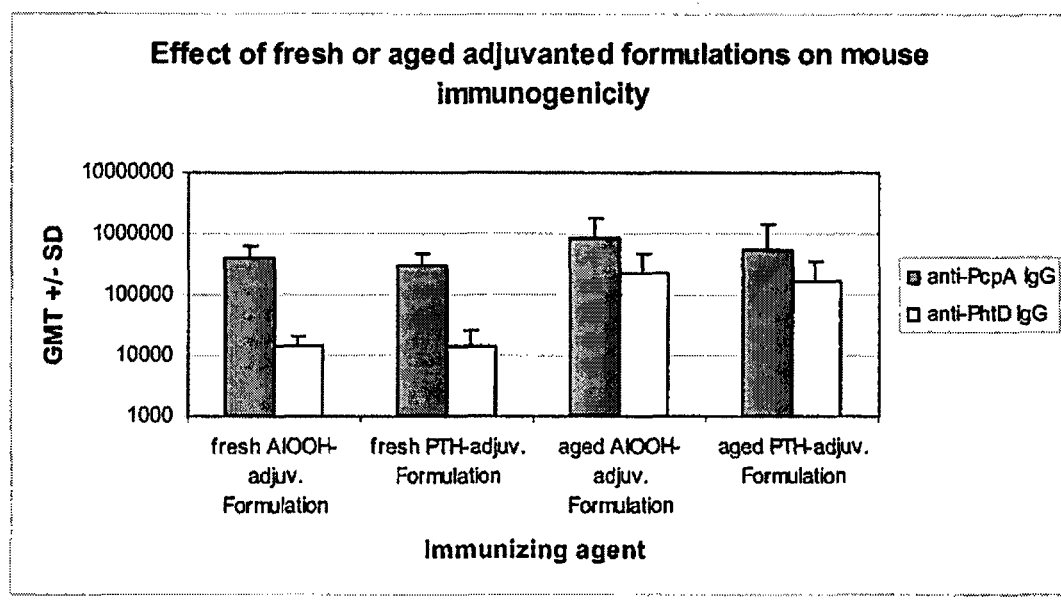
FIG. 5. Depicts the total antigen-specific IgG titres measured by endpoint dilution ELISA and geometric mean titres (+/−SD) for each group. In this study (Example 6), Balb/c mice were used to assess the immune response elicited by freshly prepared and aged adjuvanted bivalent formulations. Recombinant PhtD and PcpA were formulated with AlOOH, or AlOOH-containing $PO_4$ (2 mM). The aged formulations used in the study had been stored for approximately 6 months (about 2° C. to 8° C.) prior to the first immunization. The freshly prepared formulations used in the study were prepared within one week of the first immunization. Groups of mice were immunized intramuscularly (IM) three times at 3 week intervals with the applicable formulation.
Figure 6:
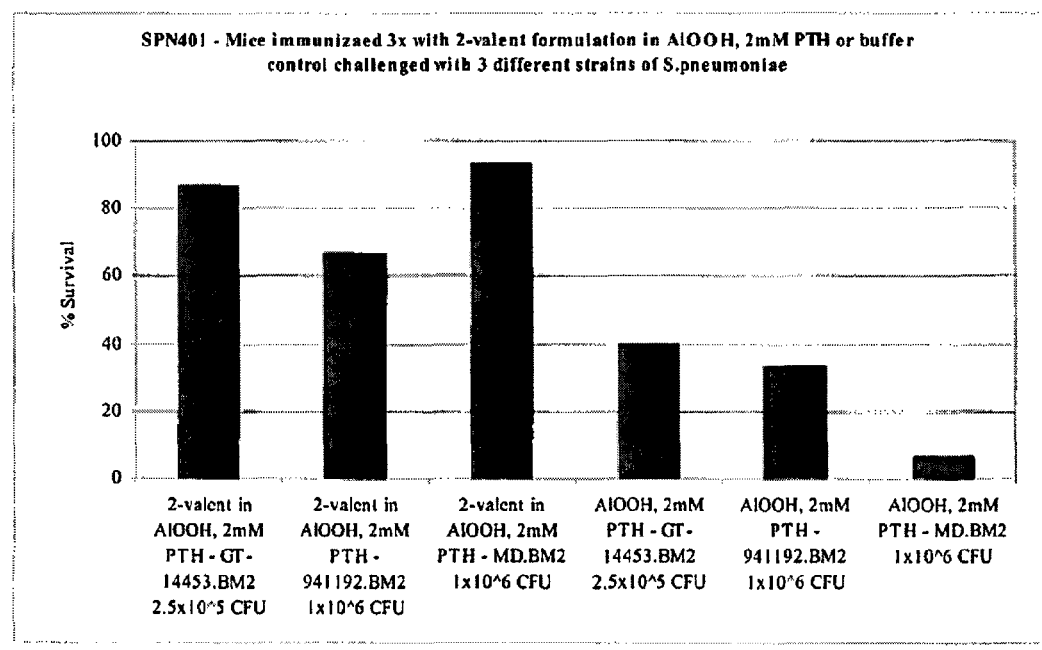
FIG. 6 Depicts the survival percentage for each group of mice immunized (Example 6). In this study, a bivalent formulation of recombinant PhtD and PcpA was evaluated using an intranasal challenge model. Immunized animals were challenged with a lethal dose of an *S. pneumoniae* strain (MD, 14453 or 941192).

Commercial sources of AlOOH display varying degrees of crystallinity when analyzed by XRD. Typically AlOOH shows broad reflections at 12.6, 27.5, 38.2, 48.4 and 64.4° 2θ which correspond to d-spacing of 6.46, 3.18, 2.35, 1.86, 1.44 and 1.31 Å (FIG. 5). Those are fingerprint bands that identify the mineral bohemite, a crystalline phase of AlOOH. In this context, XRD can be used as identity test for AlOOH. On the other hand, AlPO$_4$ is amorphous to X-Rays and therefore cannot be identified by XRD. A single broad peak is typically observed in the diffractogram of AlPO$_4$ (see FIG. 10)

All six PTH lots analyzed displayed diffractograms undistinguishable from those of AlOOH showing the aforementioned fingerprint reflections bands of bohemite. These results indicate that the addition of phosphate to produce PTH did not alter the crystalline structure of AlOOH.

XRD can be also used to determine the degree of crystallinity of a given adjuvant sample. The degree of crystallinity is typically monitored by the diffraction band at half height (WHH) and has been reported to be directly related to the protein adsorption capacity of the adjuvant (Seeber S J; White J L; Hem S L. Predicting the adsorption of proteins by aluminium-containing adjuvants. Vaccine. 1991(3):201-3.). The WWH of the reflection band at 12.6° 2θ for all lots under analysis is set out in Table 12. Little variation was observed among the PTH lots suggesting similar degree of crystallinity. Additionally, PTH batches displayed lower degree of crystallinity compared to the AlOOH (see Table 12).

TABLE 12

Degree of Crystallinity of different lots of PTH as evaluated by the WHH of the 12.6 ° 2θ reflection band.

| Lot # | Lot Type | WWH (° 2θ) |
|---|---|---|
| A | Lab Scale | 4.57 |
| B | Scale up Demo | 4.50 |
| C | Consistency | 4.61 |
| D | Consistency | 4.21 |
| E | GMP demo lot | 4.81 |
| | | Average: 4.56, RSD 4.39% |
| 85381 | AlOOH (Alhydrogel, Brenntag) | 4.54 |
| 85350 | AlOOH (Alhydrogel, Brenntag) | 3.71 |
| 85335 | AlOOH (Alhydrogel, Brenntag) | 3.47 |
| 85378 | AlOOH (Alhydrogel, Brenntag) | 4.49 |
| | | Average: 4.05, RSD 13.4% |

Morphology

Microscopic examination of adjuvants was conducted. A drop of sample (5 μl) was placed directly onto a glow discharged carbon coated 400 mesh copper grid. After two minutes the grid was blotted dry with filter paper. Samples were examined in a Hitachi H7000 transmission electron microscope at 75 Kv and captured in an AMT 60XR CCD camera.

Aluminum hydroxide adjuvant and aluminum phosphate adjuvant are composed of small primary particles that form aggregates of various sizes. The primary particles of aluminum hydroxide adjuvant appear as fibers of about 10 nm that form aggregates ranging from 1 to 20 μm in diameter. The aluminum phosphate primary particles, on the other hand, are plate-like structures of about 50 nm that form aggregates of similar size to those of aluminum hydroxide adjuvant (see FIG. 10).

Although PTH results from the treatment of AlOOH with phosphate ions, PTH displays microscopic characteristics indistinguishable from AlOOH suggesting that the addition of phosphate did not alter the structure of AlOOH (see FIG. 12). All PTH lots showed similar morphology suggesting consistency and comparability among the batches analyzed.

Example 10

Effects of pH

The effect of pH on the physical stability of three different antigens formulated with or without an aluminum adjuvant was performed. An assay was used to evaluate the effect of pH on the thermal stability of each protein under evaluation (i.e., PcpA, PhtD and a detoxified pneumolysin mutant (PlyD1, as described in PCT/CA2009/001843:Modified PLY Nucleic Acids and Polypeptides, as SEQ ID NO:44 and noted in the Sequence Listing herein as SEQ ID NO:9).

Each of the protein antigens were recombinantly expressed in $E.$ $coli$ and purified by serial column chromatography following conventional purification protocols substantially as described in Example 1, for PhtD and PcpA and as described in PCT/CA2009/001843 for PlyD1. Protein purity for all three antigens was typically higher than 90% as evaluated by RP-HPLC and SDS-PAGE. Proteins bulks were supplied at approximately 1 mg/mL in 10 mM Tris, pH 7.4 containing 150 mM sodium chloride. Each protein was diluted to the desired concentration (100 μg/mL PcpA; 100 μg/mL PhtD; 200 μg/mL PlyD1) with the appropriate buffer solution (i.e., 10 mM Tris buffer (pH 7.5-9.0), 10 mM phosphate buffer (pH 6.0-7.0) and 10 mM acetate buffer (pH 5.0-5.5)) and an aluminum adjuvant (i.e., aluminum hydroxide (Alhydrogel, Brenntag Biosector, Denmark), or aluminum phosphate (Adju-Phos, Brenntag Biosector. Denmark) or PTH) was added to the protein solutions to achieve a final concentration of 0.6 mg of elemental Al/mL. Control samples (lacking the applicable adjuvant) were also assayed. SYPRO® Orange, 5000× (Invitrogen, Inc., Carlsbad, Calif.), was diluted to 500× with DMSO (Sigma) and then added to the adjuvanted protein solutions. In all cases optimal dilution of SYPRO-Orange was 10× from a commercial stock solution of 5000×.

Assays were performed in a 96 well polypropylene plate (Stratagene, La Jolla, Calif.) using a real-time polymerase chain reaction (RT-PCR) instrument (Mx3005p QPCR Systems, Stratagene, La Jolla, Calif.). A sample volume of approximately 100 μL was added to each well and the plate was then capped with optical cap strips (Stratagene, La Jolla, Calif.) to prevent sample evaporation. Plates were centrifuged at 200 g for 1 min at room temperature in a Contifuge Stratos centrifuge (Heraeus Instruments, England) equipped with a 96 well plate rotor. The plates were then heated at 1° C. per min from 25° C. to 96 ° C. Fluorescence excitation and emission filters were set at 492 nm and 610 nm, respectively. Fluorescence readings (emission at 610 nm, excitation at 492 nm) were taken for each sample at 25° C. and then with each increase in 1° C.

Thermal transitions (melting temperatures, Tm) were obtained using the corresponding temperature of the first derivative of the minimum of fluorescence. The minimum of the negative first derivative trace from the melting curve (or dissociation curve) was calculated using MxPro software provided with RT-PCR system. Tm is defined as a midpoint in a thermal melt and represents a temperature at which the free energy of the native and non-native forms of a protein are equivalent. A summary of the results obtained are noted in FIG. 11. The sensitivity of the assay was +/−0.5° C.

For most proteins, solution pH determines the type and total charge on the protein, and thus, may affect electrostatic interactions and overall stability. For adjuvanted proteins the solution pH and buffer species have a strong effect on microenvironment pH at the surface of the aluminum adjuvants which could ultimately influence the degradation rate of proteins adsorbed to aluminum adjuvants.

All three proteins were 90 to 100% adsorbed to aluminum hydroxide in the range of pH under study. In aluminum phosphate, the adsorption of PcpA was higher than 80% while PhtD and PlyD1 (each an acidic protein) were negligibly adsorbed to the adjuvant above pH 5 (data not shown).

FIG. 11 shows the effect of pH on each of the 3 antigens when formulated with adjuvant and in unadjuvanted controls. The unadjuvanted antigens displayed their distinctive pH stability profile. PcpA showed steady Tm values on a broad pH range from 6.0 to 9.0 with decreasing Tm values as the pH was dropped from 6.0 to 5.0. On the other hand, the thermal stability of unadjuvanted PhtD and PlyD 1 appeared maximized under acidic pHs (see FIG. 11). The thermal stability profiles of the unadjuvanted proteins were significantly modified as a result of the addition of an aluminum adjuvant. As compared to the unadjuvanted control, aluminum hydroxide, appeared to decrease the stability of all three proteins at relatively high and low pH values showing a bell-shaped curve as the pH was increased from 5 to 9 with a maximum stability at near neutral pH. These data show that the pretreatment of AlOOH with 2 mM phosphate significantly improved the stability of all three antigens at high and low pH as compared to untreated AlOOH (FIG. 11A-C). No significant differences were observed in the pH range of 6.0-7.5

Compared to unadjuvanted control, no major changes were observed on the Tm vs pH profile of PcpA and PlyDI when aluminum phosphate was used as the adjuvant (FIG. 11A and 11C). In the case of PhtD adjuvanted with AP, as compared to the unadjvanted control, a significant decrease in the Tm was observed at pH lower than 6 (FIG. 11B).

Example 11

The Effect of Various Excipients on the Stability of a Number of Formulations

A screening of 18 GRAS (generally regarded as safe) compounds at various concentrations was performed. An assay was used to screen for compounds that increase the thermal stability of each protein under evaluation (i.e., PcpA, PhtD and a detoxified pneumolysin mutant (PlyD1, as described in PCT/CA/2009/001843: Modified PLY Nucleic Acids and Polypeptides, as SEQ ID NO:44)).

Each of the protein antigens were recombinantly expressed in $E.$ $coli$ and purified by serial column chromatography following conventional purification protocols substantially as described in Example 1, for PhtD and PcpA and as described in PCT/CA/2009/001843 (as SEQ ID NO:44)

for PlyD 1 (the sequence for which is noted herein as SEQ ID NO:9). Protein purity for all three antigens was typically higher than 90% as evaluated by RP-HPLC and SDS-PAGE. Proteins bulks were supplied at approximately 1 mg/mL in 10 mM Tris, pH 7.4 containing 150 mM sodium chloride. Each protein was diluted to the desired concentration (100 μg/mL PcpA; 100 μg/mL PhtD; 200 μg/mL PlyD1) with the appropriate excipient solution (in the concentration noted in Table 11) in 10 mM tris buffer saline, pH 7.5 (TBS), and PTH was added to the protein solutions to achieve a final concentration of 0.6 mg of elemental Al/mL. Control samples (lacking the applicable excipient) were also assayed. SYPRO® Orange, 5000× (Invitrogen, Inc., Carlsbad, Calif.), was diluted to 560× with DMSO (Sigma) and then added to the adjuvanted protein solutions. In all cases optimal dilution of SYPRO-Orange was 10× from a commercial stock solution of 5000×.

Assays were performed in a 96 well polypropylene plate (Stratagene, La Jolla, CA) using a real-time polymerase chain reaction (RT-PCR) instrument (Mx3005p QPCR Systems, Stratagene, La Jolla, Calif.). A sample volume of approximately 100 μL was added to each well and the plate was then capped with optical cap strips (Stratagene, La Jolla, Calif.) to prevent sample evaporation. Plates were centrifuged at 200 g for 1 mM at room temperature in a Contifuge Stratos centrifuge (Heraeus Instruments, England) equipped with a 96 well plate rotor. The plates were then heated at 1° C. per min from 25° C. to 96° C. Fluorescence excitation and emission filters were set at 492 nm and 610 nm, respectively. Fluorescence readings (emission at 610 nm, excitation at 492 nm) were taken for each sample at 25° C. and then with each increase in 1° C.

Thermal transitions (melting temperatures, Tm) were obtained using the corresponding temperature of the first derivative of the minimum of fluorescence. The minimum of the negative first derivative trace from the melting curve (or dissociation curve) was calculated using MxPro software provided with RT-PCR system. Tm is defined as a midpoint in a thermal melt and represents a temperature at which the free energy of the native and non-native forms of a protein are equivalent. The effect of each excipient was assessed as the ΔTm=Tm (sample with protein+compound)−Tm (protein control sample). A summary of the results obtained are noted in Table 13. The sensitivity of the assay was +/−0.5° C.

Polyols, monosaccharides and disaccharides increased the Tm of adjuvanted PlyD1 in a concentration dependant manner with maximum stabilization (i.e., an increase in Tm of about 4° C.) observed at high concentration of sugars. Similar results were detected for each of PcpA and PhtD with the exception of arginine which decreased the Tm of PhtD by about 2° C. The following excipients were found to efficiently increase the thermal stability of all three proteins: sorbitol (20%, 10%), trehalose (20%), dextrose (20%, 10%), sucrose (10%, 5%), and 10% lactose.

The effect of several excipients identified in the screening assays on the physical stability and antigenicity of PcpA stored under stress conditions was also studied to note any correlation with the thermal stability effects noted earlier. PcpA protein was diluted to the desired concentration (e.g., about 100 μg/mL) with the appropriate excipient solution described in the FIG. (10% Sorbitol, 10% Sucrose, 10% Trehalose in 10mM Tris Buffer pH 7.4), and PTH was added to the protein solutions to achieve a final concentration of 0.6 mg of elemental Al/mL. A control sample (lacking excipient) was also included in the study. Samples were stored at 50° C. for a three day period. Protein degradation was evaluated by RP-HPLC and antigenicity was assessed by quantitative, sandwich ELISA. Results are set out in FIGS. 13A and 13B.

The concentration of intact protein was measured by RP-HPLC in an Agilent 1200 HPLC system equipped with a diode array UV detector. Samples were desorbed from the adjuvant in PBS/Zwittergent buffer for 5 h at 37° C. and separated using an ACE C4 column (Advanced Chromatography Technologies, Aberdeen, UK) and a mobile phase gradient of buffer A (0.1% TFA in water) and buffer B (0.1% TFA in CAN) using a gradient of 0.75% of buffer B per minute over 30 min at a flow rate of 1 ml/min. Proteins were monitored by UV absorbance at 210 nm and quantitated against a 5-point linear calibration curve produced with external standards.

The quantitative antigen ELISA sandwich was used to evaluate antigenicity of PcpA formulations at time zero and after 3 days of incubation at 50° C. A rabbit IgG anti-PcpA sera was used for antigen capture, and a well characterized monoclonal anti-PcpA for detection. Briefly, 96 well plates were coated with rabbit anti-PhtD IgG at a concentration of 2 μg/mL in 0.05 M $Na_2CO_3$/$NaHCO_3$ buffer for 18 hours at room temperature (RT), and blocked with 1% BSA/PBS for 1 hour at RT followed by 2 washes in a washing buffer of PBS/0.1% Tween 20 (WB). Two-fold dilutions of test samples, an internal control and a reference standard of purified PcpA of known concentration were prepared in 0.1% BSA/PBS/0.1% Tween 20 (SB), added to wells and incubated at RT for 1 hour followed by 5 washes in WB. Detecting primary mAb was diluted in SB to a concentration of 0.1 μg/mL, and incubated for 1 hour at RT and followed by 5 washes in WB, and addition of F(ab')2 Donkey anti-mouse IgG (H+L) specific at 1/40K dilution in SB. Following 5 washes in WB, TMB/$H_2O_2$ substrate is added to the wells, and incubated for 10 minutes at RT. The reaction is stopped by the addition of 1M $H_2SO_4$. ELISA plates were read in a plate reader (SpectraMax, M5, Molecular Devices, Sunnyvale, Calif.) at A450/540 nm, and test sample data is calculated by extrapolation from a standard curve using 4-parameter logistic using the software SoftMax PRO.

As shown in FIG. 12A, data derived from RP-HPLC showed that those excipients that increased the Tm of adjuvanted PcpA also decreased the protein's rate of degradation at 50° C. over a three day period. The greatest stability as determined by percent recovery of the PcpA protein over time was provided by 10% sorbitol (as shown in FIG. 12A). The antigenicity of adjuvanted PcpA was also preserved by these excipients (as shown in FIG. 12B). In good correlation with RP-HPLC results, sorbitol appeared to preserve antigenicity to a higher degree than sucrose or trehalose.

The addition of 10% sorbitol, 10% sucrose, or 10% trehalose significantly decreased the rate constant at 50° C. and increased the half life of PcpA when compared to that of the control sample without excipients (Table 14). The buffer pH of 9.0 decreased the Tm of the protein, but accelerated degradation (i.e., increased the rate constant) at 50° C. as compared to that of the control (Table 14). Altogether, these results suggest a good correlation between thermal stability detected by the assay, physical stability detected by RP-HPLC and antigenicity detected by ELISA.

In view of the results obtained in these studies, sorbitol, sucrose, dextrose, lactose and/or trehalose are examples of excipients that may be included in monovalent and multivalent (e.g., bivalent, trivalent) formulations of PcpA, PhtD and detoxified pneumolysin proteins (such as, PlyD1) adjuvanted with PTH to increase physical stability.

TABLE 13

Effect of GRAS excipients on Tm (as assessed by monitoring fluorescence emission over a temperature range). Compounds that increase thermal stability provide a positive Tm difference value.

| Excipient | PcpA Tm (°C.) | PcpA ΔTm (ΔTm = Tm (excipient) − Tm (control) | PhtD Tm (°C.) | PhtD ΔTm (ΔTm = Tm (excipient) − Tm (control) | Ply mutant Tm (°C.) | Ply mutant ΔTm (ΔTm = Tm (excipient) − Tm (control) |
|---|---|---|---|---|---|---|
| Control | 56.7 | 0.0 | 58.7 | 0.0 | 49.7 | 0.0 |
| 5% Sucrose | 57.0 | 0.3 | 60.0 | 1.3 | 50.4 | 0.7 |
| 10% Sucrose | 58.4 | 1.7 | 60.0 | 1.3 | 52.1 | 2.4 |
| 20% Sucrose | 60.0 | 3.3 | 61.7 | 3.0 | 52.5 | 2.8 |
| 5% Dextrose | 57.7 | 1.0 | 58.7 | 0.0 | 49.7 | 0.0 |
| 10% Dextrose | 58.7 | 2.0 | 59.7 | 1.0 | 51.7 | 2.0 |
| 20% Dextrose | 60.7 | 4.0 | 60.7 | 2.0 | 53.7 | 4.0 |
| 5% Trehalose | 56.7 | 0.0 | 58.7 | 0.0 | 49.7 | 0.0 |
| 10% Trehalose | 57.7 | 1.0 | 58.7 | 0.0 | 50.7 | 1.0 |
| 20% Trehalose | 58.7 | 2.0 | 60.7 | 2.0 | 51.7 | 2.0 |
| 5% Mannitol | 56.7 | 0.0 | 58.7 | 0.0 | 49.7 | 0.0 |
| 10% Mannitol | 56.7 | 0.0 | 58.7 | 0.0 | 49.7 | 0.0 |
| 20% Mannitol | 56.7 | 0.0 | 58.7 | 0.0 | 50.7 | 1.0 |
| 5% Sorbitol | 56.7 | 0.0 | 58.7 | 0.0 | 49.7 | 0.0 |
| 10% Sorbitol | 58.7 | 2.0 | 59.7 | 1.0 | 51.7 | 2.0 |
| 20% Sorbitol | 60.7 | 4.0 | 60.7 | 2.0 | 53.7 | 4.0 |
| 5% Glycerol | 56.7 | 0.0 | 58.7 | 0.0 | 49.7 | 0.0 |
| 10% Glycerol | 56.7 | 0.0 | 58.7 | 0.0 | 49.7 | 0.0 |
| 20% Glycerol | 56.7 | 0.0 | 58.7 | 0.0 | 49.7 | 0.0 |
| 0.05M Lysine | 56.7 | 0.0 | 58.7 | 0.0 | 49.7 | 0.0 |
| 0.1M Lysine | 56.7 | 0.0 | 58.7 | 0.0 | 49.7 | 0.0 |
| 5% Lactose | 56.7 | 0.0 | 58.7 | 0.0 | 50.7 | 1.0 |
| 10% Lactose | 58.7 | 2.0 | 60.7 | 2.0 | 50.7 | 1.0 |
| 0.05M Proline | 56.7 | 0.0 | 58.7 | 0.0 | 48.7 | −1.0 |
| 0.1M Proline | 56.7 | 0.0 | 58.7 | 0.0 | 48.7 | −1.0 |
| 0.05M Glycine | 56.7 | 0.0 | 58.7 | 0.0 | 50.7 | 1.0 |
| 0.1M Glycine | 56.7 | 0.0 | 58.7 | 0.0 | 50.7 | 1.0 |
| 0.01M Aspartate | 56.7 | 0.0 | 58.7 | 0.0 | 48.7 | −1.0 |
| 0.05M Glutamate | 56.7 | 0.0 | 58.7 | 0.0 | 50.7 | 1.0 |
| 0.05M Lactic acid | 56.7 | 0.0 | 58.7 | 0.0 | 49.7 | 0.0 |
| 0.05M Malic Acid | 58.7 | 2.0 | 58.7 | 0.0 | 48.7 | −1.0 |
| 0.05M Arginine | 56.7 | 0.0 | 58.7 | 0.0 | 48.7 | −1.0 |
| 0.1M Arginine | 56.7 | 0.0 | 56.7 | −2.0 | 48.7 | −1.0 |
| 0.05M Diethanolamine | 56.7 | 0.0 | 58.7 | 0.0 | 48.7 | −1.0 |
| 0.1M Diethanolamine | 56.7 | 0.0 | 58.7 | 0.0 | 48.7 | −1.0 |
| 0.05M Histidine | 56.7 | 0.0 | 58.7 | 0.0 | 50.7 | 1.0 |
| 0.1M Histidine | 56.7 | 0.0 | 58.7 | 0.0 | 49.7 | 0.0 |
| 0.15M Taurine | 56.7 | 0.0 | 58.7 | 0.0 | 50.7 | 1.0 |

TABLE 14

Rate constant values from stability data of formulations incubated at 50° C.

| Formulation | k at 50° C. (µg · mL$^{-1}$ · day$^{-1}$) | Half life at 50° C. (days) | R$^2$ |
|---|---|---|---|
| 10% Sorbitol | 7.5 | 7.3 | 0.99 |
| 10% Trehalose | 9.8 | 5.6 | 0.95 |
| 10% Sucrose | 10.9 | 5.1 | 0.98 |
| Control (TBS pH 7.4) | 13.4 | 4.1 | 0.94 |
| TBS pH9 | 16.2 | 3.4 | 0.93 |

Rate constant for formulations incubated at 50° C. were calculated by fitting the RP-HPLC stability data presented in FIG. 12A using zero order kinetics equation (1) [A$_t$] = -kt + [A$_0$], where A$_t$ is the concentration of the antigen at a given time, A$_0$ is the initial protein concentration in µg/mL and t is the time in days. R$^2$ is reported for the linear fit of the data using equation (1).

The invention claimed is:

1. An immunogenic composition comprising at least one antigen adsorbed to an aluminum compound comprising hydroxyl groups that has been treated with about 2 mM to about 80 mM phosphate, the at least one antigen being adsorbed to the treated compound at about neutral pH, wherein:
the treatment of the aluminum compound with about 2 mM to about 80 mM phosphate prior to adsorption increases the stability of the at least one antigen adsorbed relative to a composition where the at least one antigen is adsorbed to an untreated aluminum compound comprising hydroxyl groups; and the at least one antigen is selected from PcpA, a *S. pneumoniae* protein from the polyhistidine triad family (PhtX) and pneumolysin.

2. The immunogenic composition of claim 1 wherein the aluminum compound is aluminum hydroxide adjuvant.

3. The immunogenic composition of claim 2 wherein the adjuvant is aluminum oxyhydroxide.

4. The immunogenic composition of claim 1 comprising about 0.28 mg/ml to 1.68 mg/ml elemental aluminum.

5. The composition of claim 1, wherein the at least one antigen is a protein or a polysaccharide, or a protein polysaccharide conjugate.

6. The composition of claim 1, wherein the concentration of elemental phosphorus is between about 2.0 mM and about 20 mM.

7. The composition of claim 1 wherein the composition further includes a buffer.

8. The composition of claim 1 wherein the pH of the composition is between about 6.4 and about 8.4.

9. The composition of claim 8 wherein the pH of the composition is about 7.4.

10. The composition of claim 1 wherein the composition comprises more than one antigen.

11. The composition of claim 10 wherein the aluminum compound is aluminum hydroxide adjuvant.

12. The composition of claim 11 wherein the composition comprises more than one antigens adsorbed to the aluminum hydroxide adjuvant.

13. The composition of claim 1 wherein the PhtX antigen is PhtD and the pneumolysin antigen is an enzymatically inactive pneumolysin.

14. The composition of claim 10 wherein one antigen is PepA and a second antigen is PhtD.

15. The composition of claim 14 wherein the composition further comprises an enzymatically inactive pneumolysin.

16. The composition of claim 15 wherein the enzymatically inactive pneumolysin is a mutant pneumolysin protein.

17. The composition of claim 16, wherein the mutant pneumolysin protein is PlyD1, SEQ ID NO:9.

18. A method for preparing an immunogenic composition comprising: (a) treating an aluminum compound comprising hydroxyl groups with about 2 mM to about 80 mM phosphate; and (b) mixing the preparation in step (a) with at least one antigen selected from PcpA, a *S. pneumoniae* protein from the polyhistidine triad family (PhtX), and pneumolysin at about neutral pH, wherein the mixing of the preparation in step (a) with at least one antigen increases the stability of the at least one antigen relative to a composition where the at least one antigen is mixed with an untreated aluminum compound comprising hydroxyl groups.

19. A method of preventing the development of a disease associated with *S. pneumoniae* infection in a subject comprising administering to the subject a therapeutically effective amount of the immunogenic composition of claim 1.

20. The method of claim 19 wherein the route of administration is subcutaneous or intramuscular.

21. A method of treating a disease associated with *S. pneumoniae* infection in a subject comprising administering to the subject a therapeutically effective amount of the immunogenic composition of claim 1.

22. A method of raising an immune response in a mammal comprising the step of administering an effective amount of the composition of claim 1.

23. A vaccine comprising the composition of claim 1 and a pharmaceutically acceptable excipient.

24. The immunogenic composition of claim 1 wherein the composition is in liquid form.

25. The method of claim 19 wherein the PhtX antigen is PhtD and the pneumolysin antigen is an enzymatically inactive pneumolysin.

26. The method of claim 21 wherein the PhtX antigen is PhtD and the pneumolysin antigen is an enzymatically inactive pneumolysin.

27. The composition of claim 1 wherein PcpA has the amino acid sequence of SEQ ID NO:7.

28. The composition of claim 14 wherein PcpA has the amino acid sequence of SEQ ID NO:7.

29. The method of claim 18 wherein PcpA has the amino acid sequence of SEQ ID NO:7.

30. The method of claim 19 wherein PcpA has the amino acid sequence of SEQ ID NO:7.

31. The method of claim 21 wherein PcpA has the amino acid sequence of SEQ ID NO:7.

32. The composition of claim 1 wherein the PhtX is PhtD having the amino acid sequence of SEQ ID NO:5.

33. The composition of claim 13 wherein PhtD has the amino acid sequence of SEQ ID NO:5.

34. The composition of claim 14 wherein PhtD has the amino acid sequence of SEQ ID NO:5.

35. The method of claim 18 wherein PhtX is PhtD having the amino acid sequence of SEQ ID NO:5.

36. The method of claim 19 wherein PhtX is PhtD having the amino acid sequence of SEQ ID NO:5.

37. The method of claim 21 wherein the PhtX is PhtD having the amino acid sequence of SEQ ID NO:5.

38. The method of claim 25 wherein PhtX is PhtD having the amino acid sequence of SEQ ID NO:5.

39. The method of claim 26 wherein the PhtX is PhtD having the amino acid sequence of SEQ ID NO:5.

40. The method of claim 25, wherein the enzymatically inactive pneumolysin protein is PlyD1, SEQ ID NO:9.

41. The method of claim 26, wherein the enzymatically inactive pneumolysin protein is PlyD1, SEQ ID NO:9.

42. The composition of claim 1 wherein PcpA has the amino acid sequence of SEQ ID NO:7, PhtX is PhtD having the amino acid sequence of SEQ ID NO:5, and pneumolysin has the amino acid sequence of SEQ ID NO:9.

43. The method of claim 18 wherein PcpA has the amino acid sequence of SEQ ID NO:7, PhtX is PhtD having the amino acid sequence of SEQ ID NO:5, and pneumolysin has the amino acid sequence of SEQ ID NO:9.

44. The method of claim 19 wherein PcpA has the amino acid sequence of SEQ ID NO:7, PhtX is PhtD having the amino acid sequence of SEQ ID NO:5, and pneumolysin has the amino acid sequence of SEQ ID NO:9.

45. The method of claim 21 wherein PcpA has the amino acid sequence of SEQ ID NO:7, PhtX is PhtD having the amino acid sequence of SEQ ID NO:5, and pneumolysin has the amino acid sequence of SEQ ID NO:9.

46. The immunogenic composition of claim 4 comprising about 0.56 mg/ml elemental aluminum.

47. The composition of claim 1 comprising up to 46μg/ml of one of PcpA, PhtD or pneumolysin; and an adjuvant comprising about 0.56 mg/ml elemental aluminum.

48. The composition of claim 47 wherein PcpA has the amino acid sequence of SEQ ID NO:7, PhtX is PhtD having the amino acid sequence of SEQ ID NO:5, and pneumolysin has the amino acid sequence of SEQ ID NO:9.

49. The composition of claim 1 comprising up to 100μg/ml each of at least two of PcpA, PhtD and pneumolysin; and an adjuvant comprising about 0.56 mg/ml elemental aluminum.

50. The composition of claim 49 wherein PcpA has the amino acid sequence of SEQ ID NO:7, PhtX is PhtD having the amino acid sequence of SEQ ID NO:5, and pneumolysin has the amino acid sequence of SEQ ID NO:9.

51. The composition of claim 1 comprising up to 100μg/ml each of PcpA, PhtD and pneumolysin; and an adjuvant comprising about 0.56 mg/ml elemental aluminum.

52. The composition of claim 51 wherein PcpA has the amino acid sequence of SEQ ID NO:7, PhtX is PhtD having the amino acid sequence of SEQ ID NO:5, and pneumolysin has the amino acid sequence of SEQ ID NO:9.

53. The composition of claim 4 wherein the phosphate to elemental aluminum ratio is 0.1.

* * * * *

SEQUENCE LISTING

<160> NUMBER OF SEQ ID NOS: 10

<210> SEQ ID NO 1
<211> LENGTH: 838
<212> TYPE: PRT
<213> ORGANISM: Streptococcus pneumoniae

<400> SEQUENCE: 1

```
Met Lys Ile Asn Lys Lys Tyr Leu Ala Gly Ser Val Ala Val Leu Ala
1               5                   10                  15

Leu Ser Val Cys Ser Tyr Glu Leu Gly Arg His Gln Ala Gly Gln Val
            20                  25                  30

Lys Lys Glu Ser Asn Arg Val Ser Tyr Ile Asp Gly Asp Gln Ala Gly
            35                  40                  45

Gln Lys Ala Glu Asn Leu Thr Pro Asp Glu Val Ser Lys Arg Glu Gly
50                  55                  60

Ile Asn Ala Glu Gln Ile Val Ile Lys Ile Thr Asp Gln Gly Tyr Val
65                  70                  75                  80

Thr Ser His Gly Asp His Tyr His Tyr Tyr Asn Gly Lys Val Pro Tyr
                85                  90                  95

Asp Ala Ile Ile Ser Glu Glu Leu Leu Met Lys Asp Pro Asn Tyr Gln
                100                 105                 110

Leu Lys Asp Ser Asp Ile Val Asn Glu Ile Lys Gly Gly Tyr Val Ile
            115                 120                 125

Lys Val Asp Gly Lys Tyr Tyr Val Tyr Leu Lys Asp Ala Ala His Ala
130                 135                 140

Asp Asn Ile Arg Thr Lys Glu Glu Ile Lys Arg Gln Lys Gln Glu His
145                 150                 155                 160

Ser His Asn His Asn Ser Arg Ala Asp Asn Ala Val Ala Ala Ala Arg
                165                 170                 175

Ala Gln Gly Arg Tyr Thr Thr Asp Asp Gly Tyr Ile Phe Asn Ala Ser
                180                 185                 190

Asp Ile Ile Glu Asp Thr Gly Asp Ala Tyr Ile Val Pro His Gly Asp
                195                 200                 205

His Tyr His Tyr Ile Pro Lys Asn Glu Leu Ser Ala Ser Glu Leu Ala
        210                 215                 220

Ala Ala Glu Ala Tyr Trp Asn Gly Lys Gln Gly Ser Arg Pro Ser Ser
225                 230                 235                 240

Ser Ser Ser Tyr Asn Ala Asn Pro Val Gln Pro Arg Leu Ser Glu Asn
            245                 250                 255

His Asn Leu Thr Val Thr Pro Thr Tyr His Gln Asn Gly Glu Asn
                260                 265                 270

Ile Ser Ser Leu Leu Arg Glu Leu Tyr Ala Lys Pro Leu Ser Glu Arg
            275                 280                 285

His Val Glu Ser Asp Gly Leu Ile Phe Asp Pro Ala Gln Ile Thr Ser
            290                 295                 300

Arg Thr Ala Arg Gly Val Ala Val Pro His Gly Asn His Tyr His Phe
305                 310                 315                 320

Ile Pro Tyr Glu Gln Met Ser Glu Leu Glu Lys Arg Ile Ala Arg Ile
            325                 330                 335

Ile Pro Leu Arg Tyr Arg Ser Asn His Trp Val Pro Asp Ser Arg Pro
            340                 345                 350

Glu Gln Pro Ser Pro Gln Ser Thr Pro Glu Pro Ser Pro Ser Leu Gln
            355                 360                 365

Pro Ala Pro Asn Pro Gln Pro Ala Pro Ser Asn Pro Ile Asp Glu Lys
            370                 375                 380

Leu Val Lys Glu Ala Val Arg Lys Val Gly Asp Gly Tyr Val Phe Glu
385                 390                 395                 400

Glu Asn Gly Val Ser Arg Tyr Ile Pro Ala Lys Asp Leu Ser Ala Glu
                405                 410                 415
```

-continued

Thr Ala Ala Gly Ile Asp Ser Lys Leu Ala Lys Gln Glu Ser Leu Ser
            420                 425                 430

His Lys Leu Gly Ala Lys Lys Thr Asp Leu Pro Ser Ser Asp Arg Glu
        435                 440                 445

Phe Tyr Asn Lys Ala Tyr Asp Leu Leu Ala Arg Ile His Gln Asp Leu
    450                 455                 460

Leu Asp Asn Lys Gly Arg Gln Val Asp Phe Glu Val Leu Asp Asn Leu
465                 470                 475                 480

Leu Glu Arg Leu Lys Asp Val Ser Ser Asp Lys Val Lys Leu Val Asp
                485                 490                 495

Asp Ile Leu Ala Phe Leu Ala Pro Ile Arg His Pro Glu Arg Leu Gly
            500                 505                 510

Lys Pro Asn Ala Gln Ile Thr Tyr Thr Asp Asp Glu Ile Gln Val Ala
        515                 520                 525

Lys Leu Ala Gly Lys Tyr Thr Thr Glu Asp Gly Tyr Ile Phe Asp Pro
    530                 535                 540

Arg Asp Ile Thr Ser Asp Glu Gly Asp Ala Tyr Val Thr Pro His Met
545                 550                 555                 560

Thr His Ser His Trp Ile Lys Lys Asp Ser Leu Ser Glu Ala Glu Arg
                565                 570                 575

Ala Ala Ala Gln Ala Tyr Ala Lys Glu Lys Gly Leu Thr Pro Pro Ser
            580                 585                 590

Thr Asp His Gln Asp Ser Gly Asn Thr Glu Ala Lys Gly Ala Glu Ala
        595                 600                 605

Ile Tyr Asn Arg Val Lys Ala Ala Lys Lys Val Pro Leu Asp Arg Met
610                 615                 620

Pro Tyr Asn Leu Gln Tyr Thr Val Glu Val Lys Asn Gly Ser Leu Ile
625                 630                 635                 640

Ile Pro His Tyr Asp His Tyr His Asn Ile Lys Phe Glu Trp Phe Asp
                645                 650                 655

Glu Gly Leu Tyr Glu Ala Pro Lys Gly Tyr Ser Leu Glu Asp Leu Leu
            660                 665                 670

Ala Thr Val Lys Tyr Tyr Val Glu His Pro Asn Glu Arg Pro His Ser
        675                 680                 685

Asp Asn Gly Phe Gly Asn Ala Ser Asp His Val Arg Lys Asn Lys Ala
    690                 695                 700

Asp Gln Asp Ser Lys Pro Asp Glu Asp Lys Glu His Asp Glu Val Ser
705                 710                 715                 720

Glu Pro Thr His Pro Glu Ser Asp Glu Lys Glu Asn His Ala Gly Leu
                725                 730                 735

Asn Pro Ser Ala Asp Asn Leu Tyr Lys Pro Ser Thr Asp Thr Glu Glu
            740                 745                 750

Thr Glu Glu Glu Ala Glu Asp Thr Thr Asp Glu Ala Glu Ile Pro Gln
        755                 760                 765

Val Glu Asn Ser Val Ile Asn Ala Lys Ile Ala Asp Ala Glu Ala Leu
    770                 775                 780

Leu Glu Lys Val Thr Asp Pro Ser Ile Arg Gln Asn Ala Met Glu Thr
785                 790                 795                 800

Leu Thr Gly Leu Lys Ser Ser Leu Leu Leu Gly Thr Lys Asp Asn Asn
                805                 810                 815

Thr Ile Ser Ala Glu Val Asp Ser Leu Leu Ala Leu Leu Lys Glu Ser
            820                 825                 830

Gln Pro Ala Pro Ile Gln

<210> SEQ ID NO 2
<211> LENGTH: 641
<212> TYPE: PRT
<213> ORGANISM: Streptococcus pneumoniae

<400> SEQUENCE: 2

```
Met Lys Lys Thr Thr Ile Leu Ser Leu Thr Ala Ala Val Ile Leu
1               5                   10                  15

Ala Ala Tyr Val Pro Asn Glu Pro Ile Leu Ala Asp Thr Pro Ser Ser
            20                  25                  30

Glu Val Ile Lys Glu Thr Lys Val Gly Ser Ile Ile Gln Gln Asn Asn
        35                  40                  45

Ile Lys Tyr Lys Val Leu Thr Val Glu Gly Asn Ile Arg Thr Val Gln
    50                  55                  60

Val Gly Asn Gly Val Thr Pro Val Glu Phe Glu Ala Gly Gln Asp Gly
65                  70                  75                  80

Lys Pro Phe Thr Ile Pro Thr Lys Ile Thr Val Gly Asp Lys Val Phe
                85                  90                  95

Thr Val Thr Glu Val Ala Ser Gln Ala Phe Ser Tyr Tyr Pro Asp Glu
            100                 105                 110

Thr Gly Arg Ile Val Tyr Tyr Pro Ser Ser Ile Thr Ile Pro Ser Ser
        115                 120                 125

Ile Lys Lys Ile Gln Lys Lys Gly Phe His Gly Ser Lys Ala Lys Thr
130                 135                 140

Ile Ile Phe Asp Lys Gly Ser Gln Leu Glu Lys Ile Glu Asp Arg Ala
145                 150                 155                 160

Phe Asp Phe Ser Glu Leu Glu Glu Ile Glu Leu Pro Ala Ser Leu Glu
                165                 170                 175

Tyr Ile Gly Thr Ser Ala Phe Ser Phe Ser Gln Lys Leu Lys Lys Leu
            180                 185                 190

Thr Phe Ser Ser Ser Lys Leu Glu Leu Ile Ser His Glu Ala Phe
        195                 200                 205

Ala Asn Leu Ser Asn Leu Glu Lys Leu Thr Leu Pro Lys Ser Val Lys
210                 215                 220

Thr Leu Gly Ser Asn Leu Phe Arg Leu Thr Thr Ser Leu Lys His Val
225                 230                 235                 240

Asp Val Glu Glu Gly Asn Glu Ser Phe Ala Ser Val Asp Gly Val Leu
                245                 250                 255

Phe Ser Lys Asp Lys Thr Gln Leu Ile Tyr Tyr Pro Ser Gln Lys Asn
            260                 265                 270

Asp Glu Ser Tyr Lys Thr Pro Lys Glu Thr Lys Glu Leu Ala Ser Tyr
        275                 280                 285

Ser Phe Asn Lys Asn Ser Tyr Leu Lys Lys Leu Glu Leu Asn Glu Gly
    290                 295                 300

Leu Glu Lys Ile Gly Thr Phe Ala Phe Ala Asp Ala Ile Lys Leu Glu
305                 310                 315                 320

Glu Ile Ser Leu Pro Asn Ser Leu Glu Thr Ile Glu Arg Leu Ala Phe
                325                 330                 335

Tyr Gly Asn Leu Glu Leu Lys Glu Leu Ile Leu Pro Asp Asn Val Lys
            340                 345                 350

Asn Phe Gly Lys His Val Met Asn Gly Leu Pro Lys Leu Lys Ser Leu
        355                 360                 365
```

```
Thr Ile Gly Asn Asn Ile Asn Ser Leu Pro Ser Phe Phe Leu Ser Gly
        370                 375                 380

Val Leu Asp Ser Leu Lys Glu Ile His Ile Lys Asn Lys Ser Thr Glu
385                 390                 395                 400

Phe Ser Val Lys Lys Asp Thr Phe Ala Ile Pro Glu Thr Val Lys Phe
                405                 410                 415

Tyr Val Thr Ser Glu His Ile Lys Asp Val Leu Lys Ser Asn Leu Ser
            420                 425                 430

Thr Ser Asn Asp Ile Ile Val Glu Lys Val Asp Asn Ile Lys Gln Glu
        435                 440                 445

Thr Asp Val Ala Lys Pro Lys Lys Asn Ser Asn Gln Gly Val Val Gly
450                 455                 460

Trp Val Lys Asp Lys Gly Leu Trp Tyr Tyr Leu Asn Glu Ser Gly Ser
465                 470                 475                 480

Met Ala Thr Gly Trp Val Lys Asp Lys Gly Leu Trp Tyr Tyr Leu Asn
                485                 490                 495

Glu Ser Gly Ser Met Ala Thr Gly Trp Val Lys Asp Lys Gly Leu Trp
            500                 505                 510

Tyr Tyr Leu Asn Glu Ser Gly Ser Met Ala Thr Gly Trp Val Lys Asp
        515                 520                 525

Lys Gly Leu Trp Tyr Tyr Leu Asn Glu Ser Gly Ser Met Ala Thr Gly
            530                 535                 540

Trp Val Lys Asp Lys Gly Leu Trp Tyr Tyr Leu Asn Glu Ser Gly Ser
545                 550                 555                 560

Met Ala Thr Gly Trp Val Lys Asp Lys Gly Leu Trp Tyr Tyr Leu Asn
                565                 570                 575

Glu Ser Gly Ser Met Ala Thr Gly Trp Val Lys Asp Lys Gly Leu Trp
            580                 585                 590

Tyr Tyr Leu Asn Glu Ser Gly Ser Met Ala Thr Gly Trp Phe Thr Val
        595                 600                 605

Ser Gly Lys Trp Tyr Tyr Thr Tyr Asn Ser Gly Asp Leu Leu Val Asn
            610                 615                 620

Thr Thr Thr Pro Asp Gly Tyr Arg Val Asn Ala Asn Gly Glu Trp Val
625                 630                 635                 640

Gly

<210> SEQ ID NO 3
<211> LENGTH: 2514
<212> TYPE: DNA
<213> ORGANISM: Streptococcus pneumoniae

<400> SEQUENCE: 3
atgaaaatca ataaaaaata tctagcaggt tcagtggcag tccttgccct aagtgtttgt      60
tcctatgaac ttggtcgtca ccaagctggt caggttaaga agagtctaa tcgagtttct      120 tatatagatg gtgatcaggc tggtcaaaag gcagaaaatt tgacaccaga tgaagtcagt     180
aagagagagg ggatcaacgc cgaacaaatt gttatcaaga ttacggatca aggttatgtg     240
acctctcatg gagaccatta tcattactat aatggcaagg ttccttatga tgccatcatc    300
agtgaagaac ttctcatgaa agatccgaat tatcagttga aggattcaga cattgtcaat    360
gaaatcaagg gtggctatgt gattaaggta gacggaaaat actatgttta ccttaaagat    420
gcggcccatg cggacaatat tcggacaaaa gaagagatta acgtcagaa gcaggaacac    480 agtcataatc ataactcaag agcagataat gctgttgctg cagccagagc ccaaggacgt    540
```

| tatacaacgg atgatgggta tatcttcaat gcatctgata tcattgagga cacgggtgat | 600 |
| gcttatatcg ttcctcacgg cgaccattac cattacattc ctaagaatga gttatcagct | 660 |
| agcgagttag ctgctgcaga agcctattgg aatgggaagc agggatctcg tccttcttca | 720 |
| agttctagtt ataatgcaaa tccagttcaa ccaagattgt cagagaacca caatctgact | 780 |
| gtcactccaa cttatcatca aaatcaaggg gaaaacattt caagccttt acgtgaattg | 840 |
| tatgctaaac ccttatcaga acgccatgta gaatctgatg gccttatttt cgacccagcg | 900 |
| caaatcacaa gtcgaaccgc cagaggtgta gctgtccctc atggtaacca ttaccacttt | 960 |
| atcccttatg aacaaatgtc tgaattggaa aaacgaattg ctcgtattat tccccttcgt | 1020 |
| tatcgttcaa accattgggt accagattca agaccagaac aaccaagtcc acaatcgact | 1080 |
| ccggaaccta gtccaagtct gcaacctgca ccaaatcctc aaccagctcc aagcaatcca | 1140 |
| attgatgaga aattggtcaa agaagctgtt cgaaaagtag gcgatggtta tgtctttgag | 1200 |
| gagaatggag tttctcgtta tcccagcc aaggatcttt cagcagaaac agcagcaggc | 1260 |
| attgatagca aactggccaa gcaggaaagt ttatctcata gctaggagc taagaaaact | 1320 |
| gacctcccat ctagtgatcg agaattttac aataaggctt atgacttact agcaagaatt | 1380 |
| caccaagatt tacttgataa taaaggtcga caagttgatt tgaggtttt ggataacctg | 1440 |
| ttggaacgac tcaaggatgt ctcaagtgat aaagtcaagt tagtggatga tattcttgcc | 1500 |
| ttcttagctc cgattcgtca tccagaacgt ttaggaaaac caaatgcgca aattacctac | 1560 |
| actgatgatg agattcaagt agccaagttg gcaggcaagt acacaacaga gacggttat | 1620 |
| atctttgatc ctcgtgatat aaccagtgat gagggggatg cctatgtaac tccacatatg | 1680 |
| acccatagcc actggattaa aaagatagt ttgtctgaag ctgagagagc ggcagcccag | 1740 |
| gcttatgcta aagagaaagg tttgacccct ccttcgacag accatcagga ttcaggaaat | 1800 |
| actgaggcaa aggagcaga agctatctac aaccgcgtga agcagctaa gaaggtgcca | 1860 |
| cttgatcgta tgccttacaa tcttcaatat actgtagaaa tcaaaaacgg tagtttaatc | 1920 |
| atacctcatt atgaccatta ccataacatc aaatttgagt ggtttgacga aggcctttat | 1980 |
| gaggcaccta agggg tatag tcttgaggat ctttttggcga ctgtcaagta ctatgtcgaa | 2040 |
| catccaaacg aacgtccgca ttcagataat ggttttggta acgctagtga ccatgttcgt | 2100 |
| aaaaataagg cagaccaaga tagtaaacct gatgaagata aggaacatga tgaagtaagt | 2160 |
| gagccaactc accctgaatc tgatgaaaaa gagaatcacg ctggtttaaa tccttcagca | 2220 |
| gataatcttt ataaaccaag cactgatacg gaagagacag aggaagaagc tgaagatacc | 2280 |
| acagatgagg ctgaaattcc tcaagtagag aattctgtta ttaacgctaa gatagcagat | 2340 |
| gcggaggcct tgctagaaaa agtaacagat cctagtatta gacaaaatgc tatggagaca | 2400 |
| ttgactggtc taaaaagtag tcttcttctc ggaacgaaag ataataacac tatttcagca | 2460 |
| gaagtagata gtctcttggc tttgttaaaa gaaagtcaac cggctcctat acag | 2514 |

<210> SEQ ID NO 4
<211> LENGTH: 1923
<212> TYPE: DNA
<213> ORGANISM: Streptococcus pneumoniae

<400> SEQUENCE: 4

| atgaaaaaaa ctacaatatt atcattaact acagctgcgg ttattttagc agcatatgtc | 60 |
| cctaatgaac caatcctagc agatactcct agttcggaag taatcaaaga gactaaagtt | 120 |
| ggaagtatta ttcaacaaaa taatatcaaa tataaggttc taactgtaga aggtaacata | 180 |

-continued

```
agaactgttc aagtgggtaa tggagttact cctgtagagt ttgaagctgg tcaagatgga    240
aaaccattca cgattcctac aaaaatcaca gtaggtgata aagtatttac cgttactgaa    300
gtagctagtc aagcttttag ttattatcca gatgaaacag gtagaattgt ctactatcct    360
agctctatta ctatcccatc aagcataaaa aaatacaaa aaaaaggctt ccatggaagt     420
aaagctaaaa ctattatttt tgacaaaggc agtcagctgg agaaaattga agatagagct    480
tttgattttt ctgaattaga agagattgaa ttgcctgcat ctctagaata tattggaaca    540
agtgcatttt cttttagtca aaaattgaaa aagctaacct tttcctcaag ttcaaaatta    600
gaattaatat cacatgaggc ttttgctaat ttatcaaatt tagagaaact aacattacca    660
aaatcggtta aacattagg aagtaatcta tttagactca ctactagctt aaaacatgtt     720
gatgttgaag aaggaaatga atcgtttgcc tcagttgatg gtgttttgtt ttcaaaagat    780
aaaactcaat taatttatta tccaagtcaa aaaaatgacg aaagttataa aacgcctaag    840
gagacaaaag aacttgcatc atattcgttt aataaaaatt cttacttgaa aaaactcgaa    900 tgaatgaag gtttagaaaa aatcggtact tttgcatttg cggatgcgat taaacttgaa    960
gaaattagct taccaaatag tttagaaact attgaacgtt tagccttta cggtaattta   1020 gaattaaaag aacttatatt accagataat gttaaaaatt ttggtaaaca cgttatgaac   1080
ggtttaccaa aattaaaaag tttaacaatt ggtaataata tcaactcatt gccgtccttc   1140
ttcctaagtg gcgtcttaga ttcattaaag gaaattcata ttaagaataa aagtacagag   1200
ttttctgtga aaaagatac atttgcaatt cctgaaactg ttaagttcta tgtaacatca    1260
gaacatataa aagatgttct taaatcaaat ttatctacta gtaatgatat cattgttgaa   1320
aaagtagata atataaaaca agaaactgat gtagctaaac ctaaaaagaa ttctaatcag   1380
ggagtagttg gttgggttaa agacaaaggt ttatggtatt acttaaacga atcaggttca   1440
atggctactg gttgggttaa agacaaaggt ttatggtatt acttaaacga atcaggttca   1500
atggctactg gttgggttaa agacaaaggc ttatggtatt acttaaacga atcaggttca   1560
atggctactg gttgggttaa agacaaaggc ttatggtatt acttaaatga atcaggttca   1620
atggctactg gttgggttaa agacaaaggc ttatggtatt acttaaacga atcaggttca   1680
atggctactg gttgggttaa agacaaaggc ttatggtatt acttaaacga atcaggttca   1740
atggctactg gttgggttaa agacaaaggc ttatggtatt acttaaatga atcaggttca   1800
atggctactg gttggtttac agtttctggt aaatggtact atacctataa ttcaggagat   1860
ttattagtaa acacgactac acccgatggc tatcgagtca atgctaacgg tgagtgggta   1920
gga                                                                 1923
```

<210> SEQ ID NO 5
<211> LENGTH: 820
<212> TYPE: PRT
<213> ORGANISM: Streptococcus pneumoniae

<400> SEQUENCE: 5

```
Met Gly Ser Tyr Glu Leu Gly Arg His Gln Ala Gly Gln Val Lys Lys
1               5                   10                  15

Glu Ser Asn Arg Val Ser Tyr Ile Asp Gly Asp Gln Ala Gly Gln Lys
                20                  25                  30

Ala Glu Asn Leu Thr Pro Asp Glu Val Ser Lys Arg Glu Gly Ile Asn
            35                  40                  45

Ala Glu Gln Ile Val Ile Lys Ile Thr Asp Gln Gly Tyr Val Thr Ser
```

```
                50                  55                  60
        His Gly Asp His Tyr His Tyr Tyr Asn Gly Lys Val Pro Tyr Asp Ala
        65                  70                  75                  80

Ile Ile Ser Glu Glu Leu Leu Met Lys Asp Pro Asn Tyr Gln Leu Lys
                            85                  90                  95

Asp Ser Asp Ile Val Asn Glu Ile Lys Gly Gly Tyr Val Ile Lys Val
                        100                 105                 110

Asp Gly Lys Tyr Tyr Val Tyr Leu Lys Asp Ala Ala His Ala Asp Asn
                    115                 120                 125

Ile Arg Thr Lys Glu Glu Ile Lys Arg Gln Lys Gln Glu His Ser His
                130                 135                 140

Asn His Asn Ser Arg Ala Asp Asn Ala Val Ala Ala Arg Ala Gln
        145                 150                 155                 160

Gly Arg Tyr Thr Thr Asp Asp Gly Tyr Ile Phe Asn Ala Ser Asp Ile
                            165                 170                 175

Ile Glu Asp Thr Gly Asp Ala Tyr Ile Val Pro His Gly Asp His Tyr
                        180                 185                 190

His Tyr Ile Pro Lys Asn Glu Leu Ser Ala Ser Glu Leu Ala Ala Ala
                    195                 200                 205

Glu Ala Tyr Trp Asn Gly Lys Gln Gly Ser Arg Pro Ser Ser Ser Ser
        210                 215                 220

Ser Tyr Asn Ala Asn Pro Val Gln Pro Arg Leu Ser Glu Asn His Asn
        225                 230                 235                 240

Leu Thr Val Thr Pro Thr Tyr His Gln Asn Gln Gly Glu Asn Ile Ser
                            245                 250                 255

Ser Leu Leu Arg Glu Leu Tyr Ala Lys Pro Leu Ser Glu Arg His Val
                        260                 265                 270

Glu Ser Asp Gly Leu Ile Phe Asp Pro Ala Gln Ile Thr Ser Arg Thr
                    275                 280                 285

Ala Arg Gly Val Ala Val Pro His Gly Asn His Tyr His Phe Ile Pro
                290                 295                 300

Tyr Glu Gln Met Ser Glu Leu Glu Lys Arg Ile Ala Arg Ile Ile Pro
        305                 310                 315                 320

Leu Arg Tyr Arg Ser Asn His Trp Val Pro Asp Ser Arg Pro Glu Gln
                            325                 330                 335

Pro Ser Pro Gln Ser Thr Pro Glu Pro Ser Pro Ser Leu Gln Pro Ala
                        340                 345                 350

Pro Asn Pro Gln Pro Ala Pro Ser Asn Pro Ile Asp Glu Lys Leu Val
                    355                 360                 365

Lys Glu Ala Val Arg Lys Val Gly Asp Gly Tyr Val Phe Glu Glu Asn
                370                 375                 380

Gly Val Ser Arg Tyr Ile Pro Ala Lys Asp Leu Ser Ala Glu Thr Ala
        385                 390                 395                 400

Ala Gly Ile Asp Ser Lys Leu Ala Lys Gln Glu Ser Leu Ser His Lys
                            405                 410                 415

Leu Gly Ala Lys Lys Thr Asp Leu Pro Ser Ser Asp Arg Glu Phe Tyr
                        420                 425                 430

Asn Lys Ala Tyr Asp Leu Leu Ala Arg Ile His Gln Asp Leu Leu Asp
                    435                 440                 445

Asn Lys Gly Arg Gln Val Asp Phe Glu Val Leu Asp Asn Leu Leu Glu
                450                 455                 460

Arg Leu Lys Asp Val Ser Ser Asp Lys Val Lys Leu Val Asp Asp Ile
        465                 470                 475                 480
```

Leu Ala Phe Leu Ala Pro Ile Arg His Pro Glu Arg Leu Gly Lys Pro
            485                 490                 495

Asn Ala Gln Ile Thr Tyr Thr Asp Asp Glu Ile Gln Val Ala Lys Leu
        500                 505                 510

Ala Gly Lys Tyr Thr Thr Glu Asp Gly Tyr Ile Phe Asp Pro Arg Asp
    515                 520                 525

Ile Thr Ser Asp Glu Gly Asp Ala Tyr Val Thr Pro His Met Thr His
    530                 535                 540

Ser His Trp Ile Lys Lys Asp Ser Leu Ser Glu Ala Glu Arg Ala Ala
545                 550                 555                 560

Ala Gln Ala Tyr Ala Lys Glu Lys Gly Leu Thr Pro Pro Ser Thr Asp
            565                 570                 575

His Gln Asp Ser Gly Asn Thr Glu Ala Lys Gly Ala Glu Ala Ile Tyr
        580                 585                 590

Asn Arg Val Lys Ala Ala Lys Lys Val Pro Leu Asp Arg Met Pro Tyr
    595                 600                 605

Asn Leu Gln Tyr Thr Val Glu Val Lys Asn Gly Ser Leu Ile Ile Pro
    610                 615                 620

His Tyr Asp His Tyr His Asn Ile Lys Phe Glu Trp Phe Asp Glu Gly
625                 630                 635                 640

Leu Tyr Glu Ala Pro Lys Gly Tyr Ser Leu Glu Asp Leu Leu Ala Thr
            645                 650                 655

Val Lys Tyr Tyr Val Glu His Pro Asn Glu Arg Pro His Ser Asp Asn
        660                 665                 670

Gly Phe Gly Asn Ala Ser Asp His Val Arg Lys Asn Lys Ala Asp Gln
    675                 680                 685

Asp Ser Lys Pro Asp Glu Asp Lys Glu His Asp Glu Val Ser Glu Pro
    690                 695                 700

Thr His Pro Glu Ser Asp Glu Lys Glu Asn His Ala Gly Leu Asn Pro
705                 710                 715                 720

Ser Ala Asp Asn Leu Tyr Lys Pro Ser Thr Asp Thr Glu Glu Thr Glu
            725                 730                 735

Glu Glu Ala Glu Asp Thr Thr Asp Glu Ala Glu Ile Pro Gln Val Glu
        740                 745                 750

Asn Ser Val Ile Asn Ala Lys Ile Ala Asp Ala Glu Ala Leu Leu Glu
    755                 760                 765

Lys Val Thr Asp Pro Ser Ile Arg Gln Asn Ala Met Glu Thr Leu Thr
    770                 775                 780

Gly Leu Lys Ser Ser Leu Leu Leu Gly Thr Lys Asp Asn Asn Thr Ile
785                 790                 795                 800

Ser Ala Glu Val Asp Ser Leu Leu Ala Leu Leu Lys Glu Ser Gln Pro
            805                 810                 815

Ala Pro Ile Gln
        820

<210> SEQ ID NO 6
<211> LENGTH: 2463
<212> TYPE: DNA
<213> ORGANISM: Streptococcus pneumoniae

<400> SEQUENCE: 6
atgggatcct atgaacttgg tcgtcaccaa gctggtcagg ttaagaaaga gtctaatcga      60
gtttcttata tagatggtga tcaggctggt caaaaggcag aaaatttgac accagatgaa     120

```
gtcagtaaga gagagggdat caacgccgaa caaattgtta tcaagattac ggatcaaggt    180
tatgtgacct ctcatggaga ccattatcat tactataatg gcaaggttcc ttatgatgcc    240
atcatcagtg aagaacttct catgaaagat ccgaattatc agttgaagga ttcagacatt    300
gtcaatgaaa tcaagggtgg ctatgtgatt aaggtagacg gaaaatacta tgtttacctt    360
aaagatgcgg cccatgcgga caatattcgg acaaaagaag agattaaacg tcagaagcag    420
gaacacagtc ataatcataa ctcaagagca gataatgctg ttgctgcagc cagagcccaa    480
ggacgttata caacggatga tgggtatatc ttcaatgcat ctgatatcat tgaggacacg    540
ggtgatgctt atatcgttcc tcacggcgac cattaccatt acattcctaa gaatgagtta    600
tcagctagcg agttagctgc tgcagaagcc tattggaatg ggaagcaggg atctcgtcct    660
tcttcaagtt ctagttataa tgcaaatcca gttcaaccaa gattgtcaga gaccacaat    720 ctgactgtca ctccaactta tcatcaaaat caaggggaaa acatttcaag ccttttacgt    780
gaattgtatg ctaaacccct tatcgaacgc catgtagaat ctgatggcct tatttttcgac   840 ccagcgcaaa tcacaagtcg aaccgccaga ggtgtagctg tccctcatgg taaccattac    900
cactttatcc cttatgaaca aatgtctgaa ttggaaaaac gaattgctcg tattattccc    960
cttcgttatc gttcaaacca ttgggtacca gattcaagac cagaacaacc aagtccacaa   1020
tcgactccgg aacctagtcc aagtctgcaa cctgcaccaa atcctcaacc agctccaagc   1080
aatccaattg atgagaaatt ggtcaaagaa gctgttcgaa aagtaggcga tggttatgtc   1140
tttgaggaga atggagtttc tcgttatatc ccagccaagg atctttcagc agaaacagca   1200
gcaggcattg atagcaaact ggccaagcag gaaagtttat ctcataagct aggagctaag   1260
aaaactgacc tcccatctag tgatcgagaa ttttacaata aggcttatga cttactagca   1320
agaattcacc aagatttact tgataataaa ggtcgacaag ttgattttga ggttttggat   1380
aacctgttgg aacgactcaa ggatgtctca agtgataaag tcaagttagt ggatgatatt   1440
cttgccttct tagctccgat tcgtcatcca gaacgtttag gaaaaccaaa tgcgcaaatt   1500
acctacactg atgatgagat tcaagtagcc aagttggcag gcaagtacac aacagaagac   1560
ggttatatct ttgatcctcg tgatataacc agtgatgagg gggatgccta tgtaactcca   1620
catatgaccc atagccactg gattaaaaaa gatagtttgt ctgaagctga gagagcggca   1680
gcccaggctt atgctaaaga gaaaggtttg accoctcctt cgacagacca tcaggattca   1740
ggaaatactg aggcaaaagg agcagaagct atctacaacc gcgtgaaagc agctaagaag   1800
gtgccacttg atcgtatgcc ttacaatctt caatatactg tagaagtcaa aaacggtagt   1860
ttaatcatac ctcattatga ccattaccat aacatcaaat ttgagtggtt tgacgaaggc   1920
ctttatgagg cacctaaggg gtatagtctt gaggatcttt tggcgactgt caagtactat   1980
gtcgaacatc caaacgaacg tccgcattca gataatggtt ttggtaacgc tagtgaccat   2040
gttcgtaaaa ataaggcaga ccaagatagt aaacctgatg aagataagga acatgatgaa   2100
gtaagtgagc caactcaccc tgaatctgat gaaaaagaga atcacgctgg tttaaatcct   2160
tcagcagata atctttataa accaagcact gatacggaag agacagagga agaagctgaa   2220
gataccacag atgaggctga aattcctcaa gtagagaatt ctgttattaa cgctaagata   2280
gcagatgcgg aggccttgct agaaaaagta acagatccta gtattagaca aaatgctatg   2340
gagacattga ctggtctaaa aagtagtctt cttctcggaa cgaaagataa taacactatt   2400
tcagcagaag tagatagtct cttggctttg ttaaaagaaa gtcaaccggc tcctatacag   2460
tag                                                                 2463
```

<210> SEQ ID NO 7
<211> LENGTH: 445
<212> TYPE: PRT
<213> ORGANISM: Streptococcus pneumoniae

<400> SEQUENCE: 7

```
Met Ala Asp Thr Pro Ser Ser Glu Val Ile Lys Glu Thr Lys Val Gly
 1               5                  10                  15

Ser Ile Ile Gln Gln Asn Asn Ile Lys Tyr Lys Val Leu Thr Val Glu
            20                  25                  30

Gly Asn Ile Gly Thr Val Gln Val Gly Asn Gly Val Thr Pro Val Glu
        35                  40                  45

Phe Glu Ala Gly Gln Asp Gly Lys Pro Phe Thr Ile Pro Thr Lys Ile
    50                  55                  60

Thr Val Gly Asp Lys Val Phe Thr Val Thr Glu Val Ala Ser Gln Ala
65                  70                  75                  80

Phe Ser Tyr Tyr Pro Asp Glu Thr Gly Arg Ile Val Tyr Tyr Pro Ser
                85                  90                  95

Ser Ile Thr Ile Pro Ser Ser Ile Lys Lys Ile Gln Lys Lys Gly Phe
            100                 105                 110

His Gly Ser Lys Ala Lys Thr Ile Ile Phe Asp Lys Gly Ser Gln Leu
        115                 120                 125

Glu Lys Ile Glu Asp Arg Ala Phe Asp Phe Ser Glu Leu Glu Glu Ile
    130                 135                 140

Glu Leu Pro Ala Ser Leu Glu Tyr Ile Gly Thr Ser Ala Phe Ser Phe
145                 150                 155                 160

Ser Gln Lys Leu Lys Lys Leu Thr Phe Ser Ser Ser Lys Leu Glu
                165                 170                 175

Leu Ile Ser His Glu Ala Phe Ala Asn Leu Ser Asn Leu Glu Lys Leu
            180                 185                 190

Thr Leu Pro Lys Ser Val Lys Thr Leu Gly Ser Asn Leu Phe Arg Leu
        195                 200                 205

Thr Thr Ser Leu Lys His Val Asp Val Glu Glu Gly Asn Glu Ser Phe
    210                 215                 220

Ala Ser Val Asp Gly Val Leu Phe Ser Lys Asp Lys Thr Gln Leu Ile
225                 230                 235                 240

Tyr Tyr Pro Ser Gln Lys Asn Asp Glu Ser Tyr Lys Thr Pro Lys Glu
                245                 250                 255

Thr Lys Glu Leu Ala Ser Tyr Ser Phe Asn Lys Asn Ser Tyr Leu Lys
            260                 265                 270

Lys Leu Glu Leu Asn Glu Gly Leu Glu Lys Ile Gly Thr Phe Ala Phe
        275                 280                 285

Ala Asp Ala Ile Lys Leu Glu Glu Ile Ser Leu Pro Asn Ser Leu Glu
    290                 295                 300

Thr Ile Glu Arg Leu Ala Phe Tyr Gly Asn Leu Glu Leu Lys Glu Leu
305                 310                 315                 320

Ile Leu Pro Asp Asn Val Lys Asn Phe Gly Lys His Val Met Asn Gly
                325                 330                 335

Leu Pro Lys Leu Lys Ser Leu Thr Ile Gly Asn Asn Ile Asn Ser Leu
            340                 345                 350

Pro Ser Phe Phe Leu Ser Gly Val Leu Asp Ser Leu Lys Glu Ile His
        355                 360                 365

Ile Lys Asn Lys Ser Thr Glu Phe Ser Val Lys Lys Asp Thr Phe Ala
```

```
                    370                 375                 380
Ile Pro Glu Thr Val Lys Phe Tyr Val Thr Ser Glu His Ile Lys Asp
385                 390                 395                 400

Val Leu Lys Ser Asn Leu Ser Thr Ser Asn Asp Ile Ile Val Glu Lys
            405                 410                 415

Val Asp Asn Ile Lys Gln Glu Thr Asp Val Ala Lys Pro Lys Lys Asn
            420                 425                 430

Ser Asn Gln Gly Val Val Gly Trp Val Lys Asp Lys Gly
            435                 440                 445
```

<210> SEQ ID NO 8
<211> LENGTH: 1338
<212> TYPE: DNA
<213> ORGANISM: Streptococcus pneumoniae

<400> SEQUENCE: 8

```
atggcagata tcctagttc ggaagtaatc aaagagacta agttggaag tattattcaa      60
caaataata tcaaatataa ggttctaact gtagaaggta cataggaac tgttcaagtg     120
ggtaatggag ttactcctgt agagtttgaa gctggtcaag atggaaaacc attcacgatt    180
cctacaaaaa tcacagtagg tgataaagta tttaccgtta ctgaagtagc tagtcaagct    240
tttagttatt atccagatga acaggtaga attgtctact atcctagctc tattactatc    300
ccatcaagca taaaaaaat acaaaaaaaa ggcttccatg gaagtaaagc taaaactatt    360
attttttgaca aaggcagtca gctggagaaa attgaagata gagcttttga tttttctgaa    420
ttagaagaga ttgaattgcc tgcatctcta gaatatattg gaacaagtgc attttctttt    480
agtcaaaaat tgaaaaagct aaccttttcc tcaagttcaa aattagaatt aatatcacat    540
gaggcttttg ctaatttatc aaatttagag aaactaacat taccaaaatc ggttaaaaca    600
ttaggaagta atctatttag actcactact agcttaaaac atgttgatgt tgaagaagga    660
aatgaatcgt ttgcctcagt tgatggtgtt ttgttttcaa aagataaaac tcaattaatt    720
tattatccaa gtcaaaaaaa tgacgaaagt tataaaacgc taaggagac aaaagaactt     780
gcatcatatt cgtttaataa aaattcttac ttgaaaaaac tcgaattgaa tgaaggttta    840
gaaaaaatcg gtacttttgc atttgcggat gcgattaaac ttgaagaaat tagcttacca    900
aatagtttag aaactattga acgtttagcc ttttacggta atttagaatt aaaagaactt    960
atattaccag ataatgttaa aaattttggt aaacacgtta tgaacggttt accaaaatta   1020
aaaagtttaa caattggtaa taatatcaac tcattgccgt ccttcttcct aagtggcgtc    1080
ttagattcat taaaggaaat tcatattaag aataaaagta cagagttttc tgtgaaaaaa    1140
gatacatttg caattcctga aactgttaag ttctatgtaa catcagaaca tataaaagat   1200
gttcttaaat caaatttatc tactagtaat gatatcattg ttgaaaaagt agataatata   1260
aaacaagaaa ctgatgtagc taaacctaaa agaattcta atcagggagt agttggttgg   1320
gttaaagaca aaggttaa                                                1338
```

<210> SEQ ID NO 9
<211> LENGTH: 471
<212> TYPE: PRT
<213> ORGANISM: Streptococcus pneumoniae

<400> SEQUENCE: 9

```
Met Ala Asn Lys Ala Val Asn Asp Phe Ile Leu Ala Met Asn Tyr Asp
1               5                   10                  15
```

-continued

```
Lys Lys Lys Leu Leu Thr His Gln Gly Glu Ser Ile Glu Asn Arg Phe
             20                  25                  30
Ile Lys Glu Gly Asn Gln Leu Pro Asp Glu Phe Val Val Ile Glu Arg
         35                  40                  45
Lys Lys Arg Ser Leu Ser Thr Asn Thr Ser Asp Ile Ser Val Thr Ala
 50                  55                  60
Cys Asn Asp Ser Arg Leu Tyr Pro Gly Ala Leu Leu Val Val Asp Glu
 65                  70                  75                  80
Thr Leu Leu Glu Asn Asn Pro Thr Leu Leu Ala Val Asp Arg Ala Pro
                 85                  90                  95
Met Thr Tyr Ser Ile Asp Leu Pro Gly Leu Ala Ser Ser Asp Ser Phe
            100                 105                 110
Leu Gln Val Glu Asp Pro Ser Asn Ser Ser Val Arg Gly Ala Val Asn
        115                 120                 125
Asp Leu Leu Ala Lys Trp His Gln Asp Tyr Gly Gln Val Asn Asn Val
130                 135                 140
Pro Ala Arg Met Gln Tyr Glu Lys Ile Thr Ala His Ser Met Glu Gln
145                 150                 155                 160
Leu Lys Val Lys Phe Gly Ser Asp Phe Glu Lys Thr Gly Asn Ser Leu
                165                 170                 175
Asp Ile Asp Phe Asn Ser Val His Ser Gly Glu Lys Gln Ile Gln Ile
            180                 185                 190
Val Asn Phe Lys Gln Ile Tyr Tyr Thr Val Ser Val Asp Ala Val Lys
        195                 200                 205
Asn Pro Gly Asp Val Phe Gln Asp Thr Val Thr Val Glu Asp Leu Lys
210                 215                 220
Gln Arg Gly Ile Ser Ala Glu Arg Pro Leu Val Tyr Ile Ser Ser Val
225                 230                 235                 240
Ala Tyr Gly Arg Gln Val Tyr Leu Lys Leu Glu Thr Thr Ser Lys Ser
                245                 250                 255
Asp Glu Val Glu Ala Ala Phe Glu Ala Leu Ile Lys Gly Val Lys Val
            260                 265                 270
Ala Pro Gln Thr Glu Trp Lys Gln Ile Leu Asp Asn Thr Glu Val Lys
        275                 280                 285
Ala Val Ile Leu Cys Gly Asp Pro Ser Ser Gly Ala Arg Val Val Thr
290                 295                 300
Gly Lys Val Asp Met Val Glu Asp Leu Ile Gln Glu Gly Ser Arg Phe
305                 310                 315                 320
Thr Ala Asp His Pro Gly Leu Pro Ile Ser Tyr Thr Thr Ser Phe Leu
                325                 330                 335
Arg Asp Asn Val Val Ala Thr Phe Gln Asn Ser Thr Asp Tyr Val Glu
            340                 345                 350
Thr Lys Val Thr Ala Tyr Arg Asn Gly Asp Leu Leu Leu Asp His Ser
        355                 360                 365
Gly Ala Tyr Val Ala Gln Tyr Tyr Ile Thr Trp Asp Glu Leu Ser Tyr
370                 375                 380
Asp His Gln Gly Lys Glu Val Leu Thr Pro Lys Ala Trp Asp Arg Asn
385                 390                 395                 400
Gly Gln Asp Leu Thr Ala His Phe Thr Thr Ser Ile Pro Leu Lys Gly
                405                 410                 415
Asn Val Arg Asn Leu Ser Val Lys Ile Arg Glu Ala Thr Gly Leu Ala
            420                 425                 430
Trp Glu Trp Trp Arg Thr Val Tyr Glu Lys Thr Asp Leu Pro Leu Val
```

```
            435                 440                 445
Arg Lys Arg Thr Ile Ser Ile Trp Gly Thr Thr Leu Tyr Pro Gln Val
    450                 455                 460

Glu Asp Lys Val Glu Asn Asp
465                 470

<210> SEQ ID NO 10
<211> LENGTH: 471
<212> TYPE: PRT
<213> ORGANISM: Streptococcus pneumonaie

<400> SEQUENCE: 10

Met Ala Asn Lys Ala Val Asn Asp Phe Ile Leu Ala Met Asn Tyr Asp
1               5                   10                  15

Lys Lys Lys Leu Leu Thr His Gln Gly Glu Ser Ile Glu Asn Arg Phe
            20                  25                  30

Ile Lys Glu Gly Asn Gln Leu Pro Asp Glu Phe Val Val Ile Glu Arg
        35                  40                  45

Lys Lys Arg Ser Leu Ser Thr Asn Thr Ser Asp Ile Ser Val Thr Ala
    50                  55                  60

Thr Asn Asp Ser Arg Leu Tyr Pro Gly Ala Leu Leu Val Asp Glu
65                  70                  75                  80

Thr Leu Leu Glu Asn Asn Pro Thr Leu Leu Ala Val Asp Arg Ala Pro
                85                  90                  95

Met Thr Tyr Ser Ile Asp Leu Pro Gly Leu Ala Ser Ser Asp Ser Phe
            100                 105                 110

Leu Gln Val Glu Asp Pro Ser Asn Ser Ser Val Arg Gly Ala Val Asn
        115                 120                 125

Asp Leu Leu Ala Lys Trp His Gln Asp Tyr Gly Gln Val Asn Asn Val
    130                 135                 140

Pro Ala Arg Met Gln Tyr Glu Lys Ile Thr Ala His Ser Met Glu Gln
145                 150                 155                 160

Leu Lys Val Lys Phe Gly Ser Asp Phe Glu Lys Thr Gly Asn Ser Leu
                165                 170                 175

Asp Ile Asp Phe Asn Ser Val His Ser Gly Glu Lys Gln Ile Gln Ile
            180                 185                 190

Val Asn Phe Lys Gln Ile Tyr Tyr Thr Val Ser Val Asp Ala Val Lys
        195                 200                 205

Asn Pro Gly Asp Val Phe Gln Asp Thr Val Thr Val Glu Asp Leu Lys
    210                 215                 220

Gln Arg Gly Ile Ser Ala Glu Arg Pro Leu Val Tyr Ile Ser Ser Val
225                 230                 235                 240

Ala Tyr Gly Arg Gln Val Tyr Leu Lys Leu Glu Thr Thr Ser Lys Ser
                245                 250                 255

Asp Glu Val Glu Ala Ala Phe Glu Ala Leu Ile Lys Gly Val Lys Val
            260                 265                 270

Ala Pro Gln Thr Glu Trp Lys Gln Ile Leu Asp Asn Thr Glu Val Lys
        275                 280                 285

Ala Val Ile Leu Gly Gly Asp Pro Ser Ser Gly Ala Arg Val Val Thr
    290                 295                 300

Gly Lys Val Asp Met Val Glu Asp Leu Ile Gln Glu Gly Ser Arg Phe
305                 310                 315                 320

Thr Ala Asp His Pro Gly Leu Pro Ile Ser Tyr Thr Thr Ser Phe Leu
                325                 330                 335
```

```
Arg Asp Asn Val Val Ala Thr Phe Gln Asn Ser Thr Asp Tyr Val Glu
            340             345             350

Thr Lys Val Thr Ala Tyr Arg Asn Gly Asp Leu Leu Leu Asp His Ser
        355             360             365

Gly Ala Tyr Val Ala Gln Tyr Tyr Ile Thr Trp Asp Glu Leu Ser Tyr
    370             375             380

Asp His Gln Gly Lys Glu Val Leu Thr Pro Lys Ala Trp Asp Arg Asn
385             390             395             400

Gly Gln Asp Leu Thr Ala His Phe Thr Thr Ser Ile Pro Leu Lys Gly
            405             410             415

Asn Val Arg Asn Leu Ser Val Lys Ile Arg Glu Cys Thr Gly Leu Ala
            420             425             430

Trp Glu Trp Trp Arg Thr Val Tyr Glu Lys Thr Asp Leu Pro Leu Val
        435             440             445

Arg Lys Arg Thr Ile Ser Ile Trp Gly Thr Thr Leu Tyr Pro Gln Val
        450             455             460

Glu Asp Lys Val Glu Asn Asp
465             470
```